(12) United States Patent
Shastry

(10) Patent No.: US 12,116,626 B2
(45) Date of Patent: Oct. 15, 2024

(54) AP50 POLYMERASES AND USES THEREOF

(71) Applicant: 10x Genomics, Inc., Pleasanton, CA (US)

(72) Inventor: Shankar Shastry, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 18/450,212

(22) Filed: Aug. 15, 2023

(65) Prior Publication Data
US 2024/0084373 A1    Mar. 14, 2024

Related U.S. Application Data

(60) Provisional application No. 63/398,507, filed on Aug. 16, 2022.

(51) Int. Cl.
C12Q 1/68     (2018.01)
C12N 9/12     (2006.01)
C12Q 1/686    (2018.01)

(52) U.S. Cl.
CPC .......... C12Q 1/686 (2013.01); C12N 9/1247 (2013.01)

(58) Field of Classification Search
None
See application file for complete search history.

(56) References Cited

U.S. PATENT DOCUMENTS

| | | | |
|---|---|---|---|
| 4,318,846 A | 3/1982 | Khanna et al. | |
| 4,683,195 A | 7/1987 | Mullis et al. | |
| 4,683,202 A | 7/1987 | Mullis | |
| 4,757,141 A | 7/1988 | Fung et al. | |
| 4,800,159 A | 1/1989 | Mullis et al. | |
| 4,849,336 A | 7/1989 | Miyoshi et al. | |
| 4,965,188 A | 10/1990 | Mullis et al. | |
| 5,066,580 A | 11/1991 | Lee | |
| 5,091,519 A | 2/1992 | Cruickshank | |
| 5,151,507 A | 9/1992 | Hobbs et al. | |

(Continued)

FOREIGN PATENT DOCUMENTS

WO   WO 2009/045581       4/2009
WO   WO-2009045581 A2 *   4/2009  ............... C12N 7/00

(Continued)

OTHER PUBLICATIONS

Sozhamannan et al., Molecular characterization of a variant of Bacillus anthracis-specific phage AP50 with improved bacteriolytic activity, Appl Environ Microbiol. Nov. 2008; 74(21): 6792-6796, Published online Sep. 12, 2008, doi: 10.1128/AEM.01124-08.*

(Continued)

*Primary Examiner* — Aaron A Priest
(74) *Attorney, Agent, or Firm* — MORRISON & FOERSTER LLP

(57) ABSTRACT

The present disclosure relates in some aspects to recombinant *Bacillus* phage AP50 polymerases, modified AP50 polymerases, and compositions thereof. Also provided are methods of using the recombinant and/or modified AP50 polymerases for nucleic acid amplification (e.g., rolling circle amplification). In some aspects, the compositions and methods disclosed herein provide more robust amplification (e.g., RCA) reactions for improved in vitro and in situ analysis.

20 Claims, 4 Drawing Sheets

Specification includes a Sequence Listing.

(56) References Cited

U.S. PATENT DOCUMENTS

| | | |
|---|---|---|
| 5,188,934 A | 2/1993 | Menchen |
| 5,192,782 A | 3/1993 | Djuric et al. |
| 5,198,537 A | 3/1993 | Huber et al. |
| 5,344,757 A | 9/1994 | Holtke et al. |
| 5,354,657 A | 10/1994 | Boehringer et al. |
| 5,366,860 A | 11/1994 | Bergot et al. |
| 5,512,462 A | 4/1996 | Cheng |
| 5,599,675 A | 2/1997 | Brenner |
| 5,635,352 A | 6/1997 | Urdea et al. |
| 5,688,648 A | 11/1997 | Mathies |
| 5,695,940 A | 12/1997 | Drmanac et al. |
| 5,702,888 A | 12/1997 | Holtke et al. |
| 5,750,341 A | 5/1998 | Macevicz |
| 5,800,996 A | 9/1998 | Lee et al. |
| 5,847,162 A | 12/1998 | Lee et al. |
| 5,990,479 A | 11/1999 | Weiss et al. |
| 6,172,218 B1 | 1/2001 | Brenner |
| 6,207,392 B1 | 3/2001 | Weiss et al. |
| 6,251,303 B1 | 6/2001 | Bawendi et al. |
| 6,265,552 B1 | 7/2001 | Schatz |
| 6,306,597 B1 | 10/2001 | Macevicz |
| 6,319,426 B1 | 11/2001 | Bawendi et al. |
| 6,322,901 B1 | 11/2001 | Bawendi et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,534,266 B1 | 3/2003 | Singer |
| 6,576,291 B2 | 6/2003 | Bawendi et al. |
| 6,969,488 B2 | 11/2005 | Bridgham et al. |
| 7,057,026 B2 | 6/2006 | Barnes et al. |
| 7,255,994 B2 | 8/2007 | Lao |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,562,989 B2 | 10/2013 | Jakobovits et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,217,178 B2 | 12/2015 | Fedurco et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,624,538 B2 | 4/2017 | Church et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,459,603 B2 | 10/2022 | Tyagi et al. |
| 2002/0045045 A1 | 4/2002 | Adams et al. |
| 2003/0017264 A1 | 1/2003 | Treadway et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2009/0118128 A1 | 5/2009 | Liu et al. |
| 2011/0059865 A1 | 3/2011 | Smith et al. |
| 2011/0223585 A1 | 9/2011 | Gullberg et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2014/0094375 A1 | 4/2014 | Kamtekar et al. |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0114379 A1* | 4/2017 | Behlke ........... C12Y 207/07007 |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |

(56) References Cited

U.S. PATENT DOCUMENTS

| | | |
|---|---|---|
| 2019/0276881 A1 | 9/2019 | Zhuang et al. |
| 2019/0339203 A1 | 11/2019 | Miller et al. |
| 2019/0367969 A1 | 12/2019 | Belhocine |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0155909 A1 | 5/2021 | Ong et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340618 A1 | 11/2021 | Kuhnemund et al. |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |

FOREIGN PATENT DOCUMENTS

| | | |
|---|---|---|
| WO | WO 2017/143155 | 8/2017 |
| WO | WO 2018/026873 | 2/2018 |
| WO | WO 2019/199579 | 10/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | WO 2021/155063 | 8/2021 |
| WO | WO 2021/168326 | 8/2021 |
| WO | WO 2024/040060 | 2/2024 |

OTHER PUBLICATIONS

Bibikova et al., "Quantitative gene expression profiling in formalin-fixed, paraffin-embedded tissues using universal bead arrays," Am J Pathol. Nov. 2004; 165(5):1799-807.

Capodieci et al., "Gene expression profiling in single cells within tissue," Nat Methods. (2005) 2(9): 663-5.

Chen et al., "RNA imaging. Spatially resolved, highly multiplexed RNA profiling in single cells," Science. (2015) 348(6233): aaa6090. 16 pgs.

Clackson et al., "Making Antibody Fragments Using Phage Display Libraries," Nature (1991) 352:624-628.

Conze et al., "Single molecule analysis of combinatorial splicing," Nucleic Acids Res. (2010) 38(16): e163.

Costa et al., "Fusion tags for protein solubility, purification and immunogenicity in *Escherichia coli*: the novel Fh8 system," Front Microbiol. (2014) 19:5:63.

Crameri et al., "DNA shuffling of a family of genes from diverse species accelerates directed evolution," Nature (1998) 391: 288-291.

Eng et al., "Transcriptome-scale super-resolved imaging in tissues by RNA seqFISH," Nature. (2019) 568(7751): 235-239.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Gibbs et al., "Degenerate oligonucleotide gene shuffling (DOGS): a method for enhancing the frequency of recombination with family shuffling," Gene. (2001) 271(1):13-20.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Gyllborg et al., "Hybridization-based in situ sequencing (HybISS) for spatially resolved transcriptomics in human and mouse brain tissue," Nucleic Acids Res. (2020) 48(19): e112.

Han et al., "Quantum-dot-tagged microbeads for multiplexed optical coding of biomolecules," Nat Biotechnol. (2001) 19(7): 631-5.

Henegariu et al., "Custom fluorescent-nucleotide synthesis as an alternative method for nucleic acid labeling," Nature Biotechnol. (2000) 18:345.

Henikoff et al., "Amino acid substitution matrices from protein blocks," Proc Natl Acad Sci USA. (1992) 89(22):10915-9.

Hiraga et al., "General method for sequence-independent site-directed chimeragenesis," J Mol Biol. (2003) 330(2):287-96.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Kimple et al., "Overview of affinity tags for protein purification," Curr Protoc Protein Sci. (2013) 73: 9.9.1-9.9.23.

Korlach et al. "Selective aluminum passivation for targeted immobilization of single DNA polymerase molecules in zero-mode waveguide nanostructures." *Proceedings of the National Academy of Sciences* 105.4 (2008): 1176-1181.

Lagunavicius et al., "Novel application of Phi29 DNA polymerase: RNA detection and analysis in vitro and in situ by target RNA-primed RCA," RNA. (2009) 15(5):765-71.

Lakowicz et al., "Silver particles enhance emission of fluorescent DNA oligomers," Bio Techniques (2003) 34(1); 62-66.

Larsson et al. "In situ detection and genotyping of individual mRNA molecules," Nat Methods. (2010) 7(5):395-397.

Lee et al. "Highly Multiplexed Subcellular RNA Sequencing In Situ", Science (2014) 343(6177):1360-1363.

Lei et al., "Structure-function analysis of human glucose-6-phosphatase, the enzyme deficient in glycogen storage disease type 1a," J Biol Chem. (1995) 270(20):11882-6.

Levene et al. "Zero-mode waveguides for single-molecule analysis at high concentrations." science 299.5607 (2003): 682-686.

Levsky et al., "Fluorescence in situ hybridization: past, present and future," J Cell Sci. (2003) 116(Pt 14): 2833-8.

(56) References Cited

OTHER PUBLICATIONS

Levsky et al., "Single-cell gene expression profiling," Science. (2002) 297(5582): 836-40.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lundquist et al. "Parallel confocal detection of single molecules in real time." Optics letters 33.9 (2008): 1026-1028.

Lyamichev et al., "Comparison of the 5' nuclease activities of taq DNA polymerase and its isolated nuclease domain," Proc Natl Acad Sci USA. (1999) 96(11): 6143-6148.

Ma et al., "RNA template-dependent 5' nuclease activity of Thermus aquaticus and Thermus thermophilus DNA polymerases," J Biol Chem. (2000) 275(32): 24693-700.

Maierhorfer et al., "Multicolor deconvolution microscopy of thick biological specimens," Am J Pathol. (2003) 162(2): 373-9.

McGinn et al., "New technologies for DNA analysis—a review of the READNA Project," N Biotechnol. (2016) 33(3): 311-30. doi: 10.1016/j.nbt.2015.10.003.

Meade et al. "Multiplexed DNA detection using spectrally encoded porous SiO2 photonic crystal particles," Anal Chem. (2009) 81(7): 2618-25.

Mitra et al., "Fluorescent in situ sequencing on polymerase colonies," Anal. Biochem. (2003) 320, 55-65.

Nagy et al., "Characteristics of phage AP50, an RNA phage containing phospholipids," J Gen Virol. (1976) 32(1):129-32.

Ordonez et al., "Engineered viral DNA polymerase with enhanced DNA amplification capacity: a proof-of-concept of isothermal amplification of damaged DNA," Sci Rep. (2020) 10(1):15046.

Pavlov et al., "Helix-hairpin-helix motifs confer salt resistance and processivity on chimeric DNA polymerases," Proc Natl Acad Sci USA. (2002) 99(21):13510-5.

Payne et al. "In situ genome sequencing resolves DNA sequence and structure in intact biological samples," Science. (2021) 371(6532): eaay3446. doi: 10.1126/science.aay3446. Epub Dec. 31, 2020.

Raj et al., "Imaging individual mRNA molecules using multiple singly labeled probes," Nat Methods. (2008) 5(10): 877-879.

Rajeswari et al., "Multiple pathogen biomarker detection using an encoded bead array in droplet PCR," J Microbiol Methods. (2017) 139: 22-28.

Rouhanifard et al. "ClampFISH detects individual nucleic acid molecules using click chemistry-based amplification," Nat Biotechnol. (2018) 17 pages. doi: 10.1038/nbt.4286.

Shendure et al., "Accurate multiplex polony sequencing of an evolved bacterial genome," Science (2005) 309(5741); 1728-1732.

Sozhamannan et al., "Molecular characterization of a variant of Bacillus anthracis-specific phage AP50 with improved bacteriolytic activity," Appl Environ Microbiol. (2008) 74(21):6792-6.

Sun et al., "Composite organic-inorganic nanoparticles as Raman labels for tissue analysis," Nano Lett. (2007) 7(2): 351-6.

Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.

Wählby et al., "Sequential immunofluorescence staining and image analysis for detection of large numbers of antigens in individual cell nuclei," Cytometry. (2002) 47(1): 32-41.

Weibrecht et al., "Simultaneous visualization of both signaling cascade activity and end-point gene expression in single cells," PLoS One. (2011) 6(5): e20148.

Wetmur, "DNA Probes: Applications of the Principles of Nucleic Acid Hybridization," Critical Reviews in Biochemistry and Molecular Biology, (1991) 26(91); 227-259.

Wilson et al., "Encoded microcarriers for high-throughput multiplexed detection," Angew Chem Int Ed Engl. (2006) 18;45(37): 6104-17.

Wu et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.

Zhao et al., "Advances of multiplex and high throughput biomolecular detection technologies based on encoding microparticles," Sci China Chem. (2011) 54(8):1185.

* cited by examiner

SEQUENCE LISTING

```
Sequence total quantity: 38
SEQ ID NO: 1            moltype = AA   length = 731
FEATURE                 Location/Qualifiers
REGION                  1..731
                        note = APol (aa) without initial Met
source                  1..731
                        mol_type = protein
                        organism = Synthetic construct
SEQUENCE: 1
GSNKQKKERQ KPAKLLTLDT ETRGLTGNVF RVGLFDGTNY YKSNTFDEIL DLFEQYKDYE   60
CHVYVHNLDF DLAKIATTLF KRDRVRFAKS IFINGNVVTL HSDSMILHDS LRLLPGSLEK  120
LCKDFGLTDN AKKDLSEVIK EQGYAVYKKD GVTFDKKKSL GNYFENVPAD DPTLNEYLEF  180
DCRSLYEILT IVMDIANIGL ETLVMCPTTA SLAMRVYKEQ YREQYDKVAT HFYMGEWGQF  240
LEEHVRQSYY GGRTEVFTPH LPHGYHYDVN SLYPYVMKIA KFPVGYPNLL KDGQAATKWK  300
HWKRRAIGGG VMWCRVDVPE DMYIPVLPKR DPSGKLLFPV GKLEGVWTLP ELLEAEKNGC  360
TIEAIYQMVY WEHMEPIFKE FVEHFEDLKK NSKGAKRTFA KLIQNSLYGK FGMNRVRVSL  420
GDMEDRYDLH EKQIPYKEFK HDCNGLTLEF IQYISESKAS YIQPHIATYV TAYARILLFR  480
GLKEQASKGV LGYCDTDSIA GTAKMPDEMI HDEDYGKWAL EGELEEGIFL QPKFYAERYT  540
NGKEVIKAKG IPREKMEELS FENYKEWLEI MKEGQQERID IFEGYESRKK FSTTLKASED  600
FDTLREMKKS INLLLEQKRD IDYKGNVTRP HKRYDYGDKK DKIDYEDYKS REDKLNNMYD  660
DVDDLKEQVD EIGYIKCMKQ GDMYFEEYKH LTKSVKSKYF RRTGTPIDVW ANESGWDVNE  720
LLEELRLMGV C                                                      731

SEQ ID NO: 2            moltype = AA   length = 740
FEATURE                 Location/Qualifiers
REGION                  1..740
                        note = APol-His (aa) without initial Met
source                  1..740
                        mol_type = protein
                        organism = Synthetic construct
SEQUENCE: 2
GSNKQKKERQ KPAKLLTLDT ETRGLTGNVF RVGLFDGTNY YKSNTFDEIL DLFEQYKDYE   60
CHVYVHNLDF DLAKIATTLF KRDRVRFAKS IFINGNVVTL HSDSMILHDS LRLLPGSLEK  120
LCKDFGLTDN AKKDLSEVIK EQGYAVYKKD GVTFDKKKSL GNYFENVPAD DPTLNEYLEF  180
DCRSLYEILT IVMDIANIGL ETLVMCPTTA SLAMRVYKEQ YREQYDKVAT HFYMGEWGQF  240
LEEHVRQSYY GGRTEVFTPH LPHGYHYDVN SLYPYVMKIA KFPVGYPNLL KDGQAATKWK  300
HWKRRAIGGG VMWCRVDVPE DMYIPVLPKR DPSGKLLFPV GKLEGVWTLP ELLEAEKNGC  360
TIEAIYQMVY WEHMEPIFKE FVEHFEDLKK NSKGAKRTFA KLIQNSLYGK FGMNRVRVSL  420
GDMEDRYDLH EKQIPYKEFK HDCNGLTLEF IQYISESKAS YIQPHIATYV TAYARILLFR  480
GLKEQASKGV LGYCDTDSIA GTAKMPDEMI HDEDYGKWAL EGELEEGIFL QPKFYAERYT  540
NGKEVIKAKG IPREKMEELS FENYKEWLEI MKEGQQERID IFEGYESRKK FSTTLKASED  600
FDTLREMKKS INLLLEQKRD IDYKGNVTRP HKRYDYGDKK DKIDYEDYKS REDKLNNMYD  660
DVDDLKEQVD EIGYIKCMKQ GDMYFEEYKH LTKSVKSKYF RRTGTPIDVW ANESGWDVNE  720
LLEELRLMGV CGGSHHHHHH                                             740

SEQ ID NO: 3            moltype = AA   length = 646
FEATURE                 Location/Qualifiers
REGION                  1..646
                        note = APolTr-His (aa) without initial Met
source                  1..646
                        mol_type = protein
                        organism = Synthetic construct
SEQUENCE: 3
GSNKQKKERQ KPAKLLTLDT ETRGLTGNVF RVGLFDGTNY YKSNTFDEIL DLFEQYKDYE   60
CHVYVHNLDF DLAKIATTLF KRDRVRFAKS IFINGNVVTL HSDSMILHDS LRLLPGSLEK  120
LCKDFGLTDN AKKDLSEVIK EQGYAVYKKD GVTFDKKKSL GNYFENVPAD DPTLNEYLEF  180
DCRSLYEILT IVMDIANIGL ETLVMCPTTA SLAMRVYKEQ YREQYDKVAT HFYMGEWGQF  240
LEEHVRQSYY GGRTEVFTPH LPHGYHYDVN SLYPYVMKIA KFPVGYPNLL KDGQAATKWK  300
HWKRRAIGGG VMWCRVDVPE DMYIPVLPKR DPSGKLLFPV GKLEGVWTLP ELLEAEKNGC  360
TIEAIYQMVY WEHMEPIFKE FVEHFEDLKK NSKGAKRTFA KLIQNSLYGK FGMNRVRVSL  420
GDMEDRYDLH EKQIPYKEFK HDCNGLTLEF IQYISESKAS YIQPHIATYV TAYARILLFR  480
GLKEQASKGV LGYCDTDSIA GTAKMPDEMI HDEDYGKWAL EGELEEGIFL QPKFYAERYT  540
NGKEVIKAKG IPREKMEELS FENYKEWLEI MKEGQQERID IFEGYESRKK FSTTLKASED  600
FDTLREMKKS INLLLEQKRD IDYKGNVTRP HKRYDYGGGS HHHHHH                646

SEQ ID NO: 4            moltype = AA   length = 657
FEATURE                 Location/Qualifiers
REGION                  1..657
                        note = APolTr-His-SET (aa) without initial Met
source                  1..657
                        mol_type = protein
                        organism = Synthetic construct
SEQUENCE: 4
GSNKQKKERQ KPAKLLTLDT ETRGLTGNVF RVGLFDGTNY YKSNTFDEIL DLFEQYKDYE   60
CHVYVHNLDF DLAKIATTLF KRDRVRFAKS IFINGNVVTL HSDSMILHDS LRLLPGSLEK  120
LCKDFGLTDN AKKDLSEVIK EQGYAVYKKD GVTFDKKKSL GNYFENVPAD DPTLNEYLEF  180
DCRSLYEILT IVMDIANIGL ETLVMCPTTA SLAMRVYKEQ YREQYDKVAT HFYMGEWGQF  240
LEEHVRQSYY GGRTEVFTPH LPHGYHYDVN SLYPYVMKIA KFPVGYPNLL KDGQAATKWK  300
```

```
                                               -continued
HWKRRAIGGG VMWCRVDVPE DMYIPVLPKR DPSGKLLFPV GKLEGVWTLP ELLEAEKNGC    360
TIEAIYQMVY WEHMEPIFKE FVEHFEDLKK NSKGAKRTFA KLIQNSLYGK FGMNRVRVSL    420
GDMEDRYDLH EKQIPYKEFK HDCNGLTLEF IQYISESKAS YIQPHIATYV TAYARILLFR    480
GLKEQASKGV LGYCDTDSIA GTAKMPDEMI HDEDYGKWAL EGELEEGIFL QPKFYAERYT    540
NGKEVIKAKG IPREKMEELS FENYKEWLEI MKEGQQERID IFEGYESRKK FSTTLKASED    600
FDTLREMKKS INLLLEQKRD IDYKGNVTRP HKRYDYGGGS HHHHHHSEED EEKEEDG       657

SEQ ID NO: 5            moltype = AA  length = 574
FEATURE                 Location/Qualifiers
REGION                  1..574
                        note = Phi29 WT (aa) without initial Met
source                  1..574
                        mol_type = protein
                        organism = Synthetic construct
SEQUENCE: 5
KHMPRKMYSC DFETTTKVED CRVWAYGYMN IEDHSEYKIG NSLDEFMAWV LKVQADLYFH     60
NLKFDGAFII NWLERNGFKW SADGLPNTYN TIISRMGQWY MIDICLGYKG KRKIHTVIYD    120
SLKKLPFPVK KIAKDFKLTV LKGDIDYHKE RPVGYKITPE EYAYIKNDIQ IIAEALLIQF    180
KQGLDRMTAG SDSLKGFKDI ITTKKFKKVF PTLSLGLDKE VRYAYRGGFT WLNDRFKEKE    240
IGEGMVFDVN SLYPAQMYSR LLPYGEPIVF EGKYVWDEDY PLHIQHIRCE FELKEGYIPT    300
IQIKRSRFYK GNEYLKSSGG EIADLWLSNV DLELMKEHYD LYNVEYISGL KFKATTGLFK    360
DFIDKWTYIK TTSEGAIKQL AKLMLNSLYG KFASNPDVTG KVPLKENGA LGFRLGEEET    420
KDPVYTPMGV FITAWARYTT ITAAQACYDR IIYCDTDSIH LTGTEIPDVI KDIVDPKKLG    480
YWAHESTFKR AKYLRQKTYI QDIYMKEVDG KLVEGSPDDY TDIKFSVKCA GMTDKIKKEV    540
TFENFKVGFS RKMKPKPVQV PGGVVLVDDT FTIK                                574

SEQ ID NO: 6            moltype = AA  length = 637
FEATURE                 Location/Qualifiers
REGION                  1..637
                        note = APolTr (aa) without initial Met
source                  1..637
                        mol_type = protein
                        organism = Synthetic construct
SEQUENCE: 6
GSNKQKKERQ KPAKLLTLDT ETRGLTGNVF RVGLFDGTNY YKSNTFDEIL DLFEQYKDYE     60
CHVYVHNLDF DLAKIATTLF KRDRVRFAKS IFINGNVVTL HSDSMILHDS LRLLPGSLEK    120
LCKDFGLTDN AKKDLSEVIK EQGYAVYKKD GVTFDKKKSL GNYFENVPAD DPTLNEYLEF    180
DCRSLYEILT IVMDIANIGL ETLVMCPTTA SLAMRVYKEQ YREQYDKVAT HPFYMGEWGQF    240
LEEHVRQSYY GGRTEVFTPH LPHGYHYDVN SLYPYVMKIA KFPVGYPNLL KDGQAATKWK    300
HWKRRAIGGG VMWCRVDVPE DMYIPVLPKR DPSGKLLFPV GKLEGVWTLP ELLEAEKNGC    360
TIEAIYQMVY WEHMEPIFKE FVEHFEDLKK NSKGAKRTFA KLIQNSLYGK FGMNRVRVSL    420
GDMEDRYDLH EKQIPYKEFK HDCNGLTLEF IQYISESKAS YIQPHIATYV TAYARILLFR    480
GLKEQASKGV LGYCDTDSIA GTAKMPDEMI HDEDYGKWAL EGELEEGIFL QPKFYAERYT    540
NGKEVIKAKG IPREKMEELS FENYKEWLEI MKEGQQERID IFEGYESRKK FSTTLKASED    600
FDTLREMKKS INLLLEQKRD IDYKGNVTRP HKRYDYG                              637

SEQ ID NO: 7            moltype = AA  length = 6
FEATURE                 Location/Qualifiers
REGION                  1..6
                        note = 6x His tag (aa)
source                  1..6
                        mol_type = protein
                        organism = Synthetic construct
SEQUENCE: 7
HHHHHH                                                                 6

SEQ ID NO: 8            moltype = AA  length = 11
FEATURE                 Location/Qualifiers
REGION                  1..11
                        note = Solubility enhancement tag (SET)(aa)
source                  1..11
                        mol_type = protein
                        organism = Synthetic construct
SEQUENCE: 8
SEEDEEKEED G                                                          11

SEQ ID NO: 9            moltype = AA  length = 20
FEATURE                 Location/Qualifiers
REGION                  1..20
                        note = GSS linker-6x His-SET (aa)
source                  1..20
                        mol_type = protein
                        organism = Synthetic construct
SEQUENCE: 9
GGSHHHHHHS EEDEEKEEDG                                                 20

SEQ ID NO: 10           moltype =     length =
SEQUENCE: 10
000
```

```
SEQ ID NO: 11            moltype = AA   length = 5
FEATURE                  Location/Qualifiers
REGION                   1..5
                         note = GGSGG linker (aa)
source                   1..5
                         mol_type = protein
                         organism = Synthetic construct
SEQUENCE: 11
GGSGG                                                                    5

SEQ ID NO: 12            moltype = AA   length = 5
FEATURE                  Location/Qualifiers
REGION                   1..5
                         note = GGGGG linker (aa)
source                   1..5
                         mol_type = protein
                         organism = Synthetic construct
SEQUENCE: 12
GGGGG                                                                    5

SEQ ID NO: 13            moltype = AA   length = 5
FEATURE                  Location/Qualifiers
REGION                   1..5
                         note = GGAGG linker (aa)
source                   1..5
                         mol_type = protein
                         organism = Synthetic construct
SEQUENCE: 13
GGAGG                                                                    5

SEQ ID NO: 14            moltype = AA   length = 7
FEATURE                  Location/Qualifiers
REGION                   1..7
                         note = GGGGSSS linker (aa)
source                   1..7
                         mol_type = protein
                         organism = Synthetic construct
SEQUENCE: 14
GGGGSSS                                                                  7

SEQ ID NO: 15            moltype = AA   length = 7
FEATURE                  Location/Qualifiers
REGION                   1..7
                         note = GGGGAAA linker (aa)
source                   1..7
                         mol_type = protein
                         organism = Synthetic construct
SEQUENCE: 15
GGGGAAA                                                                  7

SEQ ID NO: 16            moltype = AA   length = 50
FEATURE                  Location/Qualifiers
REGION                   1..50
                         note = GGGGS linker
VARIANT                  5..50
                         note = may be absent
source                   1..50
                         mol_type = protein
                         organism = Synthetic construct
SEQUENCE: 16
GGGGSGGGGS GGGGSGGGGS GGGGSGGGGS GGGGSGGGGS GGGGSGGGGS                   50

SEQ ID NO: 17            moltype = DNA   length = 2193
FEATURE                  Location/Qualifiers
misc_feature             1..2193
                         note = APol (nt)
source                   1..2193
                         mol_type = other DNA
                         organism = Synthetic construct
SEQUENCE: 17
ggctccaata agcaaaagaa agagcgccaa aagccggcca agcttctcac cttggacact         60
gagacgcgcg gcctcaccgg taatgtgttc cgcgttggcc tgtttgacgg gacgaattat        120
tacaagtcga atacattcga cgagatcctt gacctgttcg agcaatataa agattacgaa        180
tgtcatgtat acgtacacaa tttagacttc gacttggcga aaatcgccac cactttgttc        240
aagcgcgacc gtgtgcgctt tgcgaagagc atcttcatta acggtaacgt agtgactttg        300
cattcggact cgatgatctt acatgatagc ttacgcttac tgccgggggtc tctgaaaaag        360
ctctgtaaag attttggcct gaccgacaac gccaagaaag atctttccga agtcatcaaa        420
gagcagggtt acgcagtata caagaaagac ggtgtgcacat ttgacaagaa gaaatcccctt       480
```

```
ggcaattatt ttgagaacgt gcctgccgac gaccctacgc tcaatgagta cttggagttc    540
gattgtcgca gcctgtacga gattttgacg attgtgatgg acatcgcaaa tattggcctg    600
gaaaccttag taatgtgccc gaccacagcg agcttagcca tgcgtgtcta taaagagcaa    660
taccgcgagc aatatgataa ggtggccact cactttata tgggcgagtg gggtcaattc      720
ctcgaagagc acgttcgcca atcgtactac ggtggtcgca ctgaggtatt taccccctcat    780
ttaccacatg gttaccatta cgatgttaac tcgttgtacc cgtatgtcat gaaaattgca    840
aagttcccgg tagggtaccc aaatttattg aaagacggcc aggcagctac caagtggaag    900
cattggaagc gtcgtgcgat cggggcggt gttatgtggt gtcgtgtgga cgttcctgaa     960
gacatgtaca tcccagtgct cccgaagcgt gacccgagcg ggaagttatt gttcccggtt   1020
ggtaagctcg agggagtgtg gaccctgcct gagctcctgg aagcggaaaa gaatggctgt   1080
acgatcgagg cgatttacca gatggtatac tgggagcata tggagccgat ctttaaagaa   1140
ttcgttgagc actttgaaga cctcaagaag aacagtaagg gagcgaagcg cacctttgca   1200
aagcttatcc agaatagctt gtacgggaag ttcggcatga accgcgttcg tgtgtcgttg   1260
ggtgacatgg aagaccgtta cgacttgcat gagaagcaga ttccatataa agaattcaaa   1320
catgattgta atggcttgac gcttgagttc atccaatata tctcggaaag caaagcgagc   1380
tatattcaac cgcacattgc tacatacgta acagcctatg ctcgtatcct gttgtttcgt   1440
ggtctgaaag aacaggctag caagggcgta ctgggctatt gcgatactga ctctattgcc   1500
ggtaccgcca aaatgccgga cgaaatgatc catgacgaag attacggcaa gtgggccttc   1560
gaaggtgagc tggaagaagg tatctttctc cagccgaagt tttacgcgga acgttacacg   1620
aacggcaaaa agtaattaa ggccaagggg attccacgcg agaagatgga agagttaagt    1680
ttcgagaact ataagagtg gctcgagatt atgaaagaag gccaacaaga gcgcatcgac    1740
atctttgaag gttacgagag tcgcaagaag tttagcacca cactcaaggc cagtgaagat   1800
ttcgacacgt tgcgtgagat gaagaagtct atcaatttac tgctcgagca gaagcgcgac   1860
atcgactaca agggcaacgt gacacgtcca cataagcgct atgactacgg tgataagaaa   1920
gacaagatcg attatgaaga ctataagagc cgtgaagaca agttaaacaa catgtacgac   1980
gatgtagacg acttaaaaga gcaagttgac gagatcggct acatcaagtg catgaagcaa   2040
ggcgatatgt attttgaaga gtacaaacat cttacgaagt ctgtgaaaag taagtatttc   2100
cgccgcactg gcaccccaat cgacgtatgg gcgaacgaat ccggttggga cgtaaacgag   2160
ttattagaag agcttcgtct gatgggcgtg tgc                                 2193

SEQ ID NO: 18           moltype = DNA  length = 2220
FEATURE                 Location/Qualifiers
misc_feature            1..2220
                        note = APol-His (nt)
source                  1..2220
                        mol_type = other DNA
                        organism = Synthetic construct
SEQUENCE: 18
ggctccaata agcaaaagaa agagcgccaa aagccggcca agcttctcac cttggacact     60
gagacgcgcg gcctcaccgg taatgtgttc cgcgttggcc tgtttgacgg gacgaattat    120
tacaagtcga atacattcga cgagatcctt gacctgttcg agcaatataa agattacgaa    180
tgtcatgtat acgtacacaa tttagacttc gacttggcga aaatcgccac cactttgttc    240
aagccggacc gtgtgcgctt tgcgaagagc atcttcatta acgtaacgt agtgacttg     300
cattcggact cgatgatctt acatgatagc ttacgcttac tgccggggtc tctgaaaag    360
ctctgtaaag attttggcct gaccgacaac gccaagaaag atctttccga agtcatcaaa    420
gagcagggtt acgcagtata caagaaagac ggtgtgcacat ttgacaagaa gaaatccctt   480
ggcaattatt ttgagaacgt gcctgccgac gaccctacgc tcaatgagta cttggagttc    540
gattgtcgca gcctgtacga gattttgacg attgtgatgg acatcgcaaa tattggcctg    600
gaaaccttag taatgtgccc gaccacagcg agcttagcca tgcgtgtcta taaagagcaa    660
taccgcgagc aatatgataa ggtggccact cactttata tgggcgagtg gggtcaattc      720
ctcgaagagc acgttcgcca atcgtactac ggtggtcgca ctgaggtatt taccccctcat    780
ttaccacatg gttaccatta cgatgttaac tcgttgtacc cgtatgtcat gaaaattgca    840
aagttcccgg tagggtaccc aaatttattg aaagacggcc aggcagctac caagtggaag    900
cattggaagc gtcgtgcgat cggggcggt gttatgtggt gtcgtgtgga cgttcctgaa     960
gacatgtaca tcccagtgct cccgaagcgt gacccgagcg ggaagttatt gttcccggtt   1020
ggtaagctcg agggagtgtg gaccctgcct gagctcctgg aagcggaaaa gaatggctgt   1080
acgatcgagg cgatttacca gatggtatac tgggagcata tggagccgat ctttaaagaa   1140
ttcgttgagc actttgaaga cctcaagaag aacagtaagg gagcgaagcg cacctttgca   1200
aagcttatcc agaatagctt gtacgggaag ttcggcatga accgcgttcg tgtgtcgttg   1260
ggtgacatgg aagaccgtta cgacttgcat gagaagcaga ttccatataa agaattcaaa   1320
catgattgta atggcttgac gcttgagttc atccaatata tctcggaaag caaagcgagc   1380
tatattcaac cgcacattgc tacatacgta acagcctatg ctcgtatcct gttgtttcgt   1440
ggtctgaaag aacaggctag caagggcgta ctgggctatt gcgatactga ctctattgcc   1500
ggtaccgcca aaatgccgga cgaaatgatc catgacgaag attacggcaa gtgggccttc   1560
gaaggtgagc tggaagaagg tatctttctc cagccgaagt tttacgcgga acgttacacg   1620
aacggcaaaa agtaattaa ggccaagggg attccacgcg agaagatgga agagttaagt    1680
ttcgagaact ataagagtg gctcgagatt atgaaagaag gccaacaaga gcgcatcgac    1740
atctttgaag gttacgagag tcgcaagaag tttagcacca cactcaaggc cagtgaagat   1800
ttcgacacgt tgcgtgagat gaagaagtct atcaatttac tgctcgagca gaagcgcgac   1860
atcgactaca agggcaacgt gacacgtcca cataagcgct atgactacgg tgataagaaa   1920
gacaagatcg attatgaaga ctataagagc cgtgaagaca agttaaacaa catgtacgac   1980
gatgtagacg acttaaaaga gcaagttgac gagatcggct acatcaagtg catgaagcaa   2040
ggcgatatgt attttgaaga gtacaaacat cttacgaagt ctgtgaaaag taagtatttc   2100
cgccgcactg gcaccccaat cgacgtatgg gcgaacgaat ccggttggga cgtaaacgag   2160
ttattagaag agcttcgtct gatgggcgtg tgcggtggct cacatcacca ccatcatcat   2220

SEQ ID NO: 19           moltype = DNA  length = 1938
FEATURE                 Location/Qualifiers
misc_feature            1..1938
```

|  | note = APolTr-His (nt) |
| --- | --- |
| source | 1..1938 |
|  | mol_type = other DNA |
|  | organism = Synthetic construct |

SEQUENCE: 19

```
ggctccaata agcaaaagaa agagcgccaa aagccggcca agcttctcac cttggacact   60
gagacgcgcg gcctcaccgg taatgtgttc cgcgttggcc tgtttgacgg gacgaattat  120
tacaagtcga atacattcga cgagatcctt gacctgttcg agcaatataa agattacgaa  180
tgtcatgtat acgtacacaa tttagacttc gacttggcga aaatcgccac cactttgttc  240
aagcgcgacc gtgtgcgctt tgcgaagagc atcttcatta acggtaacgt agtgactttg  300
cattcggact cgatgatctt acatgatagc ttacgcttac tgccggggtc tctgaaaaag  360
ctctgtaaag atttttggcct gaccgacaac gccaagaaag atctttccga agtcatcaaa  420
gagcagggtt acgcagtata caagaaagac ggtgtcacat ttgacaagaa gaaatccctt  480
ggcaattatt ttgagaacgt gcctgccgac gaccctacgc tcaatgagta cttggagttc  540
gattgtcgca gcctgtacga gattttgacg attgtgatgg acatcgcaaa tattggcctg  600
gaaaccttag taatgtgccc gaccacagcg agcttagcca tgcgtgtcta taagagcaa   660
taccgcgagc aatatgataa ggtggccact cactttata tgggcgagtg gggtcaattc  720
ctcgaagagc acgttcgcca atcgtactac ggtggtcgca ctgaggtatt taccccctcat  780
ttaccacatg gttaccatta cgatgttaac tcgttgtacc cgtatgtcat gaaaattgca  840
aagttcccgg tagggtaccc aaatttattg aaagacggcc aggcagctac caagtggaag  900
cattggaagc gtcgtgcgat cggggcggt gttatgtggt gtcgtgtgga cgttcctgaa   960
gacatgtaca tcccagtgct cccgaagcgt gacccgagcg ggaagttatt gttcccggtt 1020
ggtaagctcg agggagtgtg gaccctgcct gagctcctgg aagcggaaaa gaatggctgt 1080
acgatcgagg cgatttacca gatggtatac tgggagcata tggagccgat cttaaaagaa 1140
ttcgttgagc actttgaaga cctcaagaag aacagtaagg gagcgaagcg cacctttgca 1200
aagcttatcc agaatagctt gtacgggaag ttcggcatga accgcgttcg tgtgtcgttg 1260
ggtgacatgg aagaccgtta cgacttgcat gagaagcaga ttccatataa agaattcaaa 1320
catgattgta atggcttgac gcttgagttc atccaatata tctcggaaag caaagcgagc 1380
tatattcaac cgcacattgc tacatacgta acagcctatg ctcgtatcct gttgtttcgt 1440
ggtctgaaag aacaggctag caagggcgta ctgggctatt gcgatactga ctctattgcc 1500
ggtaccgcca aaatgccgga cgaaatgatc catgacgaag attacggcaa gtgggccttg 1560
gaaggtgagc tggaagaagg tatctttctc cagccgaagt tttacgcgga acgttacacg 1620
aacggcaaag aagtaattaa ggccaagggg attccacgcg agaagatgga agagttaagt 1680
ttcgagaact ataaagagtg gctcgagatt atgaaagaag ccaacaaga gcgcatcgac 1740
atctttgaag gttacgagag tcgcaagaag tttagcacca cactcaaggc cagtgaagat 1800
ttcgacacgt tgcgtgagat gaagaagtct atcaatttac tgctcgagca gaagcgcgac 1860
atcgactaca agggcaacgt gacacgtcca cataagcgct atgactacgg tggtggctca 1920
catcaccacc atcatcat                                                1938
```

|  |  |
| --- | --- |
| SEQ ID NO: 20 | moltype = DNA length = 1972 |
| FEATURE | Location/Qualifiers |
| misc_feature | 1..1972 |
|  | note = APolTr-His-SET (nt) |
| source | 1..1972 |
|  | mol_type = other DNA |
|  | organism = Synthetic construct |

SEQUENCE: 20

```
ggctccaata agcaaaagaa agagcgccaa aagccggcca agcttctcac cttggacact   60
gagacgcgcg gcctcaccgg taatgtgttc cgcgttggcc tgtttgacgg gacgaattat  120
tacaagtcga atacattcga cgagatcctt gacctgttcg agcaatataa agattacgaa  180
tgtcatgtat acgtacacaa tttagacttc gacttggcga aaatcgccac cactttgttc  240
aagcgcgacc gtgtgcgctt tgcgaagagc atcttcatta acggtaacgt agtgactttg  300
cattcggact cgatgatctt acatgatagc ttacgcttac tgccggggtc tctgaaaaag  360
ctctgtaaag atttttggcct gaccgacaac gccaagaaag atctttccga agtcatcaaa  420
gagcagggtt acgcagtata caagaaagac ggtgtcacat ttgacaagaa gaaatccctt  480
ggcaattatt ttgagaacgt gcctgccgac gaccctacgc tcaatgagta cttggagttc  540
gattgtcgca gcctgtacga gattttgacg attgtgatgg acatcgcaaa tattggcctg  600
gaaaccttag taatgtgccc gaccacagcg agcttagcca tgcgtgtcta taagagcaa   660
taccgcgagc aatatgataa ggtggccact cactttata tgggcgagtg gggtcaattc  720
ctcgaagagc acgttcgcca atcgtactac ggtggtcgca ctgaggtatt taccccctcat  780
ttaccacatg gttaccatta cgatgttaac tcgttgtacc cgtatgtcat gaaaattgca  840
aagttcccgg tagggtaccc aaatttattg aaagacggcc aggcagctac caagtggaag  900
cattggaagc gtcgtgcgat cggggcggt gttatgtggt gtcgtgtgga cgttcctgaa   960
gacatgtaca tcccagtgct cccgaagcgt gacccgagcg ggaagttatt gttcccggtt 1020
ggtaagctcg agggagtgtg gaccctgcct gagctcctgg aagcggaaaa gaatggctgt 1080
acgatcgagg cgatttacca gatggtatac tgggagcata tggagccgat cttaaaagaa 1140
ttcgttgagc actttgaaga cctcaagaag aacagtaagg gagcgaagcg cacctttgca 1200
aagcttatcc agaatagctt gtacgggaag ttcggcatga accgcgttcg tgtgtcgttg 1260
ggtgacatgg aagaccgtta cgacttgcat gagaagcaga ttccatataa agaattcaaa 1320
catgattgta atggcttgac gcttgagttc atccaatata tctcggaaag caaagcgagc 1380
tatattcaac cgcacattgc tacatacgta acagcctatg ctcgtatcct gttgtttcgt 1440
ggtctgaaag aacaggctag caagggcgta ctgggctatt gcgatactga ctctattgcc 1500
ggtaccgcca aaatgccgga cgaaatgatc catgacgaag attacggcaa gtgggccttg 1560
gaaggtgagc tggaagaagg tatctttctc cagccgaagt tttacgcgga acgttacacg 1620
aacggcaaag aagtaattaa ggccaagggg attccacgcg agaagatgga agagttaagt 1680
ttcgagaact ataaagagtg gctcgagatt atgaaagaag ccaacaaga gcgcatcgac 1740
atctttgaag gttacgagag tcgcaagaag tttagcacca cactcaaggc cagtgaagat 1800
ttcgacacgt tgcgtgagat gaagaagtct atcaatttac tgctcgagca gaagcgcgac 1860
atcgactaca agggcaacgt gacacgtcca cataagcgct atgactacgg tggtggctca 1920
```

```
catcaccacc atcatcattc agaagaggac gaagagaaag aagaggacgg gt            1972

SEQ ID NO: 21          moltype = DNA   length = 1911
FEATURE                Location/Qualifiers
misc_feature           1..1911
                       note = APolTr (nt)
source                 1..1911
                       mol_type = other DNA
                       organism = Synthetic construct
SEQUENCE: 21
ggctccaata agcaaaagaa agagcgccaa aagccggcca agcttctcac cttggacact     60
gagacgcgcg gcctcaccgg taatgtgttc cgcgttggcc tgtttgacgg gacgaattat    120
tacaagtcga atacattcga cgagatcctt gacctgttcg agcaatataa agattacgaa    180
tgtcatgtat acgtacacaa tttagacttc gacttggcga aaatcgccac cactttgttc    240
aagcgcgacc gtgtgcgctt tgcgaagagc atcttcatta acggtaacgt agtgactttg    300
cattcggact cgatgatctt acatgatagc ttacgcttac tgccggggtc tctggaaaag    360
ctctgtaaag atttttggcc tgaccgacaa cgccaagaaa atctttccga agtcatcaaa    420
gagcagggtt acgcagtata caagaaagac ggtgtcacat tgacaagaa gaaatccctt    480
ggcaattatt ttgagaacgt gcctgccgac gaccctacgc tcaatgagta cttggagttc    540
gattgtcgca gcctgtacga gattttgacg attgtgatgg acatcgcaaa tattggcctg    600
gaaacccttag taatgtgccc gaccacgcg agcttagcca tgcgtgtcta taagagcaa    660
taccgcgagc aatatgataa ggtggccact cactttttca gtcgtgtgga gggtcaattc    720
ctcgaagagc acgttcgcca atcgtactac ggtggtcgca ctgaggtatt tacccctcat    780
ttaccacatg gttaccatta cgatgttaac tcgttgtacc cgtatgtcat gaaaattgca    840
aagttccgg tagggtaccc aaattattg aaagacggcc aggcagctac caagtggaag    900
cattggaagc gtcgtgcgat cgggggcggt gtttatgtgg gtcgtgtgga cgttccgtga    960
gacatgtaca tcccagtgct cccgaagcgt gaccccgagc ggaagttatt gttcccggtt    1020
ggtaagctcg agggagtgtg gaccctgcct gagctcctgg aagcggaaaa gaatggctgt    1080
acgatcgagg cgatttacca gatggtatac tgggagcata tggagccgat ctttaaagaa    1140
ttcgttgagc actttgaaga cctcaagaag aacagtaagg gacgaagcg cacctttgca    1200
aagcttatcc agaatagctt gtacgggaag ttcggcatga accgcgttcg tgtgtcgttg    1260
ggtgacatgg aagaccgtta cgacttgcat gagaagcaga ttccatataa agaattcaaa    1320
catgattgta atggcttgac gcttgagttc atccaatata tctcggaaag caaagcgagc    1380
tatattcaac cgcacattgc tacatacgta acagcctatc ctcgtatcct gttgtttcgt    1440
ggtctgaaag aacaggctag caagggcgta ctgggctatt gcgatactga ctctattgcc    1500
ggtaccgcca aaatgccgga cgaaatgatc catgacgaag attacggcaa gtgggccttg    1560
gaaggtgagc tggaagaagg tatctttctc cagccgaagt tttacgcgga acgttacacg    1620
aacggcaaag aagtaattaa ggccaagggg attccacgcg agaagatgga agagttaagt    1680
ttcgagaact ataaagaagtg gctcgagatt atgaaagaag gccaacaaga gcgcatcgac    1740
atctttgaag gttacgagag tcgcaagaag tttagcacca cactcaaggc cagtgaagat    1800
ttcgacacgt gcgtgagat gaagaagtct atcaatttac tgctcgagca gaagcgcgac    1860
atcgactaca agggcaacgt gacacgtcca cataagcgct atgactacgg t              1911

SEQ ID NO: 22          moltype = DNA   length = 1722
FEATURE                Location/Qualifiers
misc_feature           1..1722
                       note = Phi29 WT (nt)
source                 1..1722
                       mol_type = other DNA
                       organism = Synthetic construct
SEQUENCE: 22
aagcacatgc cacgtaaaat gtatagctgt gattttgaga ctacgacgaa agttgaagat     60
tgccgtgtgt gggcgtatgg ttacatgaat attgaagatc actccgagta taagattggc    120
aatagcctgg atgaattcat ggcgtgggtg ctgaaggttc aggccgattt gtactttcat    180
aatctgaaat ttgatggcgc tttttatcatt aactggctgg agcgtaatgg tttcaagttg    240
agcgcagatg gcctgccgaa tacgtacaac accattatca gccgtatggg ccagtggtac    300
atgatcgaca tctgcctggg ctataagggt aagcgtaaga tccacaccgt gatttatgac    360
tcctgaaaa agctgccgtt tccggtgaag aaaattgcca aagacttcaa gctgacggtt    420
ctgaagggcg acatcgatta tcacaaggaa cgtccggttg gttacaagat cacccccggaa    480
gaatacgcgt acatcaaaaa cgacattcaa atcatcgcag aggccttgct gattcagttc    540
aagcaaggtc tggaccgcat gactgccggt agcgattccc tgaagggttt caaagacatt    600
atcaccacca aaaagttcaa aaaagtgttc ccgacgctga gcctgggtct ggataaagag    660
gtccgttacg cttatcgtgg cggcttcacc tggttgaacg atcgtttcaa agaaaaagaa    720
attggtgagg gcatggtttt tgatgttaac tcactgtacc cggcacaaat gtatagccgt    780
ctgctgccgt atggcgagcc gatcgtgttc gagggtaaat acgtgtggga cgaagattac    840
ccgctgcata ttcaacatat ccgctgcgag ttcgagctga aggaaggcta catcccgacc    900
attcagatta agcgtagccg tttttacaaa ggtaatgaat acttgaagtc ctcgggcggt    960
gagattgcgg atctgtggtt aagcaacgtc gaccttgagc tgatgaaaga gcactatgac    1020
ctctataacg ttgagtacat tagcggtctg aaattccaaa ccacgacggg tctgttttaaa    1080
gacttcattg acaagtggac ctatatcaag acgacgagcg agggcgcgat caaacagctg    1140
gcgaagctga tgctgaattc tctgtacggt aagtttgcta gcaatccaga tgtcaccggc    1200
aaagtgccgt atctgaaaga aaacggtgcg ttgggttttc gctgggtga agaggaaacc    1260
aaagatccgg tgtacacccc gatgggcgtt ttcattaccg cgtgggctcg ttacaccacg    1320
attaccgcag gcaggcatg ttatgaccgt atcatttact gtgatacgga tagcattcac    1380
ttgaccggta ccgagatccc agatgtcatc aaagatattg tcgacccgaa gaaactgggt    1440
tactgggccc acgaaagcac tttcaaacgc gcaaagtatc tgcgtcagaa aacgtacatc    1500
caagacattt acatgaaaga ggttgacggc aaattggtcg agggtcgcc ggacgactac    1560
accgacatca agttcagcgt gaagtgcgcg ggtatgaccg acaaaatcaa aaaagaagtc    1620
accttttgaga actttaaggt tggttttagc cgcaagatga gcctaaaacc ggttcaggtc    1680
```

```
ccgggtggcg ttgtgctggt cgacgacacc tttactatca ag                        1722

SEQ ID NO: 23              moltype = DNA  length = 18
FEATURE                    Location/Qualifiers
misc_feature               1..18
                           note = 6x His tag (nt)
source                     1..18
                           mol_type = other DNA
                           organism = Synthetic construct
SEQUENCE: 23
catcaccacc atcatcat                                                   18

SEQ ID NO: 24              moltype = DNA  length = 34
FEATURE                    Location/Qualifiers
misc_feature               1..34
                           note = SET tag (nt)
source                     1..34
                           mol_type = other DNA
                           organism = Synthetic construct
SEQUENCE: 24
tcagaagagg acgaagagaa agaagaggac gggt                                 34

SEQ ID NO: 25              moltype =    length =
SEQUENCE: 25
000

SEQ ID NO: 26              moltype = AA  length = 98
FEATURE                    Location/Qualifiers
REGION                     1..98
                           note = SUMO tag (aa)
source                     1..98
                           mol_type = protein
                           organism = Synthetic construct
SEQUENCE: 26
SDSEVNQEAK PEVKPEVKPE THINLKVSDG SSEIFFKIKK TTPLRRLMEA FAKRQGKEMD      60
SLRFLYDGIR IQADQTPEDL DMEDNDIIEA HREQIGGS                              98

SEQ ID NO: 27              moltype = AA  length = 732
FEATURE                    Location/Qualifiers
REGION                     1..732
                           note = APol (aa)
source                     1..732
                           mol_type = protein
                           organism = Synthetic construct
SEQUENCE: 27
MGSNKQKKER QKPAKLLTLD TETRGLTGNV FRVGLFDGTN YYKSNTFDEI LDLFEQYKDY      60
ECHVYVHNLD FDLAKIATTL FKRDRVRFAK SIFINGNVVT LHSDSMILHD SLRLLPGSLE     120
KLCKDFGLTD NAKKDLSEVI KEQGYAVYKK DGVTFDKKKS LGNYFENVPA DDPTLNEYLE     180
FDCRSLYEIL TIVMDIANIG LETLVMCPTT ASLAMRVYKE QYREQYDKVA THFYMGEWGQ     240
FLEEHVRQSY YGGRTEVFTP HLPHGYHYDV NSLYPYVMKI AKFPVGYPNL LKDGQAATKW     300
KHWKRRAIGG GVMWCRVDVP EDMYIPVLPK RDPSGKLLFP VGKLEGVWTL PELLEAEKNG     360
CTIEAIYQMV YWEHMEPIFK EFVEHFEDLK KNSKGAKRTF AKLIQNSLYG KFGMNRVRVS     420
LGDMEDRYDL HEKQIPYKEF KHDCNGLTLE FIQYISESKA SYIQPHIATY VTAYARILLF     480
RGLKEQASKG VLGYCDTDSI AGTAKMPDEM IHDEDYGKWA LEGELEEGIF LQPKFYAERY     540
TNGKEVIKAK GIPREKMEEL SFENYKEWLE IMKEGQQERI DIFEGYESRK KFSTTLKASE     600
DFDTLREMKK SINLLLEQKR DIDYKGNVTR PHKRYDYGDK KDKIDYEDYK SREDKLNNMY     660
DDVDDLKEQV DEIGYIKCMK QGDMYFEEYK HLTKSVKSKY FRRTGTPIDV WANESGWDVN     720
ELLEELRLMG VC                                                        732

SEQ ID NO: 28              moltype = AA  length = 741
FEATURE                    Location/Qualifiers
REGION                     1..741
                           note = APol-His (aa)
source                     1..741
                           mol_type = protein
                           organism = Synthetic construct
SEQUENCE: 28
MGSNKQKKER QKPAKLLTLD TETRGLTGNV FRVGLFDGTN YYKSNTFDEI LDLFEQYKDY      60
ECHVYVHNLD FDLAKIATTL FKRDRVRFAK SIFINGNVVT LHSDSMILHD SLRLLPGSLE     120
KLCKDFGLTD NAKKDLSEVI KEQGYAVYKK DGVTFDKKKS LGNYFENVPA DDPTLNEYLE     180
FDCRSLYEIL TIVMDIANIG LETLVMCPTT ASLAMRVYKE QYREQYDKVA THFYMGEWGQ     240
FLEEHVRQSY YGGRTEVFTP HLPHGYHYDV NSLYPYVMKI AKFPVGYPNL LKDGQAATKW     300
KHWKRRAIGG GVMWCRVDVP EDMYIPVLPK RDPSGKLLFP VGKLEGVWTL PELLEAEKNG     360
CTIEAIYQMV YWEHMEPIFK EFVEHFEDLK KNSKGAKRTF AKLIQNSLYG KFGMNRVRVS     420
LGDMEDRYDL HEKQIPYKEF KHDCNGLTLE FIQYISESKA SYIQPHIATY VTAYARILLF     480
RGLKEQASKG VLGYCDTDSI AGTAKMPDEM IHDEDYGKWA LEGELEEGIF LQPKFYAERY     540
TNGKEVIKAK GIPREKMEEL SFENYKEWLE IMKEGQQERI DIFEGYESRK KFSTTLKASE     600
DFDTLREMKK SINLLLEQKR DIDYKGNVTR PHKRYDYGDK KDKIDYEDYK SREDKLNNMY     660
DDVDDLKEQV DEIGYIKCMK QGDMYFEEYK HLTKSVKSKY FRRTGTPIDV WANESGWDVN     720
```

```
ELLEELRLMG VCGGSHHHHH H                                               741

SEQ ID NO: 29           moltype = AA  length = 647
FEATURE                 Location/Qualifiers
REGION                  1..647
                        note = APolTr-His (aa)
source                  1..647
                        mol_type = protein
                        organism = Synthetic construct
SEQUENCE: 29
MGSNKQKKER QKPAKLLTLD TETRGLTGNV FRVGLFDGTN YYKSNTFDEI LDLFEQYKDY     60
ECHVYVHNLD FDLAKIATTL FKRDRVRFAK SIFINGNVVT LHSDSMILHD SLRLLPGSLE    120
KLCKDFGLTD NAKKDLSEVI KEQGYAVYKK DGVTFDKKKS LGNYFENVPA DDPTLNEYLE    180
FDCRSLYEIL TIVMDIANIG LETLVMCPTT ASLAMRVYKE QYREQYDKVA THFYMGEWGQ    240
FLEEHVRQSY YGGRTEVFTP HLPHGYHYDV NSLYPYVMKI AKFPVGYPNL LKDGQAATKW    300
KHWKRRAIGG GVMWCRVDVP EDMYIPVLPK RDPSGKLLFP VGKLEGVWTL PELLEAEKNG    360
CTIEAIYQMV YWEHMEPIFK EFVEHFEDLK KNSKGAKRTF AKLIQNSLYG KFGMNRVRVS    420
LGDMEDRYDL HEKQIPYKEF KHDCNGLTLE FIQYISESKA SYIQPHIATY VTAYARILLF    480
RGLKEQASKG VLGYCDTDSI AGTAKMPDEM IHDEDYGKWA LEGELEEGIF LQPKFYAERY    540
TNGKEVIKAK GIPREKMEEL SFENYKEWLE IMKEGQQERI DIFEGYESRK KFSTTLKASE    600
DFDTLREMKK SINLLLEQKR DIDYKGNVTR PHKRYDYGGG SHHHHHH                  647

SEQ ID NO: 30           moltype = AA  length = 658
FEATURE                 Location/Qualifiers
REGION                  1..658
                        note = APolTr-His-SET (aa)
source                  1..658
                        mol_type = protein
                        organism = Synthetic construct
SEQUENCE: 30
MGSNKQKKER QKPAKLLTLD TETRGLTGNV FRVGLFDGTN YYKSNTFDEI LDLFEQYKDY     60
ECHVYVHNLD FDLAKIATTL FKRDRVRFAK SIFINGNVVT LHSDSMILHD SLRLLPGSLE    120
KLCKDFGLTD NAKKDLSEVI KEQGYAVYKK DGVTFDKKKS LGNYFENVPA DDPTLNEYLE    180
FDCRSLYEIL TIVMDIANIG LETLVMCPTT ASLAMRVYKE QYREQYDKVA THFYMGEWGQ    240
FLEEHVRQSY YGGRTEVFTP HLPHGYHYDV NSLYPYVMKI AKFPVGYPNL LKDGQAATKW    300
KHWKRRAIGG GVMWCRVDVP EDMYIPVLPK RDPSGKLLFP VGKLEGVWTL PELLEAEKNG    360
CTIEAIYQMV YWEHMEPIFK EFVEHFEDLK KNSKGAKRTF AKLIQNSLYG KFGMNRVRVS    420
LGDMEDRYDL HEKQIPYKEF KHDCNGLTLE FIQYISESKA SYIQPHIATY VTAYARILLF    480
RGLKEQASKG VLGYCDTDSI AGTAKMPDEM IHDEDYGKWA LEGELEEGIF LQPKFYAERY    540
TNGKEVIKAK GIPREKMEEL SFENYKEWLE IMKEGQQERI DIFEGYESRK KFSTTLKASE    600
DFDTLREMKK SINLLLEQKR DIDYKGNVTR PHKRYDYGGG SHHHHHHSEE DEEKEEDG     658

SEQ ID NO: 31           moltype = AA  length = 575
FEATURE                 Location/Qualifiers
REGION                  1..575
                        note = Phi29 WT (aa)
source                  1..575
                        mol_type = protein
                        organism = Synthetic construct
SEQUENCE: 31
MKHMPRKMYS CDFETTTKVE DCRVWAYGYM NIEDHSEYKI GNSLDEFMAW VLKVQADLYF     60
HNLKFDGAFI INWLERNGFK WSADGLPNTY NTIISRMGQW YMIDICLGYK GKRKIHTVIY    120
DSLKKLPFPV KKIAKDFKLT VLKGDIDYHK ERPVGYKITP EEYAYIKNDI QIIAEALLIQ    180
FKQGLDRMTA GSDSLKGFKD IITTKKFKKV FPTLSLGLDK EVRYAYRGGF TWLNDRFKEK    240
EIGEGMVFDV NSLYPAQMYS RLLPYGEPIV FEGKYVWDED YPLHIQHIRC EFELKEGYIP    300
TIQIKRSRFY KGNEYLKSSG GEIADLWLSN VDLELMKEHY DLYNVEYISG LKFKATTGLF    360
KDFIDKWTYI KTTSEGAIKQ LAKLMLNSLY GKFASNPDVT GKVPYLKENG ALGFRLGEEE    420
TKDPVYTPMG VFITAWARYT TITAAQACYD RIIYCDTDSI HLTGTEIPDV IKDIVDPKKL    480
GYWAHESTFK RAKYLRQKTY IQDIYMKEVD GKLVEGSPDD YTDIKFSVKC AGMTDKIKKE    540
VTFENFKVGF SRKMKPKPVQ VPGGVVLVDD TFTIK                              575

SEQ ID NO: 32           moltype = AA  length = 638
FEATURE                 Location/Qualifiers
REGION                  1..638
                        note = APolTr (aa)
source                  1..638
                        mol_type = protein
                        organism = Synthetic construct
SEQUENCE: 32
MGSNKQKKER QKPAKLLTLD TETRGLTGNV FRVGLFDGTN YYKSNTFDEI LDLFEQYKDY     60
ECHVYVHNLD FDLAKIATTL FKRDRVRFAK SIFINGNVVT LHSDSMILHD SLRLLPGSLE    120
KLCKDFGLTD NAKKDLSEVI KEQGYAVYKK DGVTFDKKKS LGNYFENVPA DDPTLNEYLE    180
FDCRSLYEIL TIVMDIANIG LETLVMCPTT ASLAMRVYKE QYREQYDKVA THFYMGEWGQ    240
FLEEHVRQSY YGGRTEVFTP HLPHGYHYDV NSLYPYVMKI AKFPVGYPNL LKDGQAATKW    300
KHWKRRAIGG GVMWCRVDVP EDMYIPVLPK RDPSGKLLFP VGKLEGVWTL PELLEAEKNG    360
CTIEAIYQMV YWEHMEPIFK EFVEHFEDLK KNSKGAKRTF AKLIQNSLYG KFGMNRVRVS    420
LGDMEDRYDL HEKQIPYKEF KHDCNGLTLE FIQYISESKA SYIQPHIATY VTAYARILLF    480
RGLKEQASKG VLGYCDTDSI AGTAKMPDEM IHDEDYGKWA LEGELEEGIF LQPKFYAERY    540
TNGKEVIKAK GIPREKMEEL SFENYKEWLE IMKEGQQERI DIFEGYESRK KFSTTLKASE    600
```

DFDTLREMKK SINLLLEQKR DIDYKGNVTR PHKRYDYG                                638

SEQ ID NO: 33          moltype = AA   length = 2196
FEATURE                Location/Qualifiers
REGION                 1..2196
                       note = APol (nt)
source                 1..2196
                       mol_type = protein
                       organism = Synthetic construct
SEQUENCE: 33
ATGGGCTCCA ATAAGCAAAA GAAAGAGCGC CAAAAGCCGG CCAAGCTTCT CACCTTGGAC   60
ACTGAGACGC GCGGCCTCAC CGGTAATGTG TTCCGCGTTG GCCTGTTTGA CGGGACGAAT   120
TATTACAAGT CGAATACATT CGACGAGATC CTTGACCTGT TCGAGCAATA TAAAGATTAC   180
GAATGTCATG TATACGTACA CAATTTAGAC TTCGACTTGG CGAAAATCGC CACCACTTTG   240
TTCAAGCGCG ACCGTGTGCG CTTTGCGAAG AGCATCTTCA TTAACGGTAA CGTAGTGACT   300
TTGCATTCGG ACTCGATGAT CTTACATGAT AGCTTACGCT TACTGCCGGG GTCTCTGGAA   360
AAGCTCTGTA AAGATTTTGG CCTGACCGAC AACGCCAAGA AAGATCTTTC CGAAGTCATC   420
AAAGAGCAGG GTTACGCAGT ATACAAGAAA GACGGTGTCA CATTTGACAA GAAGAAATCC   480
CTTGGCAATT ATTTTGAGAA CGTGCCTGCC GACGACCCTA CGCTCAATGA GTACTTGGAG   540
TTCGATTGTC GCAGCCTGTA CGAGATTTTG ACGATTGTGA TGGACATCGC AAATATTGGC   600
CTGGAAACCT TAGTAATGTG CCCGACCACA GCGAGCTTAG CCATGCGTGT CTATAAAGAG   660
CAATACCGCG AGCAATATGA TAAGGTGGCC ACTCACTTTT ATATGGGCGA GTGGGGTCAA   720
TTCCTCGAAG AGCACGTTCG CCAATCGTAC TACGGTGGTC GCACTGAGGT ATTTACCCCT   780
CATTTACCAC ATGGTTACCA TTCGATGTT AACTCGTTGT ACCCGTATGT CATGAAAATT     840
GCAAAGTTCC CGGTAGGGTA CCCAAATTTA TTGAAAGACG GCCAGGCAGC TACCAAGTGG   900
AAGCATTGGA AGCGTCGTGC GATCGGGGGC GGTGTTATGT GGTGTCGTGT GGACGTTCCT   960
GAAGACATGT ACATCCCAGT GCTCCCGAAG CGTGACCCGA GCGGGAAGTT ATTGTTCCCG  1020
GTTGGTAAGC TCGAGGGAGT GTGGACCCTG CCTGAGCTCC TGGAAGCGGA AAAGAATGGC  1080
TGTACGATCG AGGCGATTTA CCAGATGGTA TACTGGGAGC ATATGGAGCC GATCTTTAAA  1140
GAATTCGTTG AGCACTTTGA AGACCTCAAG AAGAACAGTA AGGGAGCGAA GCGCACCTTT  1200
GCAAAGCTTA TCCAGAATAG CTTGTACGGG AAGTTCGGCA TGAACCGCGT TCGTGTGTCG  1260
TTGGGTGACA TGGAAGACCG TTACGACTTG CATGAGAAGC AGATTCCATA TAAGAATTC   1320
AAACATGATT GTAATGGCTT GACGCTTGAG TTCATCCAAT ATATCTCGGA AAGCAAAGCG  1380
AGCTATATTC AACCGCACAT TGCTACATAC GTAACGATCT ATGCTCGTAT CCTGTTGTTT  1440
CGTGGTCTGA AGAACAGGC TAGCAAGGGC GTACTGGGCT ATTGCGATAC TGACTCTATT    1500
GCCGGTACCG CCAAAATGCC GGACGAAATG ATCCATGACG AAGATTCAGG CAAGTGGGCC  1560
TTGGAAGGTG AGCTGGAAGA AGGTATCTTT CTCCAGCCGA AGTTTTACGC GGAACGTTAC  1620
ACGAACGGCA AAGAAGTAAT TAAGGCCAAG GGGATTCCAC GCGAGAAGAT GGAAGAGTTA  1680
AGTTTCGAGA ACTATAAAGA GTGGCTCAGA ATTATGAAAG AAGGCCAACA AGAGCGCATC  1740
GACATCTTTG AAGGTTACGA GAGTCGCAAG AAGTTTAGCA CCACACTCAA GGCCAGTGAA  1800
GATTTCGACA CGTTGCGTGA CATGAAGAAG TCTATCAATT TACTGCTCGA GCAGAAGCGC  1860
GACATCGACT ACAAGGGCAA CGTGACACGT CCACATAAGC GCTATGACTA CGGTGATAAG  1920
AAAGACAAGA TCGATTATGA AGACTATAAG AGCGTGAAG ACAAGTTAAA CAACATGTAC    1980
GACGATGTAG ACGACTTAAA AGAGCAAGTT GACGAGATCG GCTACATCAA GTGCATGAAG  2040
CAAGGCGATA TGTATTTTGA AGAGTACAAA CATCTTACGA AGTCTGTGAA AGTAAGTAT   2100
TTCCGCCGCA CTGGCACCCC AATCGACGTA TGGGCGAACA AATCCGGTTG GGACGTAAAC  2160
GAGTTATTAG AAGAGCTTCG TCTGATGGGC GTGTGC                            2196

SEQ ID NO: 34          moltype = DNA   length = 2223
FEATURE                Location/Qualifiers
misc_feature           1..2223
                       note = APol-His (nt)
source                 1..2223
                       mol_type = other DNA
                       organism = Synthetic construct
SEQUENCE: 34
atgggctcca ataagcaaaa gaaagagcgc caaaagccgg ccaagcttct caccttggac   60
actgagacgc gcggcctcac cggtaatgtg ttccgcgttg gcctgtttga cgggacgaat   120
tattacaagt cgaatacatt cgacgagatc cttgacctgt tcgagcaata taaagattac   180
gaatgtcatg tatacgtaca catttagac ttcgacttgg cgaaaatcgc caccactttg    240
ttcaagcgcg accgtgtgcg ctttgcgaag agcatcttca ttaacggtaa cgtagtgact   300
ttgcattcgg actcgatgat cttacatgat agcttacgct tactgccggg gtctctggaa   360
aagctctgta aagattttgg cctgaccgac aacgccaaga aagatctttc cgaagtcatc   420
aaagagcagg gttacgcagt atacaagaaa gacggtgtca catttgacaa gaagaaatcc   480
cttggcaatt attttgagaa cgtgcctgcc gacgacccta cgctcaatga gtacttggag   540
ttcgattgtc gcagcctgta cgagattttg acgattgtga tggacatcgc aaatattggc   600
ctggaaacct tagtaatgtg cccgaccaca gcgagcttag ccatgcgtgt ctataaagag   660
caataccgcg agcaatatga taaggtggcc actcactttt atatgggcga gtggggtcaa   720
ttcctcgaag agcacgttcg ccaatcgtac tacggtggtc gcactgaggt atttacccct   780
catttaccac atggttacca ttcgatgtt aactcgttgt acccgtatgt catgaaaatt    840
gcaaagttcc cggtagggta cccaaattta ttgaaagacg gccaggcagc taccaagtgg   900
aagcattgga agcgtcgtgc gatcggggc ggtgttatgt ggtgtcgtgt ggacgttcct    960
gaagacatgt acatcccagt gctcccgaag cgtgacccga gcgggaagtt attgttcccg  1020
gttggtaagc tcgagggagt gtggaccctg cctgagctcc tggaagcgga aaagaatggc  1080
tgtacgatcg aggcgattta ccagatggta tactgggagc atatggagcc gatctttaaa  1140
gaattcgttg agcactttga agacctcaag aagaacagta agggagcgaa gcgcaccttt  1200
gcaaagctta tccagaatag cttgtacggg aagttcggca tgaaccgcgt tcgtgtgtcg  1260
ttgggtgaca tggaagaccg ttacgacttg catgagaagc agattccata taagaattc   1320
aaacatgatt gtaatggctt gacgcttgag ttcatccaat atatctcgga aagcaaagcg  1380

```
agctatattc aaccgcacat tgctacatac gtaacagcct atgctcgtat cctgttgttt    1440
cgtggtctga aagaacaggc tagcaagggc gtactgggct attgcgatac tgactctatt    1500
gccggtaccg ccaaaatgcc ggacgaaatg atccatgacg aagattacgg caagtgggcc    1560
ttggaaggtg agctggaaga aggtatcttt ctccagccga agttttacgc ggaacgttac    1620
acgaacggca aagaagtaat taaggccaag gggattccac gcgagaagat ggaagagtta    1680
agtttcgaga actataaaga gtggctcgag attatgaaag aaggccaaca agagcgcatc    1740
gacatctttg aaggttacga gagtcgcaag aagtttagca ccacactcaa ggccagtgaa    1800
gatttcgaca cgttgcgtga gatgaagaag tctatcaatt tactgctcga gcagaagcgc    1860
gacatcgact acaagggcaa cgtgacacgt ccacataagc gctatgacta cggtgataag    1920
aaagacaaga tcgattatga agactataag agccgtgaag acaagttaaa caacatgtac    1980
gacgatgtag acgacttaaa agagcaagtt gacgagatcg gctacatcaa gtgcatgaag    2040
caaggcgata tgtattttga agagtacaaa catcttacga agtctgtgaa aagtaagtat    2100
ttccgccgca ctggcacccc aatcgacgta tgggcgaacg aatccggttg ggacgtaaac    2160
gagttattag aagagcttcg tctgatgggc gtgtgcggtg gctcacatca ccaccatcat    2220
cat                                                                  2223

SEQ ID NO: 35           moltype = DNA   length = 1941
FEATURE                 Location/Qualifiers
misc_feature            1..1941
                        note = APolTr-His (nt)
source                  1..1941
                        mol_type = other DNA
                        organism = Synthetic construct
SEQUENCE: 35
atgggctcca ataagcaaaa gaaagagcgc caaaagccgg ccaagcttct caccttggac      60
actgagacgc gcggcctcac cggtaatgtg ttccgcgttg gcctgtttga cgggacgaat     120
tattacaagt cgaatacatt cgacgagatc cttgacctgt tcgagcaata taaagattac     180
gaatgtcatg tatacgtaca caatttagac ttcgacttgg cgaaaatcgc caccactttg     240
ttcaagcgcg accgtgtgcg ctttgcgaag agcatcttca ttaacggtaa cgtagtgact     300
ttgcattcgg actcgatgat cttacatgat agcttacgct tactgccggg tgtctctgaa     360
aagctctgta aagattttgg cctgaccgac aacgccaaga agatctttc cgaagtcatc      420
aaagagcagg ttacgcagt ataccagaaa gacggtgtca catttgacaa gaagaaatcc      480
cttggcaatt attttgagaa cgtgcctgcc gacgaccct cgctcaatga gtacttggag     540
ttcgattgtc gcagcctgta cgagattttg acgattgtga tggacatcgc aaatattggc     600
ctggaaacct tagtaatgtg cccgaccaca gcgagcttag ccatgcgtgt ctataaagag     660
caataccgcg agcaatatga taaggtggcc actcactttt atatgggcga gtggggtcaa     720
ttcctcgaag agcacgttcg ccaatcgtac tacggtggtc gcactgaggt atttaccct     780
catttaccac atggttacca ttacgatgtt aactcgttgt accgtatgt catgaaaatt      840
gcaaagttcc cggtagggta cccaaattta ttgaaagacg gccaggcag taccaagtgg     900
aagcattgga agcgtcgtgc gatcgggggc ggtgtatgt gtgtcgtgt ggacgttcct      960
gaagacatgt acatcccagt gctcccgaag cgtgacccga gcgggaagtt attgttcccg    1020
gttggtaagc tcgaggagt gtggaccctg cctgagctcc tggaagcgga aaagaatggc    1080
tgtacgatcg aggcgattta ccagatgatg tactgggagc atgtcgaagtg gatctttaaa    1140
gaattcgttg agcactttga agacctcaag aagaacagta agggagcgaa gcgcaccttt    1200
gcaaagctta tccagaatag cttgtacggg aagttcggca tgaaccgcgt tcgtgtgtcg    1260
ttgggtgaca tggaagaccg ttacgacttg catgagaagc agattccata taagaattc    1320
aaacatgatt gtaatggctt gacgcttgag ttcatccaat atatctcgga aagcaaagcg    1380
agctatattc aaccgcacat tgctacatac gtaacagcct atgctcgtat cctgttgttt    1440
cgtggtctga aagaacaggc tagcaagggc gtactgggct attgcgatac tgactctatt    1500
gccggtaccg ccaaaatgcc ggacgaaatg atccatgacg aagattacgg caagtgggcc    1560
ttggaaggtg agctggaaga aggtatcttt ctccagccga agttttacgc ggaacgttac    1620
acgaacggca aagaagtaat taaggccaag gggattccac gcgagaagat ggaagagtta    1680
agtttcgaga actataaaga gtggctcgag attatgaaag aaggccaaca agagcgcatc    1740
gacatctttg aaggttacga gagtcgcaag aagtttagca ccacactcaa ggccagtgaa    1800
gatttcgaca cgttgcgtga gatgaagaag tctatcaatt tactgctcga gcagaagcgc    1860
gacatcgact acaagggcaa cgtgacacgt ccacataagc gctatgacta cggtggtggc    1920
tcacatcacc accatcatca t                                              1941

SEQ ID NO: 36           moltype = DNA   length = 1975
FEATURE                 Location/Qualifiers
misc_feature            1..1975
                        note = APolTr-His-SET (nt)
source                  1..1975
                        mol_type = other DNA
                        organism = Synthetic construct
SEQUENCE: 36
atgggctcca ataagcaaaa gaaagagcgc caaaagccgg ccaagcttct caccttggac      60
actgagacgc gcggcctcac cggtaatgtg ttccgcgttg gcctgtttga cgggacgaat     120
tattacaagt cgaatacatt cgacgagatc cttgacctgt tcgagcaata taaagattac     180
gaatgtcatg tatacgtaca caatttagac ttcgacttgg cgaaaatcgc caccactttg     240
ttcaagcgcg accgtgtgcg ctttgcgaag agcatcttca ttaacggtaa cgtagtgact     300
ttgcattcgg actcgatgat cttacatgat agcttacgct tactgccggg tgtctctgaa     360
aagctctgta aagattttgg cctgaccgac aacgccaaga agatctttc cgaagtcatc      420
aaagagcagg ttacgcagt ataccagaaa gacggtgtca catttgacaa gaagaaatcc      480
cttggcaatt attttgagaa cgtgcctgcc gacgaccct cgctcaatga gtacttggag     540
ttcgattgtc gcagcctgta cgagattttg acgattgtga tggacatcgc aaatattggc     600
ctggaaacct tagtaatgtg cccgaccaca gcgagcttag ccatgcgtgt ctataaagag     660
caataccgcg agcaatatga taaggtggcc actcactttt atatgggcga gtggggtcaa     720
ttcctcgaag agcacgttcg ccaatcgtac tacggtggtc gcactgaggt atttaccct     780
```

```
catttaccac atggttacca ttacgatgtt aactcgttgt acccgtatgt catgaaaatt    840
gcaaagttcc cggtagggta cccaaattta ttgaaagacg gccaggcagc taccaagtgg    900
aagcattgga agcgtcgtgc gatcgggggc ggtgttatgt ggtgtcgtgt ggacgttcct    960
gaagacatgt acatcccagt gctcccgaag cgtgacccga gcgggaagtt attgttcccg   1020
gttgtaagc tcgagggagt gtggaccctg cctgagctcc tggaagcgaa aaagaatggc    1080
tgtacgatcg aggcgattta ccagatggta tactgggagc atatggagcc gatctttaaa   1140
gaattcgttg agcactttga agacctcaag aagaacagta agggagcgaa gcgcaccttt   1200
gcaaagctta tccagaatag cttgtacggg aagttcggca tgaaccgcgt tcgtgtgtcg   1260
ttgggtgaca tggaagaccg ttacgacttg catgagaagc agattccata taaagaattc   1320
aaacatgatt gtaatggctt gacgcttgag ttcatccaat atatctcgga aagcaaagcg   1380
agctatattc aaccgcacat tgctacatac gtaacagcct atgctcgtat cctgttgttt   1440
cgtggtctga aagaacaggc tagcaagggc gtactgggct attgcgatac tgactctatt   1500
gccggtaccg ccaaaatgcc ggacgaaatg atccatgacg aagattacgg caagtgggcc   1560
ttggaaggtg agctggaaga aggtatcttt ctccagccga agttttacgc ggaacgttac   1620
acgaacggca aagaagtaat taaggccaag gggattccac gcgagaagat ggaagagtta   1680
agtttcgaga actataaaga gtggctcgag attatgaaag aaggccaaca agagcgcatc   1740
gacatctttg aaggttacga gagtcgcaag aagtttagca ccacactcaa ggccagtgaa   1800
gatttcgaca cgttgcgtga gatgaagaag tctatcaatt tactgctcga gcagaagcgc   1860
gacatcgact acaagggcaa cgtgacacgt ccacataagc gctatgacta cggtggtggc   1920
tcacatcacc accatcatca ttcagaagag gacgaagaga agaagaggac cgggt         1975

SEQ ID NO: 37         moltype = DNA  length = 1914
FEATURE               Location/Qualifiers
misc_feature          1..1914
                      note = APolTr (nt)
source                1..1914
                      mol_type = other DNA
                      organism = Synthetic construct
SEQUENCE: 37
atgggctcca ataagcaaaa gaaagagcgc caaaagccgg ccaagcttct caccttggac     60
actgagacgc gcggcctcac cggtaatgtg ttccgcgttg gcctgtttga cgggacgaat    120
tattacaagt cgaatacatt cgacgagatc cttgacctgt tcgagcaata taagattac    180
gaatgtcatg tatacgtaca caatttagac ttcgacttgg cgaaaatcgc caccactttg    240
ttcaagcgcg accgtgtgcg cttttgcgaag agcatcttca ttaacggtaa cgtagtgact    300
ttgcattcgg actcgatgat cttacatgat agcttacgct tactgccggg gtctctggaa    360
aagctctgta agatttttgg cctgaccgac aacgccaaga aagatctttc cgaagtcatc    420
aaagagcagg gttacgcagt atacaagaaa gacggtgtca catttgacaa gaagaaatcc    480
cttggcaatt atttttgagaa cgtgcctgcc gacgacccta cgctcaatga gtacttggag    540
ttcgattgtc gcagcctgta cgagattttg acgattgtga ttggacatcgc aaatattggc    600
ctggaaacct tagtaatgtg cccgaccaca gcgagcttag ccatgcgtgt ctataaagag    660
caataccgcg agcaatatga taaggtggcc actcacttt atatgggcga gtgggtcaa     720
ttcctcgaag agcacgttcg ccaatcgtac tacggtggtc gcactgaggt atttacccct    780
catttaccac atggttacca ttacgatgtt aactcgttgt acccgtatgt catgaaaatt    840
gcaaagttcc cggtagggta cccaaattta ttgaaagacg gccaggcagc taccaagtgg    900
aagcattgga agcgtcgtgc gatcgggggc ggtgttatgt ggtgtcgtgt ggacgttcct    960
gaagacatgt acatcccagt gctcccgaag cgtgacccga gcgggaagtt attgttcccg   1020
gttgtaagc tcgagggagt gtggaccctg cctgagctcc tggaagcgaa aaagaatggc    1080
tgtacgatcg aggcgattta ccagatggta tactgggagc atatggagcc gatctttaaa   1140
gaattcgttg agcactttga agacctcaag aagaacagta agggagcgaa gcgcaccttt   1200
gcaaagctta tccagaatag cttgtacggg aagttcggca tgaaccgcgt tcgtgtgtcg   1260
ttgggtgaca tggaagaccg ttacgacttg catgagaagc agattccata taaagaattc   1320
aaacatgatt gtaatggctt gacgcttgag ttcatccaat atatctcgga aagcaaagcg   1380
agctatattc aaccgcacat tgctacatac gtaacagcct atgctcgtat cctgttgttt   1440
cgtggtctga aagaacaggc tagcaagggc gtactgggct attgcgatac tgactctatt   1500
gccggtaccg ccaaaatgcc ggacgaaatg atccatgacg aagattacgg caagtgggcc   1560
ttggaaggtg agctggaaga aggtatcttt ctccagccga agttttacgc ggaacgttac   1620
acgaacggca aagaagtaat taaggccaag gggattccac gcgagaagat ggaagagtta   1680
agtttcgaga actataaaga gtggctcgag attatgaaag aaggccaaca agagcgcatc   1740
gacatctttg aaggttacga gagtcgcaag aagtttagca ccacactcaa ggccagtgaa   1800
gatttcgaca cgttgcgtga gatgaagaag tctatcaatt tactgctcga gcagaagcgc   1860
gacatcgact acaagggcaa cgtgacacgt ccacataagc gctatgacta cggt         1914

SEQ ID NO: 38         moltype = DNA  length = 1725
FEATURE               Location/Qualifiers
misc_feature          1..1725
                      note = Phi29 WT (nt)
source                1..1725
                      mol_type = other DNA
                      organism = Synthetic construct
SEQUENCE: 38
atgaagcaca tgccacgtaa aatgtatagc tgtgatttg agactacgac gaaagttgaa      60
gattgccgtg tgtgggcgta tggttacatg aatattgaag atcactccga gtataagatt    120
ggcaatagcc tggatgaatt catggcgtgg gtgctgaagg ttcaggccga tttgtacttt    180
cataatctga aatttgatgg cgcttttatc attaactgtc ggagcgtaa tggttttcaag    240
tggagcgcag atggcctgcc gaatacgtac aacaccatta tcagccgtat gggccagtgg    300
tacatgatcg acatctgcct gggctataag ggtaagcgta agatccacac cgtgatttat    360
gactccctga aaaagctgcc gtttccggta agaaaattg ccaaagactt caagctgacg    420
gttctgaagg gcgacatcga ttatcacaag gaacgtccgg ttggttacaa gatcacccg    480
gaagaatacg cgtacatcaa aaacgacatt caaatcatcg cagaggcctt gctgattcag    540
```

```
ttcaagcaag gtctggaccg catgactgcc ggtagcgatt ccctgaaggg tttcaaagac  600
attatcacca ccaaaaagtt caaaaaagtg ttcccgacgc tgagcctggg tctggataaa  660
gaggtccgtt acgcttatcg tggcggcttc acctggttga acgatcgttt caaagaaaaa  720
gaaattggtg agggcatggt ttttgatgtt aactcactgt acccggcaca aatgtatagc  780
cgcctgctgc cgtatggcga gccgatcgtg ttcgagggta aatacgtgtg ggacgaagat  840
tacccgctgc atattcaaca tatccgctgc gagttcgagc tgaaggaagg ctacatcccg  900
accattcaga ttaagcgtag ccgtttttac aaaggtaatg aatacttgaa gtcctcgggc  960
ggtgagattg cggatctgtg gttaagcaac gtcgaccttg agctgatgaa agagcactat 1020
gacctctata acgttgagta cattagcggt ctgaaattca aagccacgac gggtctgttt 1080
aaagacttca ttgacaagtg gacctatatc aagacgacga gcgagggcgc gatcaaacag 1140
ctggcgaagc tgatgctgaa ttctctgtac ggtaagtttg ctagcaatcc agatgtcacc 1200
ggcaaagtgc cgtatctgaa agaaaacggt gcgttgggtt ttcgcctggg tgaagaggaa 1260
accaaagatc cggtgtacac cccgatgggc gttttcatta ccgcgtgggc tcgttacacc 1320
acgattaccg cagcgcaggc atgttatgac cgtatcattt actgtgatac ggatagcatt 1380
cacttgaccg gtaccgagat cccagatgtc atcaaagata ttgtcgaccc gaagaaactg 1440
ggttactggg cccacgaaag cactttcaaa cgcgcaaagt atctgcgtca gaaaacgtac 1500
atccaagaca tttacatgaa agaggttgac ggcaaattgg tcgagggttc gccggacgac 1560
tacaccgaca tcaagttcag cgtgaagtgc gcgggtatga ccgacaaaat caaaaaagaa 1620
gtcacctttg agaactttaa ggttggtttt agccgcaaga tgaagcctaa accggttcag 1680
gtcccgggtg gcgttgtgct ggtcgacgac acctttacta tcaag            1725
```

AP50 POLYMERASES AND USES THEREOF

CROSS-REFERENCE TO RELATED APPLICATIONS

This application claims priority to U.S. Provisional Patent Application No. 63/398,507, filed Aug. 16, 2022, entitled "AP50 POLYMERASES AND USES THEREOF," which is herein incorporated by reference in its entirety for all purposes.

INCORPORATION BY REFERENCE OF SEQUENCE LISTING

The present application is being filed along with a Sequence Listing in electronic format. The Sequence Listing is provided as a file entitled 202412016000SeqList.xml, created Aug. 10, 2023, which is 78,540 bytes in size. The information in the electronic format of the Sequence Listing is incorporated by reference in its entirety.

FIELD

The present disclosure relates in some aspects to compositions and methods of using recombinant nucleic acid polymerases for DNA amplification reactions, e.g., rolling circle amplification (RCA).

BACKGROUND

Polymerases such as Phi29 DNA polymerases are used for methods of amplifying nucleic acids such as rolling circle amplification (RCA). However, Phi29 DNA polymerases have certain limitations, which restrict their utility. New and improved polymerases are needed. Provided herein are compositions and methods that address such and other needs.

SUMMARY

Provided herein are recombinant nucleic acid polymerases from a *Bacillus* phage. In some aspects, provided are recombinant *Bacillus* phage AP50 polymerases (APol), including a *Bacillus anthracis* phage AP50 polymerase or a modified AP50 polymerase. Also provided are compositions and kits comprising the recombinant AP50 polymerases and related methods and uses of the recombinant AP50 polymerases, for example, in amplifying nucleic acids, such as in rolling circle amplification (RCA) reactions, and methods for producing any of the recombinant AP50 polymerases. Also provided herein are polynucleotides encoding any of the provided recombinant AP50 polymerases, recombinant nucleic acid molecules, vectors, recombinant expression systems and kits. In some of any embodiments, the recombinant AP50 polymerases can be used to improve nucleic acid amplification, such as RCA, and result in improved analysis of biological samples, for example in vitro and in situ.

In some of any of the provided embodiments, the recombinant AP50 polymerases are modified AP50 polymerases, such as those comprise one or more amino acid deletions, insertions, substitutions, truncations, or a combination thereof. In some of any of the provided embodiments, the recombinant AP50 polymerases are isolated, recombinantly-produced wild type AP50 polymerases. In some cases, the recombinant polymerases AP50 polymerases exhibit one or more features, such as improved thermostability, processivity, sensitivity, specificity, solubility, and/or polymerization rate, for example, relative to a reference polymerase (e.g., a wild-type Phi29 polymerase). In some cases, the recombinant AP50 polymerases are thermostable, yield more amplification product, and/or can be used in wider range of nucleic acid amplification methods or samples.

Provided herein are methods for nucleic acid amplification that involves contacting a biological sample comprising a nucleic acid to be amplified with a recombinant *Bacillus* phage AP50 polymerase.

In some embodiments, the recombinant polymerase comprises a contiguous portion of SEQ ID NO:6 of at least 200 amino acids in length, or a sequence that has at least at or about 80%, 85%, 90%, 95%, 96%, 97%, 98%, 99%, or 99.5% sequence identity to any of the foregoing. In some of any embodiments, the recombinant polymerase comprises a contiguous portion of SEQ ID NO:6 of at least 600 amino acids in length, or a sequence that has at least at or about 80%, 85%, 90%, 95%, 96%, 97%, 98%, 99%, or 99.5% sequence identity to any of the foregoing. In some of any embodiments, the recombinant polymerase comprises the sequence set forth in SEQ ID NO:6 or a sequence that has at least at or about 80%, 85%, 90%, 95%, 96%, 97%, 98%, 99%, or 99.5% sequence identity to the sequence set forth in SEQ ID NO:6. In some of any embodiments, the recombinant polymerase comprises the sequence set forth in SEQ ID NO:6. In some of any embodiments, the recombinant polymerase consists of the sequence set forth in SEQ ID NO:6.

In some of any of the provided embodiments, the recombinant polymerase comprises a contiguous portion of SEQ ID NO:1 of at least 640 amino acids in length, or a sequence that has at least at or about 80%, 85%, 90%, 95%, 96%, 97%, 98%, 99%, or 99.5% sequence identity to any of the foregoing. In some of any embodiments, the recombinant polymerase comprises the sequence set forth in SEQ ID NO:1 or a sequence that has at least at or about 80%, 85%, 90%, 95%, 96%, 97%, 98%, 99%, or 99.5% sequence identity to the sequence set forth in SEQ ID NO:1. In some of any embodiments, the recombinant polymerase comprises the sequence set forth in SEQ ID NO:1. In some of any embodiments, the recombinant polymerase consists of the sequence set forth in SEQ ID NO:1.

In some of any of the provided embodiments, the recombinant polymerase comprises one or more amino acid substitutions, deletions or additions at one or more positions, corresponding to the positions of the sequence set forth in SEQ ID NO:1.

In some of any embodiments, the recombinant polymerase further comprises a heterologous sequence. In some of any embodiments, the heterologous sequence comprises one or more tags, linkers, and/or polypeptide domains.

In some of any of the provided embodiments, the heterologous sequence comprises one or more tags. In some of any embodiments, the tag is selected from among a poly histidine (HIS) tag, a solubility enhancement tag (SET), a small ubiquitin modified (SUMO) tag, a *Fasciola hepatica* 8-kDa antigen (Fh8) tag, a thioredoxin (Trx) tag, a glutathione-s-transferase (GST) tag, a maltose-binding protein (MBP) tag, an IgG domain B1 of protein G (GB1) tag, a mutated dehalogenase (Halo) tag, a streptavidin-binding peptide (SBP) tag, and a Tamavidin tag. In some of any embodiments, the tag comprises the sequence set forth in any of SEQ ID NOS:7, 8 and 26. In some of any embodiments, the tag comprises the sequence set forth in SEQ ID NO:7. In some of any embodiments, the tag comprises the sequence set forth in SEQ ID NO:8. In some of any embodiments, the tag comprises the sequence set forth in SEQ ID NO:26.

In some of any of the provided embodiments, the heterologous sequence comprises one or more polypeptide domains. In some of any embodiments, the polypeptide domain is selected from among a helix-hairpin-helix (HhH) DNA binding motif, a helix-hairpin-helix fusion [(HhH)$_2$] DNA binding motif, a single stranded DNA binding domain, an SD07 DNA binding motif, an SS07 DNA binding motif, and an E. coli HU domain.

In some of any of the provided embodiments, the heterologous sequence comprises one or more linkers. In some of any embodiments, the linker is at least at or about 1, 2, 3, 4, 5, 6, 7, 8, 9, 10, 15, 20, 25, 30, 40, or 50 amino acids in length. In some of any embodiments, the linker comprises the sequence set forth in any of SEQ ID NOS:10-16. In some of any embodiments, the recombinant polymerase comprises the sequence set forth in SEQ ID NO:6, a linker, and a poly histidine (HIS) tag.

In some of any of the provided embodiments, the recombinant polymerase comprises the sequence set forth in SEQ ID NO:6, a linker, a poly histidine (HIS) tag, and a solubility enhancement tag (SET).

In some of any embodiments, the recombinant polymerase comprises the sequence set forth in any one of SEQ ID NOS:2-4 or a sequence that has at least or about 80%, 85%, 90%, 95%, 96%, 97%, 98%, 99%, or 99.5% sequence identity to the sequence set forth in SEQ ID NOS:2-4. In some of any embodiments, the recombinant polymerase comprises the sequence set forth in SEQ ID NO:2. In some of any embodiments, the recombinant polymerase comprises the sequence set forth in SEQ ID NO:3. In some of any embodiments, the recombinant polymerase comprises the sequence set forth in SEQ ID NO:4.

In some of any of the provided embodiments, the recombinant polymerase is 900 amino acids or less in length. In some of any embodiments, recombinant polymerase is 800 amino acids or less in length. In some of any embodiments, the recombinant polymerase is 732 amino acids or less in length. In some of any embodiments, the recombinant polymerase is 638 amino acids or less in length. In some of any embodiments, the recombinant polymerase is 600 amino acids or less in length. In some of any embodiments, the recombinant polymerase is 500 amino acids or less in length.

In some of any of the provided embodiments, the nucleic acid comprises deoxyribonucleotide residues. In some of any embodiments, the nucleic acid comprises one or more ribonucleotide residues. In some of any embodiments, the nucleic acid is a circular probe or a circularizable probe.

In some of any of the provided embodiments, the nucleic acid is amplified by rolling circle amplification (RCA) using the recombinant polymerase. In some of any embodiments, the nucleic acid is amplified in situ in the biological sample using the recombinant polymerase. In some of any embodiments, the method further comprises incubating the recombinant polymerase and the biological sample with a primer that hybridizes to the nucleic acid. In some of any embodiments, the primer comprises a synthetic oligonucleotide. In some of any embodiments, the primer comprises a cellular nucleic acid or a portion thereof in the biological sample.

In some of any of the provided embodiments, the recombinant polymerase has DNA synthesis activity. In some of any embodiments, the recombinant polymerase is capable of polymerizing DNA based on circular nucleic acid templates. In some of any embodiments, the recombinant polymerase has RNA synthesis activity. In some of any embodiments, the recombinant polymerase has strand displacement activity. In some of any embodiments, the recombinant polymerase has reverse transcriptase activity. In some of any embodiments, the recombinant polymerase has exonuclease activity.

In some of any of the provided embodiments, the recombinant polymerase exhibits one or more features selected from among improved processivity, improved polymerization rate, and improved thermostability, compared to a reference polymerase. In some of any embodiments, the recombinant polymerase exhibits improved processivity compared to a reference polymerase. In some of any embodiments, the recombinant polymerase exhibits improved kinetics compared to a reference polymerase. In some of any embodiments, the recombinant polymerase exhibits improved polymerization rate compared to a reference polymerase. In some of any embodiments, the recombinant polymerase exhibits improved thermostability compared to a reference polymerase.

In some of any of the provided embodiments, the recombinant polymerase is capable of generating a rolling-circle amplification (RCA) product in an RCA reaction. In some of any embodiments, the recombinant polymerase and the biological sample are incubated at a temperature of at or about 5° C., 10° C., 15° C., 20° C., 25° C., 30° C., 35° C., 40° C., 45° C., or higher. In some of any embodiments, the RCA reaction is performed for at or about 15 minutes, 30 minutes, 45 minutes, 1 hour, 2 hours, 3 hours, 6 hours, 12 hours, or longer.

In some of any of the provided embodiments, the method further comprises detecting or analyzing an amplification product. In some of any embodiments, the amplification product is detected or analyzed by sequential hybridization, sequencing by hybridization, sequencing by ligation, sequencing by synthesis, sequencing by binding, or a combination thereof. In some of any embodiments, the nucleic acid and/or the amplification product comprises one or more barcode sequences or complements thereof. In some of any embodiments, the one or more barcode sequences or complements thereof correspond to a target nucleic acid or an endogenous analyte. In some of any embodiments, the one or more barcode sequences or complements thereof are detected by contacting the biological sample with one or more detectably-labeled probes that directly or indirectly bind to the one or more barcode sequences or complements thereof; detecting signals associated with the one or more detectably-labeled probes; and removing the one or more detectably-labeled probes. In some of any embodiments, the one or more barcode sequences or complements thereof are detected by contacting the biological sample with one or more intermediate probes that directly or indirectly bind to the one or more barcode sequences or complements thereof, wherein the one or more intermediate probes are detectable using one or more detectably-labeled probes; detecting signals associated with the one or more detectably-labeled probes; and removing the one or more intermediate probes and/or the one or more detectably-labeled probes.

In some of any of the provided embodiments, the recombinant polymerase generates a higher density of detected rolling-circle amplification (RCA) products in an RCA compared to a reference polymerase. In some of any embodiments, the recombinant polymerase generates a higher signal intensity in an RCA compared to a reference polymerase. In some of any embodiments, the RCA reaction is performed at a temperature of at or about 5° C., 10° C., 15° C., 20° C., 25° C., 30° C., 35° C., 40° C., 45° C., or higher.

In some of any of the provided embodiments, the reference polymerase is a Phi29 polymerase set forth in SEQ ID NO:5.

In some of any of the provided embodiments, the biological sample is a cell sample or a tissue sample. In some of any embodiments, the biological sample is non-homogenized. In some of any embodiments, the biological sample is selected from among a formalin-fixed, paraffin-embedded (FFPE) sample, a frozen tissue sample, and a fresh tissue sample.

Also provided are recombinant *Bacillus* phage AP50 polymerases comprising i) a contiguous portion of SEQ ID NO:6 of at least 200 amino acids in length, or a sequence that has at least at or about 80%, 85%, 90%, 95%, 96%, 97%, 98%, 99%, or 99.5% sequence identity to any of the foregoing; and ii) a heterologous sequence. In some of any of the provided embodiments, the recombinant polymerase comprises a contiguous portion of SEQ ID NO:6 of at least 600 amino acids in length, or a sequence that has at least at or about 80%, 85%, 90%, 95%, 96%, 97%, 98%, 99%, or 99.5% sequence identity to any of the foregoing.

Also provided herein are recombinant *Bacillus* phage AP50 polymerases comprising i) the sequence set forth in SEQ ID NO:6 or a sequence that has at least at or about 80%, 85%, 90%, 95%, 96%, 97%, 98%, 99%, or 99.5% sequence identity to the sequence set forth in SEQ ID NO:6; and ii) a heterologous sequence.

In some of any embodiments, the recombinant polymerase comprises the sequence set forth in SEQ ID NO:6. In some of any of the provided embodiments, the recombinant polymerase comprises a contiguous portion of SEQ ID NO:1 of at least 637 amino acids in length, or a sequence that has at least at or about 80%, 85%, 90%, 95%, 96%, 97%, 98%, 99%, or 99.5% sequence identity to any of the foregoing. In some of any embodiments, the recombinant polymerase comprises the sequence set forth in SEQ ID NO:1 or a sequence that has at least at or about 80%, 85%, 90%, 95%, 96%, 97%, 98%, 99%, or 99.5% sequence identity to the sequence set forth in SEQ ID NO:1. In some of any embodiments, the recombinant polymerase comprises the sequence set forth in SEQ ID NO:1. In some of any embodiments, the recombinant polymerase consists of the sequence set forth in SEQ ID NO:1 and the heterologous sequence.

Provided herein are recombinant *Bacillus* phage AP50 polymerases consisting of a contiguous portion of the sequence set forth in SEQ ID NO:6 of at least 200 amino acids in length, or a sequence that has at least at or about 80%, 85%, 90%, 95%, 96%, 97%, 98%, 99%, or 99.5% sequence identity to any of the foregoing. In some of any embodiments, the recombinant polymerase consists of the sequence set forth in SEQ ID NO:6 or a contiguous portion of SEQ ID NO:6 of at least 600 amino acids in length, or a sequence that has at least at or about 80%, 85%, 90%, 95%, 96%, 97%, 98%, 99%, or 99.5% sequence identity to any of the foregoing. In some of any embodiments, the recombinant polymerase consists of a sequence that has at least at or about 80%, 85%, 90%, 95%, 96%, 97%, 98%, 99%, or 99.5% sequence identity to the sequence set forth in SEQ ID NO:6. In some of any embodiments, the recombinant polymerase consists of the sequence set forth in SEQ ID NO:6.

Provided herein are recombinant *Bacillus* phage AP50 polymerases comprising one or more amino acid substitutions, deletions or additions at one or more positions, corresponding to the positions of the sequence set forth in SEQ ID NO:1.

In some of any of the provided embodiments, the recombinant polymerase has at least at or about 80%, 85%, 90%, 95%, 96%, 97%, 98%, 99%, or 99.5% sequence identity to the sequence set forth in SEQ ID NO:1.

In some of any of the provided embodiments, the recombinant polymerases also comprises a heterologous sequence.

In some of any of the provided embodiments, the heterologous sequence comprises one or more tags, linkers, and/or polypeptide domains. In some of any embodiments, the heterologous sequence comprises one or more tags. In some of any embodiments, the tag is selected from among a poly histidine (HIS) tag, a solubility enhancement tag (SET), a small ubiquitin modified (SUMO) tag, a *Fasciola hepatica* 8-kDa antigen (Fh8) tag, a thioredoxin (Trx) tag, a glutathione-s-transferase (GST) tag, a maltose-binding protein (MBP) tag, an IgG domain B1 of protein G (GB1) tag, a mutated dehalogenase (Halo) tag, a streptavidin-binding peptide (SBP) tag, and a Tamavidin tag. In some of any embodiments, the tag comprises the sequence set forth in any of SEQ ID NOS:7, 8 and 26. In some of any embodiments, the tag comprises the sequence set forth in SEQ ID NO:7. In some of any embodiments, the tag comprises the sequence set forth in SEQ ID NO:8. In some of any embodiments, the tag comprises the sequence set forth in SEQ ID NO:26.

In some of any of the provided embodiments, the heterologous sequence comprises one or more polypeptide domains. In some of any embodiments, the polypeptide domain is selected from among a helix-hairpin-helix (HhH) DNA binding motif, a helix-hairpin-helix fusion [(HhH)$_2$] DNA binding motif, a single stranded DNA binding domain, an SD07 DNA binding motif, an SS07 DNA binding motif, and an *E. coli* HU domain.

In some of any of the provided embodiments, the heterologous sequence comprises one or more linkers. In some of any embodiments, the linker is at least at or about 1, 2, 3, 4, 5, 6, 7, 8, 9, 10, 15, 20, 25, 30, 40, or 50 amino acids in length. In some of any embodiments, the linker comprises the sequence set forth in any of SEQ ID NOS:10-16.

In some of any of the provided embodiments, the recombinant polymerase comprises the sequence set forth in SEQ ID NO:6, a linker, and a poly histidine (HIS) tag. In some of any embodiments, the recombinant polymerase comprises the sequence set forth in SEQ ID NO:6, a linker, a poly histidine (HIS) tag, and a solubility enhancement tag (SET).

In some of any embodiments, the recombinant polymerase comprises the sequence set forth in any one of SEQ ID NOS:2-4 or a sequence that has at least or about 80%, 85%, 90%, 95%, 96%, 97%, 98%, 99%, or 99.5% sequence identity to the sequence set forth in SEQ ID NOS:2-4. In some of any embodiments, the recombinant polymerase comprises the sequence set forth in SEQ ID NO:2. In some of any embodiments, the recombinant polymerase comprises the sequence set forth in SEQ ID NO:3. In some of any embodiments, the recombinant polymerase comprises the sequence set forth in SEQ ID NO:4.

In some of any of the provided embodiments, the recombinant polymerase is 900 amino acids or less in length. In some of any embodiments, the recombinant polymerase is 800 amino acids or less in length. In some of any embodiments, the recombinant polymerase is 732 amino acids or less in length. In some of any embodiments, the recombinant polymerase is 638 amino acids or less in length. In some of any embodiments, the recombinant polymerase is 600 amino acids or less in length. In some of any embodiments, the recombinant polymerase is 500 amino acids or less in length.

In some of any of the provided embodiments, recombinant polymerase has DNA synthesis activity. In some of any embodiments, the recombinant polymerase is capable of polymerizing DNA based on circular nucleic acid templates. In some of any embodiments, the recombinant polymerase has RNA synthesis activity. In some of any embodiments, the recombinant polymerase has strand displacement activity. In some of any embodiments, the recombinant polymerase has reverse transcriptase activity. In some of any embodiments, the recombinant polymerase has exonuclease activity.

In some of any of the provided embodiments, the recombinant polymerase exhibits one or more features selected from among improved processivity, improved polymerization rate, and improved thermostability, compared to a reference polymerase. In some of any embodiments, the recombinant polymerase exhibits improved processivity compared to a reference polymerase. In some of any embodiments, the recombinant polymerase exhibits improved kinetics compared to a reference polymerase. In some of any embodiments, the recombinant polymerase exhibits improved polymerization rate compared to a reference polymerase. In some of any embodiments, the recombinant polymerase exhibits improved thermostability compared to a reference polymerase.

In some of any of the provided embodiments, the recombinant polymerase is capable of generating a rolling-circle amplification (RCA) product in an RCA reaction. In some of any embodiments, the RCA reaction is performed at a temperature of at or about 5° C., 10° C., 15° C., 20° C., 25° C., 30° C., 35° C., 40° C., 45° C., or higher. In some of any embodiments, the recombinant polymerase generates a higher density of detected rolling-circle amplification (RCA) products in an RCA compared to a reference polymerase. In some of any embodiments, the recombinant polymerase generates a higher signal intensity in an RCA compared to a reference polymerase. In some of any embodiments, the reference polymerase is a Phi29 polymerase set forth in SEQ ID NO:5.

Also provided are compositions comprising any of the recombinant *Bacillus* phage AP50 polymerases described herein.

Also provided are polynucleotides encoding any of the recombinant *Bacillus phage AP*50 polymerases described herein.

In some of any embodiments, the polynucleotide comprises the sequence set forth in any one of SEQ ID NOS: 17-21, or a sequence that has at least at or about 90%, 95%, 96%, 97%, 98%, 99%, or 99.5% sequence identity to the sequence set forth in any one of SEQ ID NOS:17-21. In some of any embodiments, the polynucleotide comprises the sequence set forth in SEQ ID NO:17. In some of any embodiments, the polynucleotide comprises the sequence set forth in SEQ ID NO:18. In some of any embodiments, the polynucleotide comprises the sequence set forth in SEQ ID NO:19. In some of any embodiments, the polynucleotide comprises the sequence set forth in SEQ ID NO:20. In some of any embodiments, the polynucleotide comprises the sequence set forth in SEQ ID NO:21.

In some of any embodiments, the polynucleotide is codon-optimized for a recombinant expression system to generate the recombinant polymerase.

Also provided are recombinant nucleic acid molecules comprising any of the polynucleotides described herein, such as any of the polynucleotides encoding any of the recombinant polymerases described herein.

Also provided are recombinant nucleic acid molecules comprising a polynucleotide encoding a recombinant *Bacillus* phage AP50 polymerase comprising the sequence set forth in SEQ ID NO:6 or a sequence that has at least at or about 80%, 85%, 90%, 95%, 96%, 97%, 98%, 99%, or 99.5% sequence identity to the sequence set forth in SEQ ID NO:6. In some of any embodiments, the encoded recombinant polymerase comprises the sequence set forth in SEQ ID NO:6. In some of any embodiments, the encoded recombinant polymerase comprises the sequence set forth in SEQ ID NO:1 or a sequence that has at least at or about 80%, 85%, 90%, 95%, 96%, 97%, 98%, 99%, or 99.5% sequence identity to the sequence set forth in SEQ ID NO:1. In some of any embodiments, the encoded recombinant polymerase comprises the sequence set forth in SEQ ID NO:1. In some of any embodiments, the encoded recombinant polymerase consists of the sequence set forth in SEQ ID NO:1.

In some of any embodiments, the encoded recombinant nucleic acid molecules also comprise a transcription regulatory sequence operatively linked with the polynucleotide. In some of any embodiments, the transcription regulatory sequence comprises a promoter selected from among a bacterial, viral, and mammalian promoter.

Also provided are vectors comprising any of the polynucleotides or recombinant nucleic acid molecules described herein. In some of any embodiments, the vector comprises a plasmid, a phagemid, a viral vector, a cosmid, or a transposon.

Also provided herein are recombinant expression systems comprising any of the polynucleotides described herein, such as any of the polynucleotides encoding any of the recombinant polymerases described herein, any of the recombinant nucleic acid molecules described herein, or any of the vectors described herein.

In some of any embodiments, the polynucleotide, the recombinant nucleic acid molecule, or the vector is for use in transforming the recombinant expression system to generate a transformed recombinant expression system. In some of any embodiments, the transformed recombinant expression system generates the recombinant polymerase. In some of any embodiments, the recombinant expression system is a cell system or a cell-free system. In some of any embodiments, the recombinant expression system comprises one or more cell systems selected from among a bacterial cell, a fungal cell, an insect cell, and a mammalian cell.

In some of any embodiments, the polynucleotide sequence encoding the recombinant polymerase is codon-optimized for the recombinant expression system.

In some of any embodiments, the recombinant expression system produces the recombinant polymerase with improved solubility, improved processivity, improved polymerization rate, improved thermostability, and improved uniformity, compared to a reference polymerase.

Also provided are kits that include (1) any of the recombinant *Bacillus* phage AP50 polymerase described herein, any of the polynucleotides described herein, any of the recombinant nucleic acid molecules described herein, or any of the vectors described herein, and (2) one or more of: (a) dNTPs; (b) one or more di-cation; (c) reaction buffer; (d) a buffer for use with any of (a)-(c); and (e) instructions for use.

In some of any embodiments, the nucleic acid comprises deoxyribonucleotide residues. In some of any embodiments, the nucleic acid comprises one or more ribonucleotide residues.

In some of any embodiments, the kits also comprise one or more primers. In some of any embodiments, the kits also comprise one or more circularizable probes. In some of any embodiments, the kit is for nucleic acid amplification.

In some of any embodiments, the nucleic acid is amplified by rolling circle amplification (RCA) using the recombinant polymerase. In some of any embodiments, the nucleic acid is amplified in situ in the biological sample using the recombinant polymerase. In some of any embodiments, the kits also comprise a probe for detection of the amplified nucleic acid.

Also provided are kits comprising (1) any of the polynucleotides described herein, any of the recombinant nucleic acid molecules described herein, or any of the vectors described herein, and (2) a recombinant expression system. In some of any embodiments, the kits also comprise instructions for use. In some of any embodiments, the recombinant expression system is a cell system or a cell-free system. In some of any embodiments, the recombinant expression system comprises one or more cell systems selected from among a bacterial cell, a fungal cell, an insect cell, and a mammalian cell.

BRIEF DESCRIPTION OF THE DRAWINGS

The drawings illustrate certain features and advantages of this disclosure. These embodiments are not intended to limit the scope of the appended claims in any manner.

(FIG. 2A), 37° C. (FIG. 2B), 42° C. (FIG. 2C), and 50° C. (FIG. 2D).

DETAILED DESCRIPTION

Figure 1:
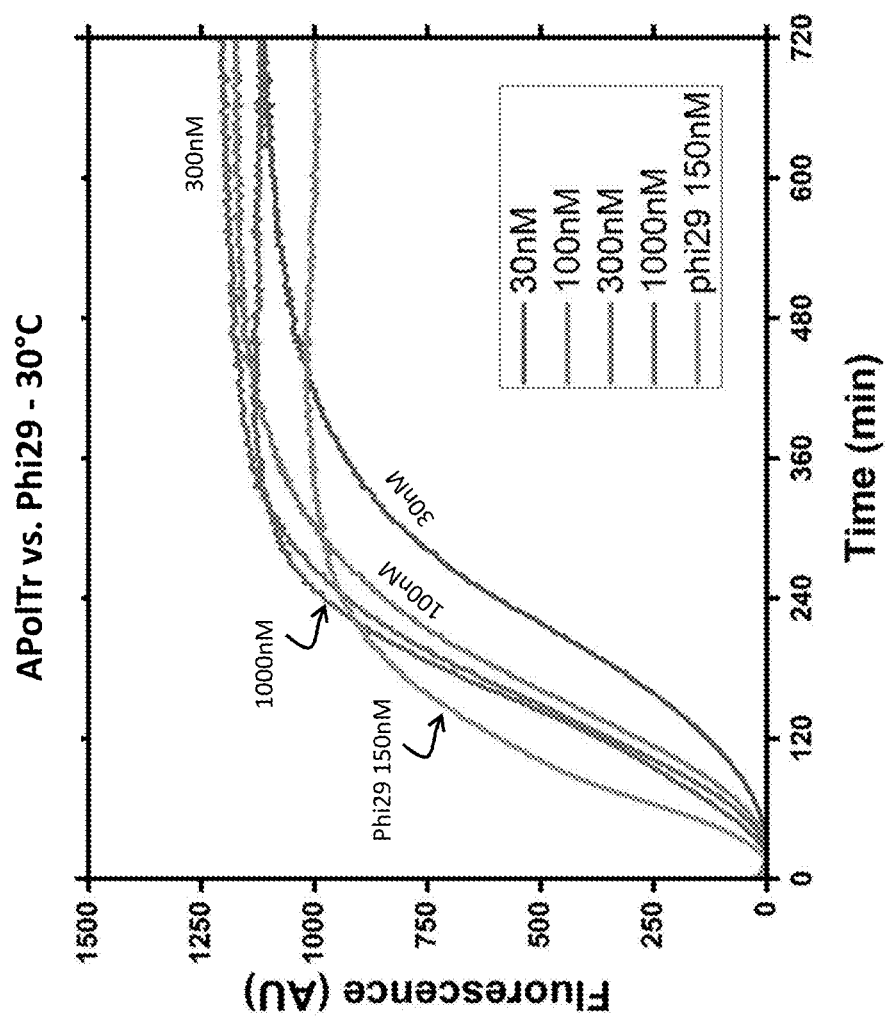
FIG. 1 depicts results from an in vitro rolling circle amplification (RCA) assay comparing activities of a wild-type Phi29 polymerase and an exemplary modified *Bacillus* phage AP50 polymerase (APolTr).
Figures 2A, 2B:
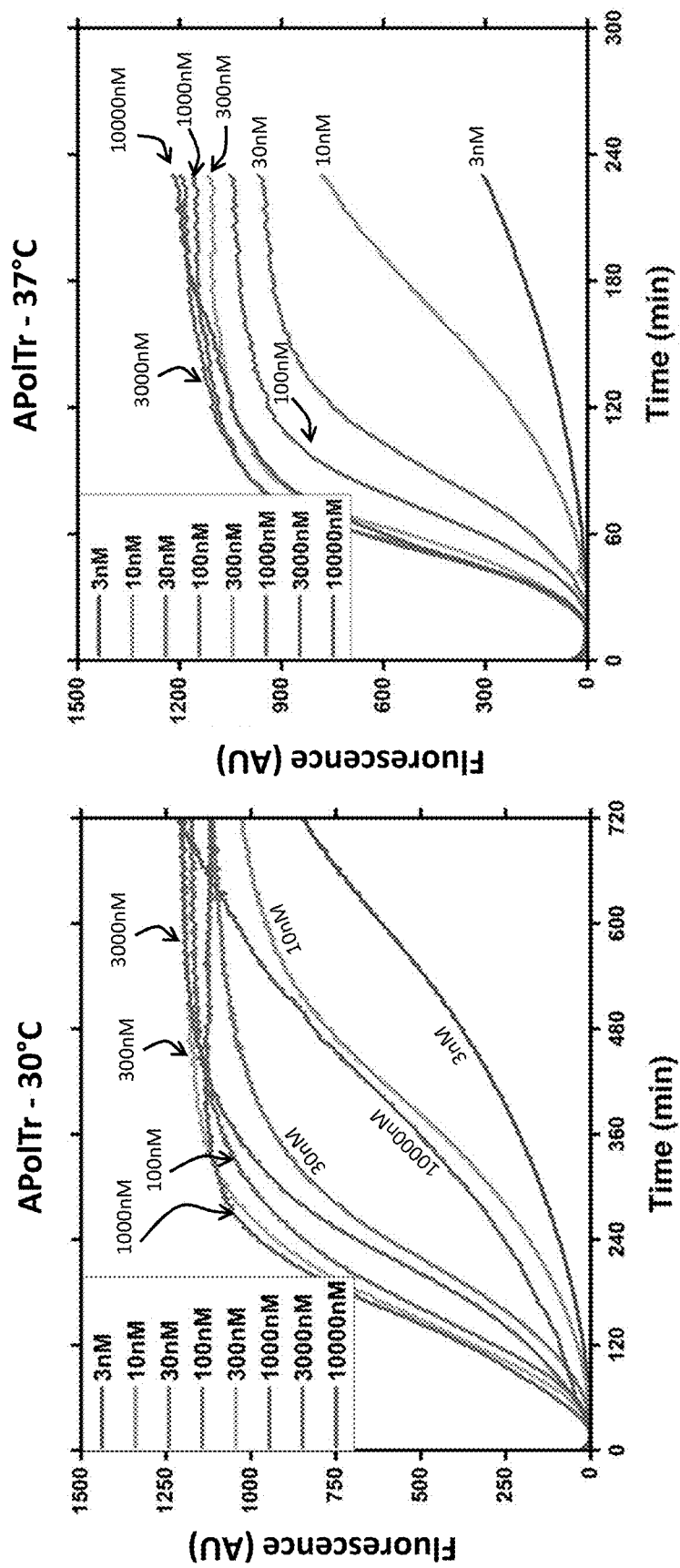
FIGS. 2A-2D depict results from an in vitro rolling circle amplification (RCA) assay comparing the activity of different concentrations of an exemplary modified *Bacillus* phage AP50 polymerase (APolTr) at 30° C.
Figures 2C, 2D:
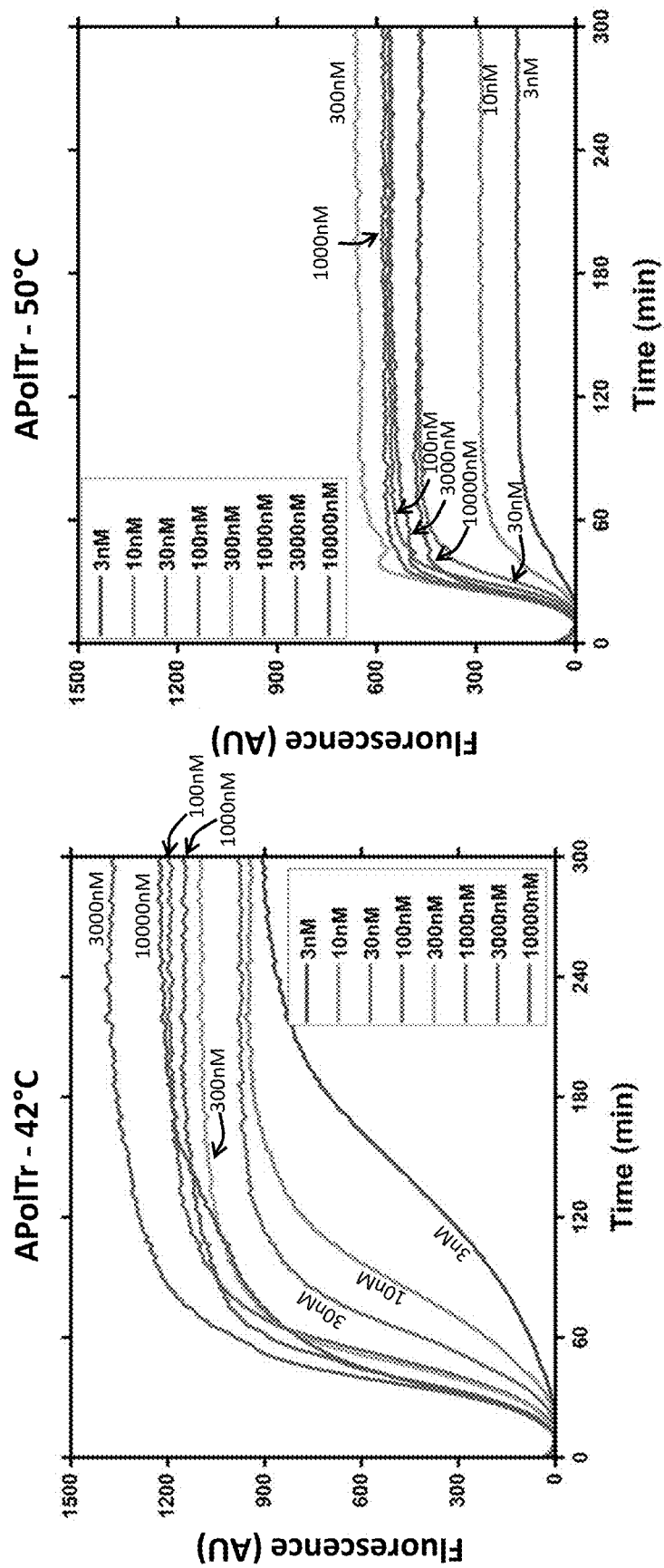

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. OVERVIEW

Provided herein are *Bacillus anthracis* phage AP50 polymerases (APol), and related methods and uses thereof, such as in amplifying nucleic acids. Also provided are recombinant and/or modified AP50 polymerases, for example, modified AP50 polymerases that comprise one or more amino acid deletions, insertions, substitutions, tru binant and/or modified polymerases comprising an AP50 polymerase sequence have features advantageous for performing rolling circle amplification. Notably, the recombinant and/or modified AP50 polymerase polypeptides provided herein demonstrate a higher polymerization rate and produce a higher number of detectable rolling circle amplification products under the same conditions (e.g., 30° C. and elevated temperatures) as Phi29 in a rolling circle amplification assay.

In some aspects, the provided embodiments are based on an observation that an exemplary recombinant AP50 polymerases and modified AP50 polymerase exhibited various improved properties for nucleic acid amplification, including improved thermostability at an elevated temperature (e.g., 42° C.), improved polymerization rate and increased rolling circle amplification (RCA) product generation, for example as observed by higher rate of polymerization and/or shorter reaction time, compared to a wild-type Phi29 polymerase. In some embodiments, the improved activity of the AP50 polymerase is in comparison to a wild-type Phi29 polymerase performed in an assay using the same or lower concentration of AP50 polymerase.

In some aspects, the provided AP50 polymerases can result in improvements in different types of assays and contexts for nucleic acid amplification, such as rolling circle amplification (RCA), both in in vitro assays and in situ assays, and using different types of tissue samples or target genes. In some aspects, the provided AP50 polymerases can be used to improve nucleic acid amplification, such as RCA, and result in improved analysis of biological samples, for example in vitro and in situ.

II. *BACILLUS ANTHRACIS* PHAGE AP50 POLYMERASES (APOL)

Provided herein are *Bacillus anthracis* phage AP50 polymerases, recombinant AP50 polymerases and modified AP50 polymerases, such as AP50 polymerases that comprise one or more variations or modifications compared to a wild-type, full-length or unmodified AP50 polymerase.

*Bacillus anthracis* phage AP50 polymerase (APol) is an uncharacterized phage protein, predicted to be a soluble DNA polymerase (e.g., Sozhamannan et al., Applied and Environmental Microbiology, 74(21):6792-6796). It is predicted to be a polymerase and is annotated as being encoded by the *B. anthracis* phage AP50 ORF 5. The full length AP50 polymerase is 732 amino acids (set forth in SEQ ID NO:27; 731 amino acids without the initial methionine or formyl methionine (fMet) residue, as set forth in SEQ ID NO:1), and shares 47% sequence identity with the *Bacillus thuringiensis* Bam35 phage protein. However, functions of the predicted AP50 polymerase has not been characterized, for example, it has not been demonstrated as having nucleic acid polymerase activity.

Phi29 is a mesophilic DNA polymerase derived from the *Bacillus subtilis* phage Phi29 having both a 3'-5' exonuclease activity and nucleic acid polymerization activity. Phi29 can be used for particular methods of amplifying and/or sequencing DNA and RNA, including isothermal rolling circle amplification (RCA) reactions. RCA reactions are important for single cell analysis and/or multiplexed analysis, for example, multiplex endogenous analyte detection and single-cell multiomic analyses (e.g., genomic, transcriptomic, and proteomic profiling). Such exemplary assays are important tools for understanding the molecular basis of the biology of cells and organisms, and also for assessment and/or treatment of diseases. In some cases, wild-type Phi29 has certain limitations, including limited thermostability, with an optimal reaction temperature of 30° C., which results in slower reaction kinetics, less amplification product, and greater heterogeneity and amplification bias, especially with DNA having high guanine/cytosine (G/C) content. In some aspects, the utility of wild-type Phi29 polymerase are limited, and the provided modified AP50 polymerases that are thermostable, can polymerize substrates faster, yield more amplification product and/or provide comparable assay sensitivity. In some aspects, the provided modified AP50 polymerases can be used in wider range of nucleic acid amplification methods or samples, for example, compared to a wild-type Phi29 polymerase.

A. Recombinant and/or Modified AP50 Polymerases

In some embodiments, provided herein are recombinant AP50 polymerases and modified AP50 polymerases. In some aspects, provided recombinant AP50 polymerases, e.g., a AP50 polymerase generated and/or purified recombinantly. In some aspects, provided are modified AP50 polymerases that is modified compared to a wild-type, full-length, or unmodified AP50 polymerase. In some embodiments, the modified AP50 polymerase comprises one or more variations or modifications, e.g., amino acid deletions, insertions, substitutions, truncations, and/or fusions of additional peptide or protein sequences, compared to the sequence of a reference polymerase, such as a wild-type, full-length AP50 polymerase, such as a wild-type, full-length AP50 polymerase set forth in SEQ ID NO:1 or SEQ ID NO:27. In some aspects, the modified AP50 polymerase is a variant of a wild-type AP50 polymerase. In some aspects, the modified AP50 polymerases are recombinantly produced and/or purified, or are for recombinant production and/or purification. In some aspects, the reference to "modified AP50 polymerase" can be understood to include that it is a recombinant AP50 polymerase. Provided herein are isolated and purified recombinant AP50 polymerases for performing an amplification reaction.

In some aspects, the modified AP50 polymerase comprises a heterologous sequence, e.g., a modified AP50 polymerase or portion thereof fused to a heterologous amino acid sequence. Exemplary modified AP50 polymerases include those designed to possess robust thermostability, processivity, sensitivity, specificity, solubility, polymerization rate, increase closed complex stability, decrease branching fraction, and/or other biological properties of the polymerase. In some aspects, exemplary modified AP50 polymerases demonstrate improved polymerase properties, for example, thermostability, processivity, sensitivity, specificity, solubility, polymerization rate, increase closed complex stability, decrease branching fraction, and/or other biological properties of the polymerase. Other exemplary modifications include modifications for immobilizing the polymerase on a surface or otherwise tagging the polymerase. Provided are recombinant AP50 polymerases or modified AP50 polymerases that exhibit one or more of such properties or features.

Also provided herein are compositions comprising any of the recombinant AP50 polymerases or modified AP50 polymerases, polynucleotides encoding any of the recombinant AP50 polymerases or modified AP50 polymerases, recombinant nucleic acid molecules encoding any of the recombinant AP50 polymerases or modified AP50 polymerases or comprising any of the polynucleotides, vectors encoding any of the modified AP50 polymerases or comprising any of the polynucleotides, recombinant expression systems encoding any of the recombinant AP50 polymerases or modified AP50 polymerases or comprising any of the polynucleotides and kits comprising or encoding any of the recombinant AP50 polymerases or modified AP50 polymerases, and methods for use and uses of any of the foregoing.

In some aspects, provided herein are modified AP50 polymerases comprising amino acid deletions at one or more positions compared to a wild-type AP50 polymerase. In some aspects, provided herein are modified AP50 polymerases that comprise an amino acid truncation compared to a wild-type AP50 polymerase. In some aspects, the wild-type AP50 polymerase comprises the sequence set forth in SEQ ID NO:1.

In some aspects, the provided AP50 polymerases comprise a deletion at one or more positions, with reference to SEQ ID NO:1. In some aspects, the modified AP50 polymerases comprise a truncation, with reference to SEQ ID NO:1. In some aspects, the one or more deletions or truncations are located at the N-terminus of the AP50 polymerase, with reference to SEQ ID NO:1. In some aspects, the AP50 polymerase comprise a deletion of one amino residue or two amino residues located at the N-terminus of the AP50 polymerase, with reference to SEQ ID NO:1. In some aspects, the one or more deletions or truncations are located at the C-terminus of the AP50 polymerase, with reference to SEQ ID NO:1.

In some aspects, the modified AP50 polymerase comprises a deletion of at least one amino acid residue compared to SEQ ID NO:1. In some aspects, the modified AP50 polymerase comprises a deletion of between 1 and 350, 5 and 300, 10 and 250, 25 and 150, 50 and 125, or 75 and 100 amino acid residues, such as contiguous amino acid residues, compared to SEQ ID NO:1. In some aspects, the modified AP50 polymerase comprises a deletion of at least 1, 5, 10, 25, 50, 75, 100, 150, 200, 250, 300, or 350 amino acid residues, such as contiguous amino acid residues, compared to SEQ ID NO:1. In some aspects, the modified AP50 polymerase comprises a deletion of 5, 10, 15, 20, 25, 30, 35, 40, 45, 50, 55, 60, 65, 70, 75, 80, 85, 90, 95, 100, 105, 110, 115 or 120 contiguous amino acids, or a within a range defined by any of the foregoing, with reference to SEQ ID NO:1. In some aspects, the modified AP50 polymerase comprises a deletion of 5, 10, 15, 20, 25, 30, 35, 40, 45, 50, 55, 60, 65, 70, 75, 80, 85, 90, 95, 100, 105, 110, 115 or 120 contiguous amino acids, or a within a range defined by any of the foregoing, from the N-terminus, with reference to SEQ ID NO:1. In some aspects, the modified AP50 polymerase comprises a deletion of 5, 10, 15, 20, 25, 30, 35, 40, 45, 50, 55, 60, 65, 70, 75, 80, 85, 90, 95, 100, 105, 110, 115 or 120 contiguous amino acids, or a within a range defined by any of the foregoing, from the C-terminus, with reference to SEQ ID NO:1.

In some aspects, the modified AP50 polymerase comprises a deletion of at least 25 amino acid residues, such as contiguous amino acid residues, compared to SEQ ID NO:1. In some aspects, the modified AP50 polymerase comprises a deletion of at least 50 amino acid residues, such as contiguous amino acid residues, compared to SEQ ID NO:1. In some aspects, the modified AP50 polymerase comprises a deletion of at least 75 amino acid residues, such as contiguous amino acid residues, compared to SEQ ID NO:1. In some aspects, the modified AP50 polymerase comprises a deletion of at least 100 amino acid residues, such as contiguous amino acid residues, compared to SEQ ID NO:1. In some aspects, the modified AP50 polymerase comprises a deletion of 94 contiguous amino acids from the C-terminus, with reference to SEQ ID NO:1. In some aspects, the modified AP50 polymerase comprises a truncation of 94 contiguous amino acids from the C-terminus, with reference to SEQ ID NO:1.

In some aspects, provided herein is a modified AP50 polymerase comprising two or more non-contiguous amino acid deletions, with reference to the positions of SEQ ID NO:1.

In some aspects, the modified AP50 polymerase comprising one or more deletions has at or about 80%, 85%, 90%, 95%, 96%, 97%, 98%, 99%, or 99.5% sequence identity to SEQ ID NO:1. In some aspects, the modified AP50 polymerase comprising one or more deletions has at least at or about 80% sequence identity to SEQ ID NO:1. In some aspects, the modified AP50 polymerase comprising one or more deletions has at least at or about 85% sequence identity to SEQ ID NO:1. In some aspects, the modified AP50 polymerase comprising one or more deletions has at least at or about 90% sequence identity to SEQ ID NO:1. In some aspects, the modified AP50 polymerase comprising one or more deletions has at least at or about 95% sequence identity to SEQ ID NO:1. In some aspects, the modified AP50 polymerase comprising one or more deletions has at least at or about 96% sequence identity to SEQ ID NO:1. In some aspects, the modified AP50 polymerase comprising one or more deletions has at least at or about 97% sequence identity to SEQ ID NO:1. In some aspects, the modified AP50 polymerase comprising one or more deletions has at least at or about 98% sequence identity to SEQ ID NO:1. In some aspects, the modified AP50 polymerase comprising one or more deletions has at least at or about 99% sequence identity to SEQ ID NO:1. In some aspects, the modified AP50 polymerase comprising one or more deletions has at least at or about 99.5% sequence identity to SEQ ID NO:1.

In some aspects, an exemplary wild-type full-length AP50 polymerase amino acid sequence is set forth in SEQ ID NO:1, which does not include the initial fMet residue. In some aspects, an exemplary wild-type full-length AP50 polymerase amino acid sequence is set forth in SEQ ID NO:27, which includes the initial fMet residue. In some of any of the provided embodiments, description of amino acid sequences and amino acid residues with reference to SEQ ID NO:1, is also understood to include a description of a corresponding amino acid sequences and amino acid residues from a corresponding sequence that includes the initial fMet residue, i.e., with reference to SEQ ID NO:27. In some aspects, amino acid residue 1 with reference to SEQ ID NO:1 corresponds to amino acid residue 2 with reference to SEQ ID NO:27. In some aspects, amino acid residue 731 with reference to SEQ ID NO:1 corresponds to amino acid residue 732 with reference to SEQ ID NO:27.

In some aspects, an exemplary truncated AP50 polymerase (e.g., a C-terminal truncation or a C-terminal deletion of 94 amino acids with reference to SEQ ID NO:1; i.e., truncation of amino acid residues 638-731 with reference to SEQ ID NO:1) amino acid sequence is set forth in SEQ ID NO:6, which does not include the initial fMet residue. In some aspects, an exemplary truncated AP50 polymerase (e.g., a C-terminal truncation or a C-terminal deletion of 94 amino acids with reference to SEQ ID NO:27; i.e., truncation of amino acid residues 639-732 with reference to SEQ ID NO:27) amino acid sequence is set forth in SEQ ID NO:32, which includes the initial fMet residue. In some of any of the provided embodiments, description of amino acid sequences and amino acid residues with reference to SEQ ID NO:6, is also understood to include a description of a corresponding amino acid sequences and amino acid residues from a corresponding sequence that includes the initial fMet residue, i.e., with reference to SEQ ID NO:32. In some aspects, amino acid residue 1 with reference to SEQ ID NO:6 corresponds to amino acid residue 2 with reference to SEQ ID NO:32. In some aspects, amino acid residue 637 with reference to SEQ ID NO:1 corresponds to amino acid residue 638 with reference to SEQ ID NO:27.

In some aspects, the modified AP50 polymerase comprises a contiguous portion of SEQ ID NO:6 of at least 200, 300, 400, 500 or 600 amino acids in length, or a sequence that has at least at or about 80%, 85%, 90%, 95%, 96%, 97%, 98%, 99%, or 99.5% sequence identity to a contiguous portion of SEQ ID NO:6 of at least 200, 300, 400, 500 or 600 amino acids in length. In some aspects, the modified AP50 polymerase comprises a contiguous portion of SEQ ID NO:6 of between 100 and 600, 200 and 500, or 300 and 400 amino acids in length.

In some aspects, the modified AP50 polymerase comprises a contiguous portion of SEQ ID NO:6 of at least 200 amino acids in length. In some aspects, the modified AP50 polymerase comprises a contiguous portion of SEQ ID NO:6 of at least 300 amino acids in length. In some aspects, the modified AP50 polymerase comprises a contiguous portion of SEQ ID NO:6 of at least 400 amino acids in length. In some aspects, the modified AP50 polymerase comprises a contiguous portion of SEQ ID NO:6 of at least 500 amino acids in length. In some aspects, the modified AP50 polymerase comprises a contiguous portion of SEQ ID NO:6 of at least 600 amino acids in length. In some aspects, the modified AP50 polymerase consists of a contiguous portion of SEQ ID NO:6 of at least 200 amino acids in length. In some aspects, the modified AP50 polymerase consists of a contiguous portion of SEQ ID NO:6 of at least 300 amino acids in length. In some aspects, the modified AP50 polymerase consists of a contiguous portion of SEQ ID NO:6 of at least 400 amino acids in length. In some aspects, the modified AP50 polymerase consists of a contiguous portion of SEQ ID NO:6 of at least 500 amino acids in length. In some aspects, the modified AP50 polymerase consists of a contiguous portion of SEQ ID NO:6 of at least 600 amino acids in length.

In some aspects, the modified AP50 polymerase comprises or consists of a sequence that has at least at or about 80% sequence identity to a contiguous portion of SEQ ID NO:6 of at least 400 amino acids in length. In some aspects, the modified AP50 polymerase comprises or consists of a sequence that has at least at or about 85% sequence identity to a contiguous portion of SEQ ID NO:6 of at least 400 amino acids in length. In some aspects, the modified AP50 polymerase comprises or consists of a sequence that has at least at or about 90% sequence identity to a contiguous portion of SEQ ID NO:6 of at least 400 amino acids in length. In some aspects, the modified AP50 polymerase comprises or consists of a sequence that has at least at or about 95% sequence identity to a contiguous portion of SEQ ID NO:6 of at least 400 amino acids in length. In some aspects, the modified AP50 polymerase comprises or consists of a sequence that has at least at or about 96% sequence identity to a contiguous portion of SEQ ID NO:6 of at least 400 amino acids in length. In some aspects, the modified AP50 polymerase comprises or consists of a sequence that has at least at or about 98% sequence identity to a contiguous portion of SEQ ID NO:6 of at least 400 amino acids in length. In some aspects, the modified AP50 polymerase comprises or consists of a sequence that has at least at or about 99% sequence identity to a contiguous portion of SEQ ID NO:6 of at least 400 amino acids in length. In some aspects, the modified AP50 polymerase comprises or consists of a sequence that has at least at or about 99.5% sequence identity to a contiguous portion of SEQ ID NO:6 of at least 400 amino acids in length.

In some aspects, the modified AP50 polymerase comprises or consists of a sequence that has at least at or about 80% sequence identity to a contiguous portion of SEQ ID NO:6 of at least 500 amino acids in length. In some aspects, the modified AP50 polymerase comprises or consists of a sequence that has at least at or about 85% sequence identity to a contiguous portion of SEQ ID NO:6 of at least 500 amino acids in length. In some aspects, the modified AP50 polymerase comprises or consists of a sequence that has at least at or about 90% sequence identity to a contiguous portion of SEQ ID NO:6 of at least 500 amino acids in length. In some aspects, the modified AP50 polymerase comprises or consists of a sequence that has at least at or about 95% sequence identity to a contiguous portion of SEQ ID NO:6 of at least 500 amino acids in length. In some aspects, the modified AP50 polymerase comprises or consists of a sequence that has at least at or about 96% sequence identity to a contiguous portion of SEQ ID NO:6 of at least 500 amino acids in length. In some aspects, the modified AP50 polymerase comprises or consists of a sequence that has at least at or about 98% sequence identity to a contiguous portion of SEQ ID NO:6 of at least 500 amino acids in length. In some aspects, the modified AP50 polymerase comprises or consists of a sequence that has at least at or about 99% sequence identity to a contiguous portion of SEQ ID NO:6 of at least 500 amino acids in length. In some aspects, the modified AP50 polymerase comprises or consists of a sequence that has at least at or about 99.5% sequence identity to a contiguous portion of SEQ ID NO:6 of at least 500 amino acids in length.

In some aspects, the modified AP50 polymerase comprises or consists of a sequence that has at least at or about 80% sequence identity to a contiguous portion of SEQ ID NO:6 of at least 600 amino acids in length. In some aspects, the modified AP50 polymerase comprises or consists of a sequence that has at least at or about 85% sequence identity to a contiguous portion of SEQ ID NO:6 of at least 600 amino acids in length. In some aspects, the modified AP50 polymerase comprises or consists of a sequence that has at least at or about 90% sequence identity to a contiguous portion of SEQ ID NO:6 of at least 600 amino acids in length. In some aspects, the modified AP50 polymerase comprises or consists of a sequence that has at least at or about 95% sequence identity to a contiguous portion of SEQ ID NO:6 of at least 600 amino acids in length. In some aspects, the modified AP50 polymerase comprises or consists of a sequence that has at least at or about 96% sequence identity to a contiguous portion of SEQ ID NO:6 of at least 600 amino acids in length. In some aspects, the modified AP50 polymerase comprises or consists of a sequence that has at least at or about 98% sequence identity to a contiguous portion of SEQ ID NO:6 of at least 600 amino acids in length. In some aspects, the modified AP50 polymerase comprises or consists of a sequence that has at least at or about 99% sequence identity to a contiguous portion of SEQ ID NO:6 of at least 600 amino acids in length. In some aspects, the modified AP50 polymerase comprises or consists of a sequence that has at least at or about 99.5% sequence identity to a contiguous portion of SEQ ID NO:6 of at least 600 amino acids in length.

In some aspects, the modified AP50 polymerase comprises SEQ ID NO:6. In some aspects, the modified AP50 polymerase comprises a sequence that has at least at or about 80%, 85%, 90%, 95%, 96%, 97%, 98%, 99%, or 99.5% sequence identity to SEQ ID NO:6. In some aspects, the modified AP50 polymerase has at least at or about 80% sequence identity to SEQ ID NO:6. In some aspects, the modified AP50 polymerase has at least at or about 85% sequence identity to SEQ ID NO:6. In some aspects, the modified AP50 polymerase has at least at or about 90% sequence identity to SEQ ID NO:6. In some aspects, the modified AP50 polymerase has at least at or about 95% sequence identity to SEQ ID NO:6. In some aspects, the modified AP50 polymerase has at least at or about 96% sequence identity to SEQ ID NO:6. In some aspects, the modified AP50 polymerase has at least at or about 97% sequence identity to SEQ ID NO:6. In some aspects, the modified AP50 polymerase has at least at or about 98% sequence identity to SEQ ID NO:6. In some aspects, the modified AP50 polymerase has at least at or about 99% sequence identity to SEQ ID NO:6. In some aspects, the modified AP50 polymerase has at least at or about 99.5% sequence identity to SEQ ID NO:6. In some aspects, the modified AP50 polymerase consists of SEQ ID NO:6.

In some aspects, the modified AP50 polymerase comprises a contiguous portion of SEQ ID NO:1 of at least 200, 300, 400, 500, 600 or 700 amino acids in length, or a sequence that has at least at or about 80%, 85%, 90%, 95%, 96%, 97%, 98%, 99%, or 99.5% sequence identity to a contiguous portion of SEQ ID NO:1 of at least 200, 300, 400, 500, 600 or 700 amino acids in length. In some aspects, the modified AP50 polymerase comprises a contiguous portion of SEQ ID NO:1 of between 100 and 700, 200 and 600, 300 and 500, or 350 and 450 amino acids in length.

In some aspects, the modified AP50 polymerase comprises a contiguous portion of SEQ ID NO:1 of at least 200 amino acids in length. In some aspects, the modified AP50 polymerase comprises a contiguous portion of SEQ ID NO:1 of at least 300 amino acids in length. In some aspects, the modified AP50 polymerase comprises a contiguous portion of SEQ ID NO:1 of at least 400 amino acids in length. In some aspects, the modified AP50 polymerase comprises a contiguous portion of SEQ ID NO:1 of at least 500 amino acids in length. In some aspects, the modified AP50 polymerase comprises a contiguous portion of SEQ ID NO:1 of at least 600 amino acids in length. In some aspects, the modified AP50 polymerase consists of a contiguous portion of SEQ ID NO:1 of at least 200 amino acids in length. In some aspects, the modified AP50 polymerase consists of a contiguous portion of SEQ ID NO:1 of at least 300 amino acids in length. In some aspects, the modified AP50 polymerase consists of a contiguous portion of SEQ ID NO:1 of at least 400 amino acids in length. In some aspects, the modified AP50 polymerase consists of a contiguous portion of SEQ ID NO:1 of at least 500 amino acids in length. In some aspects, the modified AP50 polymerase consists of a contiguous portion of SEQ ID NO:1 of at least 600 amino acids in length. In some aspects, the modified AP50 polymerase consists of a contiguous portion of SEQ ID NO:1 of at least 700 amino acids in length.

In some aspects, the modified AP50 polymerase comprises or consists of a sequence that has at least at or about 80% sequence identity to a contiguous portion of SEQ ID NO:1 of at least 400 amino acids in length. In some aspects, the modified AP50 polymerase comprises or consists of a sequence that has at least at or about 85% sequence identity to a contiguous portion of SEQ ID NO:1 of at least 400 amino acids in length. In some aspects, the modified AP50 polymerase comprises or consists of a sequence that has at least at or about 90% sequence identity to a contiguous portion of SEQ ID NO:1 of at least 400 amino acids in length. In some aspects, the modified AP50 polymerase comprises or consists of a sequence that has at least at or about 95% sequence identity to a contiguous portion of SEQ ID NO:1 of at least 400 amino acids in length. In some aspects, the modified AP50 polymerase comprises or consists of a sequence that has at least at or about 96% sequence identity to a contiguous portion of SEQ ID NO:1 of at least 400 amino acids in length. In some aspects, the modified AP50 polymerase comprises or consists of a sequence that has at least at or about 98% sequence identity to a contiguous portion of SEQ ID NO:1 of at least 400 amino acids in length. In some aspects, the modified AP50 polymerase comprises or consists of a sequence that has at least at or about 99% sequence identity to a contiguous portion of SEQ ID NO:1 of at least 400 amino acids in length. In some aspects, the modified AP50 polymerase comprises or consists of a sequence that has at least at or about 99.5% sequence identity to a contiguous portion of SEQ ID NO:1 of at least 400 amino acids in length.

In some aspects, the modified AP50 polymerase comprises or consists of a sequence that has at least at or about 80% sequence identity to a contiguous portion of SEQ ID NO:1 of at least 500 amino acids in length. In some aspects, the modified AP50 polymerase comprises or consists of a sequence that has at least at or about 85% sequence identity to a contiguous portion of SEQ ID NO:1 of at least 500 amino acids in length. In some aspects, the modified AP50 polymerase comprises or consists of a sequence that has at least at or about 90% sequence identity to a contiguous portion of SEQ ID NO:1 of at least 500 amino acids in length. In some aspects, the modified AP50 polymerase comprises or consists of a sequence that has at least at or about 95% sequence identity to a contiguous portion of SEQ ID NO:1 of at least 500 amino acids in length. In some aspects, the modified AP50 polymerase comprises or consists of a sequence that has at least at or about 96% sequence identity to a contiguous portion of SEQ ID NO:1 of at least 500 amino acids in length. In some aspects, the modified AP50 polymerase comprises or consists of a sequence that has at least at or about 98% sequence identity to a contiguous portion of SEQ ID NO:1 of at least 500 amino acids in length. In some aspects, the modified AP50 polymerase comprises or consists of a sequence that has at least at or about 99% sequence identity to a contiguous portion of SEQ ID NO:1 of at least 500 amino acids in length. In some aspects, the modified AP50 polymerase comprises or consists of a sequence that has at least at or about 99.5% sequence identity to a contiguous portion of SEQ ID NO:1 of at least 500 amino acids in length.

In some aspects, the modified AP50 polymerase comprises or consists of a sequence that has at least at or about 80% sequence identity to a contiguous portion of SEQ ID NO:1 of at least 600 amino acids in length. In some aspects, the modified AP50 polymerase comprises or consists of a sequence that has at least at or about 85% sequence identity to a contiguous portion of SEQ ID NO:1 of at least 600 amino acids in length. In some aspects, the modified AP50 polymerase comprises or consists of a sequence that has at least at or about 90% sequence identity to a contiguous portion of SEQ ID NO:1 of at least 600 amino acids in length. In some aspects, the modified AP50 polymerase comprises or consists of a sequence that has at least at or about 95% sequence identity to a contiguous portion of SEQ ID NO:1 of at least 600 amino acids in length. In some aspects, the modified AP50 polymerase comprises or consists of a sequence that has at least at or about 96% sequence identity to a contiguous portion of SEQ ID NO:1 of at least 600 amino acids in length. In some aspects, the modified AP50 polymerase comprises or consists of a sequence that has at least at or about 98% sequence identity to a contiguous portion of SEQ ID NO:1 of at least 600 amino acids in length. In some aspects, the modified AP50 polymerase comprises or consists of a sequence that has at least at or about 99% sequence identity to a contiguous portion of SEQ ID NO:1 of at least 600 amino acids in length. In some aspects, the modified AP50 polymerase comprises or consists of a sequence that has at least at or about 99.5% sequence identity to a contiguous portion of SEQ ID NO:1 of at least 600 amino acids in length.

In some aspects, the modified AP50 polymerase comprises or consists of a sequence that has at least at or about 80% sequence identity to a contiguous portion of SEQ ID NO:1 of at least 700 amino acids in length. In some aspects, the modified AP50 polymerase comprises or consists of a sequence that has at least at or about 85% sequence identity to a contiguous portion of SEQ ID NO:1 of at least 700 amino acids in length. In some aspects, the modified AP50 polymerase comprises or consists of a sequence that has at least at or about 90% sequence identity to a contiguous portion of SEQ ID NO:1 of at least 700 amino acids in length. In some aspects, the modified AP50 polymerase comprises or consists of a sequence that has at least at or about 95% sequence identity to a contiguous portion of SEQ ID NO:1 of at least 700 amino acids in length. In some aspects, the modified AP50 polymerase comprises or consists of a sequence that has at least at or about 96% sequence identity to a contiguous portion of SEQ ID NO:1 of at least 700 amino acids in length. In some aspects, the modified AP50 polymerase comprises or consists of a sequence that has at least at or about 98% sequence identity to a contiguous portion of SEQ ID NO:1 of at least 700 amino acids in length. In some aspects, the modified AP50 polymerase comprises or consists of a sequence that has at least at or about 99% sequence identity to a contiguous portion of SEQ ID NO:1 of at least 700 amino acids in length. In some aspects, the modified AP50 polymerase comprises or consists of a sequence that has at least at or about 99.5% sequence identity to a contiguous portion of SEQ ID NO:1 of at least 700 amino acids in length.

In some aspects, the modified AP50 polymerase comprises SEQ ID NO:1. In some aspects, the modified AP50 polymerase comprises a sequence that has at least at or about 80%, 85%, 90%, 95%, 96%, 97%, 98%, 99%, or 99.5% sequence identity to SEQ ID NO:1. In some aspects, the modified AP50 polymerase has at least at or about 80% sequence identity to SEQ ID NO:1. In some aspects, the modified AP50 polymerase has at least at or about 85% sequence identity to SEQ ID NO:1. In some aspects, the modified AP50 polymerase has at least at or about 90% sequence identity to SEQ ID NO:1. In some aspects, the modified AP50 polymerase has at least at or about 95% sequence identity to SEQ ID NO:1. In some aspects, the modified AP50 polymerase has at least at or about 96% sequence identity to SEQ ID NO:1. In some aspects, the modified AP50 polymerase has at least at or about 97% sequence identity to SEQ ID NO:1. In some aspects, the modified AP50 polymerase has at least at or about 98% sequence identity to SEQ ID NO:1. In some aspects, the modified AP50 polymerase has at least at or about 99% sequence identity to SEQ ID NO:1. In some aspects, the modified AP50 polymerase has at least at or about 99.5% sequence identity to SEQ ID NO:1. In some aspects, the modified AP50 polymerase consists of SEQ ID NO:1.

In some aspects, the exemplary modified AP50 polymerase comprises one or more deletion, insertion, and/or substitution, including any combinations of modifications or variations described herein, with reference to SEQ ID NO:1. In some aspects, such modifications or variations can be used to improve aspects of polymerase activity and/or other properties. In some aspects, the modified AP50 polymerase comprises an amino acid deletion of between 50 and 100 amino acids compared to SEQ ID NO:1. In some aspects, the modified AP50 polymerase is no more than 732 amino acids in length. In some aspects, the modified AP50 polymerase comprises a full length AP50 polymerase or a contiguous portion thereof comprising no more than 732 amino acid residues. In some aspects, the modified AP50 polymerase consists of a contiguous portion of SEQ ID NO:6 of at least 400 amino acids in length, or a sequence that has at least at or about 80%, 85%, 90%, 95%, 96%, 97%, 98%, 99%, or 99.5% sequence identity to any of the foregoing. In some aspects, the modified AP50 polymerase comprises SEQ ID NO:6. In some aspects, the modified AP50 polymerase consists of SEQ ID NO:6.

In some aspects, the modified AP50 polymerase comprising an AP50 polymerase domain (e.g., full-length AP50 polymerase or AP50 polymerase containing a modification, such as a deletion or truncation, or a contiguous portion thereof) is of a certain amino acid length. In some aspects, the modified AP50 polymerase is no more than 732, 731, 700, 650, 638, 637, 600, 550, 500, 450, or 400 amino acids, or within a range defined by any of the foregoing, in length. In some aspects, the modified AP50 polymerase is 732 amino acids or less in length. In some aspects, the modified AP50 polymerase is 731 amino acids or less in length. In some aspects, the modified AP50 polymerase is 638 amino acids or less in length. In some aspects, the modified AP50 polymerase is 637 amino acids or less in length. In some aspects, the modified AP50 polymerase is 600 amino acids or less in length. In some aspects, the modified AP50 polymerase is 500 amino acids or less in length. In some aspects, the modified AP50 polymerase is 732 amino acids in length. In some aspects, the modified AP50 polymerase is 731 amino acids in length. In some aspects, the modified AP50 polymerase is 638 amino acids in length. In some aspects, the modified AP50 polymerase is 637 amino acids in length. In some aspects, the modified AP50 polymerase is 600 amino acids in length. In some aspects, the modified AP50 polymerase is 500 amino acids in length.

In some aspects, the modified AP50 polymerase is a functional nucleic acid polymerase, for example, has DNA or RNA polymerase activity.

In some aspects, provided herein are modified AP50 polymerases comprising amino acid substitutions at one or more positions compared to the wild-type AP50 polymerase, for example, an AP50 polymerase sequence set forth in SEQ ID NO:1. In some aspects, provided herein are modified AP50 polymerases comprising amino acid insertions at one or more positions compared to the wild-type AP50 polymerase.

In some aspects, provided herein are modified AP50 polymerases further comprising heterologous amino acid sequences fused to the N-terminal and/or C-terminal compared to the wild-type AP50 polymerase.

Exemplary modified AP50 polymerases provided comprises one or more amino acid substitutions at one or more positions. In some aspects, the modified AP50 polymerase comprises one or more amino acid substitutions, with reference to SEQ ID NO:6. In some aspects, the modified AP50 polymerase comprises two or more amino acid substitutions, with reference to SEQ ID NO:6. In some aspects, the modified AP50 polymerase comprising one or more amino acid substitution has at least at or about 80%, 85%, 90%, 95%, 96%, 97%, 98%, 99%, or 99.5% sequence identity to SEQ ID NO:6. In some aspects, the AP50 polymerase comprises one or more amino acid substitution, with reference to SEQ ID NO:1. In some aspects, the modified AP50 polymerase comprises two or more amino acid substitutions, with reference to SEQ ID NO:1. In some aspects, the modified AP50 polymerase comprising one or more amino acid substitution has at least at or about 80%, 85%, 90%, 95%, 96%, 97%, 98%, 99%, or 99.5% sequence identity to SEQ ID NO:1. Exemplary modified AP50 polymerases comprises conservative or non-conservative amino acid substitutions. Exemplary modified AP50 polymerases may also comprise unnatural and/or synthetic amino acid substitutions.

In some aspects, the modified AP50 polymerase provided herein comprises one or more amino acid insertions. Examples of amino acid insertions include N-terminal insertions, C-terminal insertions and internal insertions of single or multiple amino acids. In some aspects, the modified AP50 polymerase comprises one or more amino acid insertions, with reference to SEQ ID NO:6. In some aspects, the modified AP50 polymerase comprises two or more amino acid insertions, with reference to SEQ ID NO:6. In some aspects, the modified AP50 polymerase comprising one or more amino acid insertion has at least at or about 80%, 85%, 90%, 95%, 96%, 97%, 98%, 99%, or 99.5% sequence identity to SEQ ID NO:6. In some aspects, the AP50 polymerase comprises one or more amino acid insertion, with reference to SEQ ID NO:1. In some aspects, the modified AP50 polymerase comprises two or more amino acid insertions, with reference to SEQ ID NO:1. In some aspects, the modified AP50 polymerase comprising one or more amino acid insertion has at least at or about 80%, 85%, 90%, 95%, 96%, 97%, 98%, 99%, or 99.5% sequence identity to SEQ ID NO:1. Exemplary modified AP50 polymerases comprises conservative or non-conservative amino acid insertions. In some examples, AP50 polymerases may also comprise unnatural and/or synthetic amino acid insertions.

In some aspects, the modified AP50 polymerase further comprises one or more heterologous sequences. In some of any of the embodiments herein, the recombinant AP50 polymerase comprises an affinity tag, a linker, and/or a solubility tag. In some aspects, the provided AP50 polymerases, such as those comprising one or more amino acid deletion and/or substitution further comprises one or more heterologous sequences. In some aspects, the modified AP50 polymerase comprises a deletion or truncation compared to the full-length wild-type AP50 polymerase, and one or more heterologous sequences.

In some aspects, the heterologous sequences has between 1 and 200, 2 and 180, 3 and 160, 5 and 140, 6 and 120, 7 and 100, 8 and 80, 9 and 60, 10 and 40, 15 and 30, 5 and 12, or 8 and 20 amino acid residues in length. In some aspects, the heterologous sequence is 1, 2, 3, 4, 5, 6, 7, 8, 9, 10, 20, 30, 40, 50, 60, 70, 80, 90, 100 or more amino acid residues, or a range defined by any of the foregoing. In some aspects, the heterologous sequence is no more than 200, 180, 160, 140, 120, 100, 80, 60, 40, 30, 20, or 10 amino acids in length. In some aspects, the heterologous sequence is no more than 200 amino acids in length. In some aspects, the heterologous sequence is no more than 150 amino acids in length. In some aspects, the heterologous sequence is no more than 100 amino acids in length.

Exemplary heterologous sequences include N- and/or C-terminal fusions ranging in length from one amino acid to polypeptides containing a hundred or more amino acids, as well as internal insertions of the heterologous sequences. Examples of heterologous sequences include the addition of affinity tags, linkers, and/or solubility domains. Other polypeptide domains that can be fused at the N- and/or C-terminal include domains from polypeptides or proteins such as an antibody or antibody domain, antibody fragment, antigen, receptor, receptor domain, receptor fragment, binding protein, or ligand. In some aspects, such heterologous sequences can alter or improve one or more properties of the polymerase.

In some aspects, the modified AP50 polymerase comprises one or more heterologous sequences, e.g., a tag and/or a linker. In some aspects, the modified AP50 polymerase comprises two or more heterologous sequences, e.g., a tag and/or a linker. In some aspects, the modified AP50 polymerase comprises three or more heterologous sequences, e.g., a tag and/or a linker. In some aspects, the modified AP50 polymerase (e.g., including one or more heterologous sequences) is of a certain amino acid length. In some aspects, the modified AP50 polymerase (e.g., including one or more heterologous sequences) is no more than 900, 800, 742, 741, 732, 731, 700, 650, 659, 658, 638, 637, 600, 550, 500, 450, or 400 amino acids, or within a range defined by any of the foregoing, in length. In some aspects, the modified AP50 polymerase is 742 amino acids or less in length. In some aspects, the modified AP50 polymerase is 741 amino acids or less in length. In some aspects, the modified AP50 polymerase is 732 amino acids or less in length. In some aspects, the modified AP50 polymerase is 731 amino acids or less in length. In some aspects, the modified AP50 polymerase is 659 amino acids or less in length. In some aspects, the modified AP50 polymerase is 658 amino acids or less in length. In some aspects, the modified AP50 polymerase is 638 amino acids or less in length. In some aspects, the modified AP50 polymerase is 637 amino acids or less in length. In some aspects, the modified AP50 polymerase is 600 amino acids or less in length. In some aspects, the modified AP50 polymerase is 500 amino acids or less in length. In some aspects, the modified AP50 polymerase is 742 amino acids in length. In some aspects, the modified AP50 polymerase is 741 amino acids in length. In some aspects, the modified AP50 polymerase is 732 amino acids in length. In some aspects, the modified AP50 polymerase is 731 amino acids in length. In some aspects, the modified AP50 polymerase is 659 amino acids in length. In some aspects, the modified AP50 polymerase is 658 amino acids in length. In some aspects, the modified AP50 polymerase is 638 amino acids in length. In some aspects, the modified AP50 polymerase is 637 amino acids in length. In some aspects, the modified AP50 polymerase is 600 amino acids in length. In some aspects, the modified AP50 polymerase is 500 amino acids in length.

In some aspects, the heterologous sequence is fused to the N- and/or C-terminal end of the AP50 polymerase domain (e.g., full-length AP50 polymerase or AP50 polymerase containing a modification, such as a deletion or truncation). In some aspects, the heterologous sequence is fused to the N-terminal end of the AP50 polymerase domain. In some aspects, the heterologous sequence is fused to the C-terminal end of the AP50 polymerase domain. In some aspects, a heterologous sequence is fused to the N-terminal end of the AP50 polymerase domain and another heterologous sequence is fused to the C-terminal end of the modified AP50 polymerase domain.

In some aspects, the modified AP50 polymerase comprises two or more heterologous sequences. In some aspects, the modified AP50 polymerase comprises an affinity tag, for example, a poly histidine (His) tag. In some aspects, the modified AP50 polymerase comprises an solubility tag, for example, a solubility enhancement tag (SET). In some aspects, the modified AP50 polymerase comprises an amino acid linker that connects the AP50 polymerase domain or a contiguous portion thereof (e.g., full-length AP50 polymerase or AP50 polymerase containing a modification, such as a deletion or truncation) to the tag. In some aspects, the two or more heterologous sequences are on adjacent to each other. In some aspects, the two or more heterologous sequences are indirectly fused e.g., separated by one or more amino acid residue.

In some aspects, the heterologous sequence includes a tag, e.g., an affinity tag and/or a solubility tag. In some aspects, the tag is a tag for recombinant purification, substrate binding, or addition of other tags. Exemplary tags include purification, substrate binding, or other tags, such as a poly histidine (His) tag, a His10 tag, a His6 tag, an alanine tag, an Ala10 tag, an Ala16 tag, a biotin tag, a biotin ligase recognition sequence or other biotin attachment site (e.g., a BiTag or a Btag or variant thereof, e.g., BtagV1-11), a GST tag, an S Tag, a SNAP-tag, an hemagglutinin (HA) tag, a DSB (Sso7D) tag, a lysine tag, a NanoTag, a Cmyc tag. In some aspects, the tag is selected from among a poly histidine (HIS) tag, a solubility enhancement tag (SET), a small ubiquitin modified (SUMO) tag, a *Fasciola hepatica* 8-kDa antigen (Fh8) tag, a thioredoxin (Trx) tag, a glutathione-s-transferase (GST) tag, a maltose-binding protein (MBP) tag, an IgG domain B1 of protein G (GB1) tag, a mutated dehalogenase (Halo) tag, a steptavidin-binding peptide (SBP) tag, and a Tamavidin tag. In some aspects, exemplary tags include those described in, for example, Kimple et al., Curr Protoc Protein Sci. 2013; 73: Unit-9.9. In some aspects, the tag is a poly HIS tag. In some aspects, the tag comprises the sequence set forth in SEQ ID NO:7. In some aspects, the tag is a SET tag. In some aspects, the tag comprises the sequence set forth in SEQ ID NO:8. In some aspects, the tag is a poly HIS tag and a SET tag. In some aspects, the heterologous sequence comprises the sequence set forth in SEQ ID NO:9. In some aspects, the tag is a SUMO tag. In some aspects, the tag comprises the sequence set forth in SEQ ID NO:26.

Exemplary heterologous sequences may be included to improve the solubility of modified AP50 polymerase, e.g., during recombinant expression, purification, and/or post-purification. In some aspects, the heterologous sequence comprises a tag for improving modified AP50 polymerase solubility. In some aspects, the tag is a solubility enhancement tag (SET). In some aspects, the tag has a net negative charge at pH 7. In some aspects, the tag comprising a negative charge improves the AP50 polymerase solubility and/or stability. In some aspects, the tag has a net negative charge of at least or at least about −1, −2, −4, −6, −10, −12, −14, −15, −16, −17, or −18. In some aspects, the tag has a net negative charge of −1, −2, −4, −6, −10, −12, −14, −15, −16, −17, or −18. In some aspects, the tag comprises one or more acidic amino acid residue, for example, an aspartic acid (Asp, D) and/or a glutamic acid (Glu, E). In some aspects, the tag comprises at least 2, 3, 4, 5, 6, 7, 8, 9, 10, or more acidic amino acid residues. In some aspects, the tag is between 1 and 50, 2 and 40, 3 and 30, 5 and 20, 5 and 12, or 8 and 20 amino acid residues in length. In some aspects, the tag comprises a sequence set forth in SEQ ID NOS:8 or 10. In some aspects, the tag comprises SEQ ID NO:8. In some aspects, the tag comprises SEQ ID NO:10.

In some aspects, the heterologous sequence comprising a tag is directly fused to the AP50 polymerase domain. In some aspects, the tag is fused directly to the N- and/or C-terminal end of the AP50 polymerase domain. In some aspects, the tag is indirectly fused to the AP50 polymerase domain. In some aspects, the tag is fused to a second heterologous sequence, for example, a linker or another tag. In some aspects, the tag is inserted in the interior portion of the AP50 polymerase domain. In some of any of the embodiments herein, the recombinant AP50 polymerase is fused to a solubility tag directly to C-terminal end of the AP50 polymerase domain. In some of any of the embodiments herein, the recombinant AP50 polymerase is fused to a solubility tag indirectly to C-terminal end of the AP50 polymerase domain via a linker.

In some aspects, the heterologous sequence comprises one or more polypeptide domains, e.g., a fusion domain. In some aspects, the tag is a tag for recombinant expression and purification, substrate binding, or improved polymerase performance. In some aspects, the polypeptide domain comprises a domain selected from among a helix-hairpin-helix (HhH) DNA binding motif, a helix-hairpin-helix fusion [(HhH)$_2$] DNA binding motif, a single stranded DNA binding domain, an SD07 DNA binding motif, an SS07 DNA binding motif, and an *E. coli* HU domain.

In some aspects, the polypeptide domain is an HhH domain. In some aspects, exemplary tags include those described in, for example, Ordonez et al., Sci Rep. 2020; 10:15046 and Pavlov et al., PNAS 2002; 99(21):13510-5. In some aspects, exemplary polypeptide domains include HhH domains or motifs from any of the following proteins: Accession No. Q93H64 from *Streptomyces avermitilis*; Accession No. Q9CEH6 from *Lactococcus lactis*; Accession No. O00847 from *Trypanosoma brucei*; Accession No. Q8Y7P2 from *Listeria monocytogenes*; Accession No. RL32_HALN1 from *Halobacterium*; Accession No. Q99YR8 from *Streptococcus pyogenes*; Accession No. Q55769 from *Synechocystis*; Accession No. YACK_BACSU from *Bacillus subtilis*; Accession No. Q91VP3 from *Mus musculus*; Accession No. P91153 from *Caenorhabditis elegans*; Accession No. P77987 from *Thermus aquaticus*; Accession No. Q9KGG0 from *Bacillus halodurans*; Accession No. AAM31590 from *Methanosarcina mazei* goe1; Accession No. Q9APN0 from *Myxococcus xanthus*; Accession No. Q8XHQ0 from *Clostridium perfringens*; Accession No. Q9C0F7 from *Homo sapiens*; Accession No. Q8XGV0 from *Salmonella typhimurium*; Accession No. O26650 from *Methanobacterium thermoautotrophicum*; Accession No. AAM02649 from *Methanopyrus kandleri* av19; Accession No. Q9D7J3 from *Mus musculus*; Accession No. AAM38234 from *Xanthomonas axonopodis*; Accession No. P94624 from *Clostridium difficile*; Accession No. O74103 from *Pyrococcus horikoshii*; Accession No. AAK99660 from *Streptococcus pneumoniae* r6; Accession No. AAM02248 from *Methanopyrus kandleri* av19; Accession No. AAH28155 from *Homo sapiens*; Accession No. P71728 from *Mycobacterium tuberculosis*; Accession No. AAM06574 from *Methanosarcina acetivorans* str; Accession No. Q9YC15 from *Aeropyrum pernix*; Accession No. AAK99347 from *Streptococcus pneumoniae* r6; Accession No. AAH93832 from *nucleatum*; Accession No. AAH08930 from *Homo sapiens*; Accession No. EX9_ECOLI from *Escherichia coli*; Accession No. AAL81517 from *Pyrococcus furiosus* dsm 3638; Accession No. Q8Y3B2 from *Ralstonia solanacearum*; Accession No.

Q8XBD5 from *Escherichia coli* o157:h7; Accession No. Q8XIJ9 from *Clostridium perfringens*; Accession No. Q9PJA0 from *Campylobacter jejuni*; Accession No. Q9RA49 from *Thermus aquaticus*; Accession No. AAM25145 from *Thermoanaerobacter tengcongensis*; Accession No. BAB95406 from *Staphylococcus aureus*; Accession No. AAM01328 from *Methanopyrus kandleri* av19; Accession No. AAM25645 from *Thermoanaerobacter tengcongensis*; Accession No. AAL95150 from *nucleatum*; Accession No. Q8VQ77 from *Bacillus licheniformis*; Accession No. HELS_METJA from Methanococcus jannaschii; Accession No. Q92D76 from *Listeria innocua*; Accession No. AAL95286 from *nucleatum*; Accession No. Q8XBL5 from *Escherichia coli* o157:h7; Accession No. Q9HZ87 from *Pseudomonas aeruginosa*; Accession No. Q9GRA1 from *Hydra oligactis*; Accession No. Q98AC3 from *Rhizobium loti*; Accession No. RPOA_SPIMX from Spirogyra maxima; Accession No. AAL91594 from *Homo sapiens*; Accession No. Q8Y8F9 from *Listeria monocytogenes*; Accession No. Q99LC7 from *Mus musculus*; Accession No. P72464 from *Streptomyces lividans*; Accession No. Q96K64 from *Homo sapiens*; Accession No. Q974S1 from *Sulfolobus tokodaii*; Accession No. Q9HMU5 from *Halobacterium*; Accession No. Q8XE54 from *Escherichia coli* o157:h7; Accession No. Q96NY9 from *Homo sapiens*; Accession No. AAM34796 from *Homo sapiens*; Accession No. AAL98145 from *Streptococcus pyogenes* mgas8232; Accession No. O27790 from *Methanobacterium* thermoautotrophicum; Accession No. AAL92998 from Dictyostelium discoideum; Accession No. AAM05700 from *Methanosarcina acetivorans* str; Accession No. RADA_METMP from Methanococcus maripaludis; Accession No. AAK99292 from *Streptococcus pneumoniae* r6; Accession No. AAM04167 from *Methanosarcina acetivorans* str; Accession No. Q91869 from *Xenopus laevis*; Accession No. AAM06907 from *Methanosarcina acetivorans* str; Accession No. Q94K65 from *Arabidopsis thaliana*; Accession No. Q8XIE6 from *Clostridium perfringens*; Accession No. AAH27384 from *Mus musculus*; Accession No. Q97EC6 from *Clostridium acetobutylicum*; Accession No. AAM23354 from *Thermoanaerobacter tengcongensis; Accession No. Q9FF89 from Arabidopsis thaliana*; Accession No. AAM02891 from *Methanopyrus kandleri* av19; Accession No. HELS_METTH from *Methanobacterium* thermoautotrophicum; Accession No. AAL82139 from *Pyrococcus furiosus* dsm 3638; Accession No. O30253 from *Archaeoglobus fulgidus*; Accession No. Q9HSD6 from *Halobacterium*; Accession No. Q9WY43 from *Thermotoga maritima*; Accession No. AAK84937 from *Drosophila melanogaster*; Accession No. AAL98006 from *Streptococcus pyogenes* mgas8232; Accession No. O85197 from *Streptococcus pneumoniae*; Accession No. AAM31083 from *Methanosarcina mazei* goe1; Accession No. AAM24182 from *Thermoanaerobacter tengcongensis*; Accession No. Q9HMW5 from *Halobacterium*; Accession No. RECR_BACSU from *Bacillus subtilis*; Accession No. Q9BTN8 from *Homo sapiens*; Accession No. Q8X233 from *Aeropyrum pernix*; and Accession No. NOD_DROME from *Drosophila melanogaster*. In some aspects, the polypeptide domain comprises an [(HhH)$_2$] domain, for example, as described in Ordonez et al., Sci Rep. 2020; 10:15046. In some aspects, the polypeptide domain comprises an [(HhH)$_2$] domain comprising one or more of any of the HhH domains described herein. In some aspects, the polypeptide domain comprises an [(HhH)$_2$] domain comprising a fusion of any two or more of the HhH domains described herein. In some aspects, a [(HhH)$_2$] domain is a fusion of the H and I DNA-binding domains of *Methanopyrus kandleri* topoisomerase V.

In some aspects, the heterologous sequence comprises one or more linkers. In some aspects, the modified AP50 polymerase comprises two or more linkers. In some aspects, the linker comprises one or more glycine, serine, alanine, histidine, arginine, lysine, glutamine and/or proline residues. In some aspects, the linker comprises one or more glycine and/or serine residues. In some aspects, the linker is 1, 2, 3, 4, 5, 6, 7, 8, 9, 10, or more amino acid residues, or a range defined by any of the foregoing, in length. In some aspects, the linker is between 1 and 30, 2 and 25, 3 and 20, 4 and 18, 5 and 16, 6 and 14, 7 and 12, or 8 and 10 amino acid residues in length.

In some aspects, the linker is a flexible linker or a rigid linker. In some aspects, the linker comprises a cleavable linker sequence. Cleavable linkers are often cleaved, for example, by enzymatic or reductive mechanisms. Exemplary cleavable linkers include protease sensitive linkers, cyclopeptide linkers, and/or disulfide sensitive linkers. In some aspects, the heterologous sequence comprises a cleavable sequence. Cleavable sequences are often cleaved, for example, by enzymatic or reductive mechanisms. Exemplary cleavable sequences include protease sensitive sequences, cyclopeptide sequences, and/or disulfide sensitive sequences. In some aspects, the modified AP50 polymerase comprises a heterologous sequences comprising a cleavable sequence. In some aspects, the cleavable sequence is included in a linker. In some aspects, the cleavable sequence is included in a non-linker sequence. Exemplary cleavable sequences can be included to remove one or more heterologous sequence from the modified AP50 polymerase, e.g., after recombinant expression and/or purification. In some aspects, the linker comprises any one of SEQ ID NOS:10-16. In some aspects, the linker comprises SEQ ID NO:10. In some aspects, the linker comprises SEQ ID NO:11. In some aspects, the linker comprises SEQ ID NO:12. In some aspects, the linker comprises SEQ ID NO:13. In some aspects, the linker comprises SEQ ID NO:14. In some aspects, the linker comprises SEQ ID NO:15. In some aspects, the linker comprises SEQ ID NO:16.

In some aspects, the linker is fused to the N- and/or C-terminal end of the AP50 polymerase domain (e.g., full-length AP50 polymerase or AP50 polymerase containing a modification, such as a deletion or truncation). In some aspects, the linker is directly fused to the N- and/or C-terminal end of the AP50 polymerase domain. In some aspects, the linker is indirectly fused to the N- and/or C-terminal end of the AP50 polymerase domain. In some aspects, the linker is fused to the C-terminal end of the AP50 polymerase domain.

In some aspects, the modified AP50 polymerase comprises two or more heterologous sequences, e.g., a tag and/or a linker. In some aspects, the modified AP50 polymerase comprises three or more heterologous sequences, e.g., a tag and/or a linker. In some aspects, the modified AP50 polymerase comprises one or more sequences selected from among any one of SEQ ID NOS:7, 8, 10, and 26. In some aspects, the modified AP50 polymerase comprises one or more sequences selected from among any one of SEQ ID NOS:10-16. In some aspects, the modified AP50 polymerase comprises a heterologous sequence comprising one or more of a poly histidine (His) tag and a SET tag. In some aspects, the modified AP50 polymerase comprises a heterologous sequence comprising a linker.

In some aspects, the modified AP50 polymerase comprises, in N- to C-terminal order: SEQ ID NO:6, SEQ ID NO:10, and SEQ ID NO:7. In some aspects, the modified AP50 polymerase comprises, in N- to C-terminal order: SEQ ID NO:6, SEQ ID NO:10, SEQ ID NO:7, and SEQ ID NO:8. In some aspects, the modified AP50 polymerase comprises, in N- to C-terminal order: SEQ ID NO:6 and SEQ ID NO:9. In some aspects, the modified AP50 polymerase comprises, in N- to C-terminal order: SEQ ID NO:1, SEQ ID NO:10, and SEQ ID NO:7. In some aspects, the modified AP50 polymerase comprises, in N- to C-terminal order: SEQ ID NO:1, SEQ ID NO:10, SEQ ID NO:7, and SEQ ID NO:8. In some aspects, the modified AP50 polymerase comprises any one of SEQ ID NOS:2-4. In some aspects, the modified AP50 polymerase comprises SEQ ID NO:2. In some aspects, the modified AP50 polymerase comprises SEQ ID NO:3. In some aspects, the modified AP50 polymerase comprises SEQ ID NO:4. In some aspects, the modified AP50 polymerase consists of any one of SEQ ID NOS:2-4. In some aspects, the modified AP50 polymerase consists of SEQ ID NO:2. In some aspects, the modified AP50 polymerase consists of SEQ ID NO:3. In some aspects, the modified AP50 polymerase consists of SEQ ID NO:4.

In some aspects, the modified AP50 polymerases provided herein can be used as part of a chimeric polymerase, e.g., a polymerase made from a mosaic of different sources or origins. Chimeras can be produced, e.g., using consideration of similarity regions between the polymerases to define consensus sequences that are used in the chimera, or using gene shuffling technologies, for example in which multiple AP50 polymerase or related polymerases are randomly or semi-randomly shuffled via available gene shuffling techniques (e.g., via "family gene shuffling"; see Crameri et al. (1998) Nature 391:288-291; Clackson et al. (1991) Nature 352:624-628; Gibbs et al. (2001) Gene 271:13-20; and Hiraga and Arnold (2003) J. Mol. Biol. 330:287-296). In certain aspects, for generating a chimeric polymerase, the recombination points can be predetermined such that the gene fragments assemble in the correct order, or at random. In some aspects, any of the modifications or variations described herein can be introduced into the chimeras, to achieve the desired improvements in property or features.

Exemplary modified AP50 polymerases include any combination of modifications or variations, such as deletion, insertion, and substitution, including any combinations of modifications or variations described herein or with any known modifications or variations in reference to SEQ ID NO:1. In some aspects, the modified AP50 polymerase possesses improved activity and/or properties, such as any described herein. In some aspects, such modifications or variations can be used to improve aspects of protein production or altering one or more properties of the polymerase, such as to achieve the improved activity and/or properties.

In some aspects, amino acid sequence variants of a modified AP50 polymerase may be prepared by introducing appropriate modifications into the nucleotide sequence encoding the wild-type AP50 polymerase, or by peptide synthesis. Exemplary of modifications or variations include, deletions from and/or insertions into and/or substitutions of residues within the amino acid sequences of the wild-type AP50 polymerase. The modified AP50 polymerases described herein can be recombinantly generated and/or purified from one or more suitable expression systems, for example, a cell system or a cell-free system, as a recombinant polymerase.

In some aspects, provided are compositions comprising a recombinant AP50 polymerase, e.g., a modified AP50 polymerase generated and/or purified recombinantly, such as those comprising one or more amino acid substitution, insertion, and/or deletion, as described herein. In some aspects, the composition has a purity of at least 70%, 75%, 80%, 85%, 90%, 95%, 96%, 97%, 98%, 99% or 99.5% with respect to the recombinant AP50 polymerase. In some aspects, at least 70%, 75%, 80%, 85%, 90%, 95%, 96%, 97%, 98%, 99% or 99.5% of the biomolecules present in the composition is a recombinant AP50 polymerase. In some aspects, at least 70%, 75%, 80%, 85%, 90%, 95%, 96%, 97%, 98%, 99% or 99.5% of the polypeptides or proteins of the composition is a recombinant AP50 polymerase. In some aspects, the composition comprising the recombinant AP50 polymerase a high level of purity and/or is nearly pure with respect to other biomolecules present in the composition, for example, other polypeptides, proteins, amino acids, nucleotides or polynucleotides. In some aspects, biomolecules other than recombinant AP50 polymerases may be considered contaminants within the composition. In some aspects, the composition has less than at or about 30%, 25%, 20%, 15%, 10%, 5%, 4%, 3%, 2%, 1% or 0.5% contaminants.

B. Exemplary Features of Modified AP50 Polymerases

In some aspects, the provided recombinant and/or modified AP50 polymerases may exhibit one or more improved features or properties. These features or properties relate to the activity and function of a nucleic acid polymerase, such as, but not limited, nucleic acid amplification. An exemplary improved feature may be related to the modified AP50 polymerase activity, function, performance, robustness, utility, or a combination thereof. Exemplary improved features of the provided AP50 polymerases relate to, for example, thermostability, processivity, sensitivity, specificity, solubility, and polymerization rate. Other exemplary features may relate to increased yield, altered cofactor selectivity, exonuclease deficiency, and/or increased resistance to photodamage. In some aspects, the provided modified AP50 polymerases exhibit improved thermostability, processivity, sensitivity, specificity, solubility, and/or polymerization rate, and/or that otherwise exhibit an improved ability to read through damaged, modified, or other difficult stretches of nucleic acid template, can be employed for precision amplification applications (e.g., RCA). In some aspects, the modified AP50 polymerase has strand displacing activity. In some aspects, the modified AP50 polymerase has exonuclease activity. In some aspects, the modified AP50 polymerase has reverse transcriptase activity. In some embodiments, the one or more feature is improved compared to a reference polymerase, such as a reference polymerase that is used for similar applications, e.g., nucleic acid amplification, or is known to have a similar function, e.g., nucleic acid polymerization. In some embodiments, the one or more feature is improved compared to a reference AP50 polymerase (e.g., wild-type AP50 polymerase). In some embodiments, the one or more feature is improved compared to a reference Phi29 polymerase (e.g., wild-type Phi29 polymerase) as set forth in SEQ ID NO:5. Improvements in one or more feature support an expanded application and/or utility of the recombinant and/or modified AP50 polymerase, for example for nucleic acid amplification and/or sequencing. In some embodiments, the provided modified AP50 polymerase possesses one or more feature resulting in improved nucleic acid amplification from a biological sample and/or nucleic acid amplification methods such as a rolling circle amplification (RCA).

1. Improved Thermostability

In some aspects, the thermostability of polymerases (e.g., wild-type Phi29 polymerase) used for particular nucleic acid amplification methods, e.g., RCA, can be limited. In some cases, the typical reaction temperature for wild-type Phi29 polymerase activity is about 30° C. In some aspects, many biological or chemical experiments, reactions and/or analysis require higher temperatures. For example, particular steps for nucleic acid amplification and/or sequencing methodology (e.g., probe ligation) are performed at or require higher temperatures, for example, for maximal efficiency. In some examples, most tissue culture growth, manipulation, and experimentation requires at higher temperatures. Using wild-type Phi29 polymerase at elevated temperatures can result in reduced polymerization rate, output and polymerase stability compared to polymerase activity at 30° C. In certain contexts, using Phi29 polymerases at a temperature such as 30° C. may complicate an experimental method, by introducing the need for multiple temperatures and temperature switching, such that in some cases, the method may be adaptable or amenable for high-throughput and high-volume applications.

In some embodiments, the recombinant and/or modified AP50 polymerase described herein exhibits improved thermostability. In some aspects, the improved thermostability includes improved polymerase activity. In some embodiments, the improved thermostability includes improved, more rapid, more robust, and/or more accurate polymerase activity, for example at elevated temperatures. In some embodiments, the provided modified AP50 polymerases, for example, those described in Section II.A, exhibit improved thermostability. In some embodiments, the modified AP50 polymerase exhibiting improved thermostability can be used for a nucleic acid amplification reaction, such as a DNA amplification reaction. In some embodiments, the modified AP50 polymerase is used in a nucleic acid amplification performed at a temperature of or about 5° C., 10° C., 15° C., 20° C., 25° C., 30° C., 35° C., 40° C., 45° C., 50° C., or higher. In some embodiments, the modified AP50 polymerase is used in a nucleic acid amplification performed between at or about 5° C. and 55° C., 10° C. and 50° C., 25° C. and 45° C., or 30° C. and 40° C. In some embodiments, the modified AP50 polymerase is used in a nucleic acid amplification performed at an elevated temperature. In some embodiments, the modified AP50 polymerase is used in a nucleic acid amplification performed at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C. or higher. In some embodiments, the modified AP50 polymerase is used in a nucleic acid amplification performed between at or about 30° C. and 55° C., 32° C. and 53° C., 34° C. and 51° C., 36° C. and 49° C., 38° C. and 47° C., or 40° C. and 45° C.

In some embodiments, the provided AP50 polymerases are more active (e.g., produce more amplified DNA) at the same concentration or a lower concentration compared to a reference polymerase (e.g., Phi29 polymerase). In some embodiments, the provided recombinant and/or modified AP50 polymerases produce more amplified DNA compared to a reference polymerase (e.g., wild-type Phi29 polymerase of SEQ ID NO:5). In some embodiments, the provided recombinant and/or modified AP50 polymerases produce more amplified DNA at elevated temperatures compared to a reference polymerase. In some embodiments, the provided recombinant and/or modified AP50 polymerases produce more amplified DNA compared to a wild-type AP50 polymerase of SEQ ID NO:1. In some embodiments, the increase in nucleic acid amplification and the generation of amplified nucleic acid product are measured or assessed using a fluorescent dye. Exemplary fluorescent dyes for measuring the increase in nucleic acid amplification and the generation of amplified nucleic acid product, such as in an RCA reaction, include any described herein. In some embodiments, the modified AP50 polymerase produces at or about or more than at or about 1%, 5%, 10%, 15%, 20%, 25%, 30%, 40%, 50%, 75%, 100%, 150%, or 200% more amplified DNA compared to a reference polymerase. In some embodiments, the modified AP50 polymerase produces between 10% and 200%, 25% and 175%, 50% and 150%, 75% and 125%, 90% and 110%, or 95% and 105% more amplified DNA compared to a reference polymerase.

In some embodiments, the modified AP50 polymerase produces more amplified DNA compared to a reference polymerase, such that the polymerization reaction time can be reduced, the amount of input template DNA can be reduced, the product signal from the increased DNA yield is increased, or a combination thereof. In some embodiments, the polymerization reaction time can be reduced by at least at or about 5%, 10%, 15%, 20%, 25%, 30%, 40%, 50%, or 75% using a provided recombinant and/or modified AP50 polymerase compared to a reference polymerase. In some embodiments, the required input template DNA can be reduced by at least at or about 5%, 10%, 15%, 20%, 25%, 30%, 40%, 50%, or 75% using a provided recombinant and/or modified AP50 polymerase compared to a reference polymerase. In some embodiments, the signal from the increased DNA yield is increased by at least at or about 1%, 5%, 10%, 15%, 20%, 25%, 30%, 40%, 50%, 75%, 100%, 150%, or 200% using a provided recombinant and/or modified AP50 polymerase compared to a reference polymerase. In some embodiments, the improved thermostability of the modified AP50 polymerase results in increased DNA amplification and DNA yield at temperatures, including but not limited to a temperature of at or about 5° C., 10° C., 15° C., 20° C., 25° C., 30° C., 35° C., 40° C., 45° C., 50° C., or higher. In some embodiments, the improved thermostability of the modified AP50 polymerase results in increased DNA amplification and DNA yield at elevated temperatures, including but not limited to a temperature of at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., or 55° C. In some embodiments, the provided AP50 polymerase exhibits improved kinetics compared to a reference polymerase at a temperature of at least about 42° C.

In some embodiments, the provided recombinant and/or modified AP50 polymerases amplify nucleic acids, e.g., DNA, faster compared to a reference polymerase. In some embodiments, the provided recombinant and/or modified AP50 polymerases amplify nucleic acids faster at elevated temperatures compared to a reference polymerase. In some embodiments, the increase in the rate of nucleic acid amplification is measured or assessed using a fluorescent dye. Exemplary fluorescent dyes for measuring the total product and rate of nucleic acid amplification, such as in an RCA reaction, include any described herein. In some embodiments, the modified AP50 polymerase amplifies nucleic acids, e.g., DNA, at a polymerization rate (e.g., nucleic acids, e.g., DNA, signal per unit of time) of at least at or about 1%, 5%, 10%, 15%, 20%, 25%, 30%, 40%, 50%, 75%, 100%, 150%, or 200% greater compared to a reference polymerase. In some embodiments, the modified AP50 polymerase produces between 10% and 200%, 25% and 175%, 50% and 150%, 75% and 125%, 90% and 110%, or 95% and 105% more amplified DNA in a unit of time compared to a reference polymerase. For example, a provided recombinant and/or modified AP50 polymerase produces between 100% and 200% more amplified nucleic acids, e.g., DNA, in 1 hour compared to a reference polymerase. In some embodiments, the modified AP50 polymerase amplifies nucleic acids, e.g., DNA, faster for at least 1, 2, 3, 4, 6, 8, 10, 12 hours or more compared to a reference polymerase.

In some aspects, the polymerization rate of a polymerase is the speed at which the polymerase is able to catalyze nucleotide incorporation into a growing polynucleotide strand during nucleic acid amplification, which can be described as the number of nucleotide bases incorporated per units of time (e.g., bases/second). The polymerization rate is dependent on different reaction conditions including temperature, buffer composition, substrate, substrate concentration, and time. In some embodiments, the modified AP50 polymerase described herein exhibits improved polymerization rate. In some embodiments, the modified AP50 polymerase exhibits improved polymerization rate compared to a reference polymerase. In some embodiments, the provided recombinant and/or modified AP50 polymerase is used for a nucleic acid amplification process. In some embodiments, the provided recombinant and/or modified AP50 polymerase produces more amplified nucleic acid compared to a reference polymerase. In some embodiments, the nucleic acid amplification is a RCA reaction. In some embodiments, the provided recombinant and/or modified AP50 polymerase generates a higher density of detected RCA products in an RCA reaction compared to a reference polymerase. In some embodiments, the provided recombinant and/or modified AP50 polymerase generates a higher product signal intensity in an RCA reaction compared to a reference polymerase.

In some embodiments, the provided recombinant and/or modified AP50 polymerases produce amplified nucleic acids, e.g., DNA, at a faster rate compared to a reference polymerase, such that the polymerization reaction time can be reduced and/or the product signal from the increased nucleic acids, e.g., DNA, amplification is increased. In some embodiments, the polymerization reaction time can be reduced by at least at or about 5%, 10%, 15%, 20%, 25%, 30%, 40%, 50%, or 75% using a provided recombinant and/or modified AP50 polymerase compared to a reference polymerase. In some embodiments, the amount of produced nucleic acid, e.g., DNA, or the yield of reaction product is increased at least at or about 1%, 5%, 10%, 15%, 20%, 25%, 30%, 40%, 50%, 75%, 100%, 150%, or 200% using a provided recombinant and/or modified AP50 polymerase compared to a reference polymerase. In some embodiments, the improved thermostability of the modified AP50 polymerase results in increased rate of nucleic acids amplification at a particular temperature, including but not limited to, at or about 5° C., 10° C., 15° C., 20° C., 25° C., 30° C., 35° C., 40° C., 45° C., 50° C., or higher. In some embodiments, the improved thermostability of the modified AP50 polymerase results in increased rate of nucleic acid amplification at an elevated temperature, including but not limited to, at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., or 55° C.

In some embodiments, the provided recombinant and/or modified AP50 polymerases are used to amplify nucleic acids, e.g., DNA, using a particular method, such as in a rolling-circle amplification (RCA) reaction. In some embodiments, the provided recombinant and/or modified AP50 polymerases generate a higher density of detected rolling-circle amplification (RCA) products in an RCA reaction compared to a reference polymerase. In some embodiments, determining the density of detected RCA products (RCPs) involves the use and detection of a specific fluorescent dye, wherein the density of detected RCA products is measured in RCA product counts per $\mu m^2$ sample area. In some embodiments, the density of detected RCPs is related to the total sample signal. In some embodiments, the provided recombinant and/or modified AP50 polymerase generates a higher density of detected RCPs in an RCA reaction compared to a reference polymerase. In some embodiments, the provided recombinant and/or modified AP50 polymerases produce a density of detected RCA products that is at least at or about 1%, 5%, 10%, 15%, 20%, 25%, 30%, 40%, 50%, 75%, 100%, 150%, or 200% higher compared to a reference polymerase. In some embodiments, the provided recombinant and/or modified AP50 polymerases produce a density of detected RCA products that is between 10% and 200%, 25% and 175%, 50% and 150%, 75% and 125%, 90% and 110%, or 95% and 105% higher compared to a reference polymerase.

In some embodiments, the RCA reaction is assessed or evaluated for generated RCA product signal intensity. In some aspects, the product signal intensity is calculated as a local signal intensity over a local background mean intensity. In some embodiments, the provided recombinant and/or modified AP50 polymerases generate a higher product signal intensity in an RCA reaction compared to a reference polymerase. In some embodiments, the provided recombinant and/or modified AP50 polymerases produce an RCA reaction product signal intensity at least at or about 1%, 5%, 10%, 15%, 20%, 25%, 30%, 40%, 50%, 75%, 100%, 150%, or 200% higher compared to a reference polymerase. In some embodiments, the provided recombinant and/or modified AP50 polymerases produce a RCA reaction product signal intensity at least between 10% and 200%, 25% and 175%, 50% and 150%, 75% and 125%, 90% and 110%, or 95% and 105% higher compared to a reference polymerase.

In some embodiments, an RCA reaction using the provided recombinant and/or modified AP50 polymerases is performed at a temperature of or about 5° C., 10° C., 15° C., 20° C., 25° C., 30° C., 35° C., 40° C., 45° C., 50° C., or higher. In some embodiments, the RCA reaction is performed between 5° C. and 55° C., 10° C. and 50° C., 25° C. and 45° C., 30° C. and 40° C., or 35° C. and 45° C. In some embodiments, the RCA reaction using the provided recombinant and/or modified AP50 polymerases is performed at an elevated temperature. In some embodiments, the RCA reaction is performed at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., or 55° C. In some embodiments, the RCA reaction is performed between 30° C. and 55° C., 32° C. and 53° C., 34° C. and 51° C., 36° C. and 49° C., 38° C. and 47° C., or 40° C. and 45° C.

2. Other Exemplary Features

In some aspects, the provided recombinant and/or modified AP50 polymerases exhibit other features or improvements, for example, related to the polymerase activity and applications in analyzing or assessing biological samples, such as in nucleic acid amplifications and sequencing. Examples of other improved or altered properties and features include improved or altered processivity, sensitivity, specificity, solubility, polymerization rate, product yield, increased half-life, cofactor selectivity, exonuclease activity, resistance to photodamage, strand displacing activity, exonuclease activity or reverse transcriptase activity. In some embodiments, the provided recombinant and/or modified AP50 polymerases, for example, those described in Section II.A, exhibit one or more altered or improved features (e.g., thermostability, processivity, sensitivity, specificity, solubility, and/or polymerization rate). The provided recombinant and/or modified AP50 polymerases can also exhibit two or more of the altered features in combination, or also possess additional improved or altered properties. In some aspects, the modified AP50 polymerase has strand displacing activity. In some embodiments, the features or improvements exhibited by the provided recombinant and/or variant AP50 polymerases are related to the polymerase activity in biological samples, such as a tissue sample or a section of a cell pellet or cell block.

In some aspects, polymerase processivity is the ability of a nucleic acid polymerase to carry out continuous nucleic acid synthesis on a template nucleic acid without frequent dissociation. Processivity can be measured by the average number of nucleotides incorporated by a nucleic acid polymerase on a single association-disassociation event. In some embodiments, the modified AP50 polymerase described herein exhibits improved processivity, wherein the improved processivity improves polymerase activity. In some embodiments, the modified AP50 polymerase exhibits improved processivity compared to a reference polymerase. In some embodiments, the provided recombinant and/or modified AP50 polymerase produces more amplified nucleic acid compared to a reference polymerase. In some embodiments, the provided recombinant and/or modified AP50 polymerase amplifies nucleic acid faster compared to a reference polymerase. In some embodiments, the nucleic acid amplification is a RCA reaction. In some embodiments, the provided recombinant and/or modified AP50 polymerase generates a higher density of detected RCA products in an RCA reaction compared to a reference polymerase. In some embodiments, the provided recombinant and/or modified AP50 polymerase generates a higher product signal intensity in an RCA reaction compared to a reference polymerase.

In some embodiments, the recombinant and/or modified AP50 polymerase produces at least 10%, at least 15%, at least 20%, at least 25%, or at least 30% more rolling circle amplification products than a reference polymerase under the same reaction conditions.

In some embodiments, the recombinant and/or modified AP50 polymerase produces at least at or about 1%, 5%, 10%, 15%, 20%, 25%, 30%, 40%, 50%, 75%, 100%, 150%, or 200% more amplified nucleic acid compared to a reference polymerase. In some embodiments, the recombinant and/or modified AP50 polymerase produces between 10% and 200%, 25% and 175%, 50% and 150%, 75% and 125%, 90% and 110%, or 95% and 105% more amplified nucleic acid compared to a reference polymerase. In some embodiments, the recombinant and/or modified AP50 polymerase produces more amplified nucleic acid compared to a reference polymerase, such that the polymerization reaction time can be reduced, the amount of input template nucleic acid can be reduced, the product signal from the increased nucleic acid yield is increased, or a combination thereof. In some embodiments, the recombinant and/or modified AP50 polymerase amplifies nucleic acid (e.g., product signal per unit of time) at least at or about 1%, 5%, 10%, 15%, 20%, 25%, 30%, 40%, 50%, 75%, 100%, 150%, or 200% faster compared to a reference polymerase. In some embodiments, the recombinant and/or modified AP50 polymerase ampli-fies between 10% and 200%, 25% and 175%, 50% and 150%, 75% and 125%, 90% and 110%, or 95% and 105% more nucleic acid in a unit of time compared to a reference polymerase. For example, the recombinant and/or modified AP50 polymerase produces between 100% and 200% more amplified nucleic acid in 1 hour compared to a reference polymerase. In some embodiments, the recombinant and/or modified AP50 polymerase exhibiting improved thermostability amplifies nucleic acid faster for at least 1, 2, 3, 4, 6, 8, 10, 12 hours or more compared to a reference polymerase. In some embodiments, the recombinant and/or modified AP50 polymerase produces amplified nucleic acid at a faster rate compared to a reference polymerase, such that the polymerization reaction time can be reduced, the product signal from the increased nucleic acid amplification rate is increased, or a combination thereof.

In some embodiments, the recombinant and/or modified AP50 polymerase exhibiting one or more altered features (e.g., thermostability, processivity, sensitivity, specificity, solubility, and/or polymerization rate) described herein is used for a nucleic acid amplification process, wherein the nucleic acid amplification is a RCA reaction. In some embodiments, the recombinant and/or modified AP50 polymerase produces a density of detected RCA products at least at or about 1%, 5%, 10%, 15%, 20%, 25%, 30%, 40%, 50%, 75%, 100%, 150%, or 200% higher compared to a reference polymerase. In some embodiments, the recombinant and/or modified AP50 polymerase described herein produces density of detected RCA products at least between 10% and 200%, 25% and 175%, 50% and 150%, 75% and 125%, 90% and 110%, or 95% and 105% higher compared to a reference polymerase. In some embodiments, the recombinant and/or modified AP50 polymerase described herein produces a product signal intensity at least at or about 1%, 5%, 10%, 15%, 20%, 25%, 30%, 40%, 50%, 75%, 100%, 150%, or 200% higher compared to a reference polymerase. In some embodiments, the recombinant and/or modified AP50 polymerase described herein produces a product signal intensity at least between 10% and 200%, 25% and 175%, 50% and 150%, 75% and 125%, 90% and 110%, or 95% and 105% higher compared to a reference polymerase.

In some embodiments, the provided recombinant and/or modified AP50 polymerase described herein further exhibits a longer half-life in the absence of substrate compared to a reference polymerase. In some embodiments, the provided recombinant and/or modified AP50 polymerase described herein further exhibits a longer half-life in the absence of substrate compared to a wild-type AP50 polymerase. In some embodiments, the provided recombinant and/or modified AP50 polymerase described herein further exhibits a longer half-life in the presence of substrate compared to a reference polymerase. In some embodiments, the provided recombinant and/or modified AP50 polymerase is more stable in the presence and absence of substrate compared to a reference polymerase. In some embodiments, the modified AP50 polymerase substrate comprises a nucleotide, a nucleotide derivative, a polynucleotide, or a combination thereof. In some embodiments, the modified AP50 polymerase exhibits an extended half-life that is or about 5%, 10%, 15%, 20%, 25%, 30%, 40%, 50%, 75%, 100%, 150%, 200%, 300%, 400%, or 500% longer compared to a reference polymerase in the presence or absence of substrate. In some embodiments, the provided recombinant and/or modified AP50 polymerase described herein exhibits an extended half-life between 5% and 500%, 15% and 300%, 50% and 400%, 30% and 100%, 20% and 200%, 40% and 150%, 75% and 400%, or 50% and 300% longer compared to a reference polymerase in the presence or absence of substrate.

In some aspects described herein, the reference polymerase is a wild-type Phi29 polymerase of SEQ ID NO:5. In some aspects described herein, the reference polymerase is a wild-type AP50 polymerase of SEQ ID NO:1.

III. NUCLEIC ACIDS, VECTORS AND EXPRESSION SYSTEMS

Also provided herein are polynucleotides, vectors, and expression systems encoding any of the provided recombinant AP50 polymerases and modified AP50 polymerases, for example, those described in Section II. In some aspects, the provided polynucleotides, vectors, and expression systems can be used to generate the provided recombinant AP50 polymerases and modified AP50 polymerases.

The nucleic acids may include those encompassing natural and/or non-naturally occurring nucleotides and bases, e.g., including those with backbone modifications. The terms "nucleic acid molecule," "nucleic acid," and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

In some embodiments, the modified AP50 polymerases may be a recombinantly produced variant of the natural protein in which one or more property, such as thermostability, has been altered. In some aspects, the nucleic acid is synthetic. In some aspects, the nucleic acid molecule can be modified (e.g., codon optimization) for use in the constructs described herein. In some cases, the sequences can be designed to contain terminal restriction site sequences for purposes of cloning into vectors.

A. Polynucleotides

In some embodiments, provided herein are polynucleotides encoding a recombinant AP50 polymerase. In some embodiments, provided herein are polynucleotides encoding a modified AP50 polymerase. In some embodiments, the polynucleotides encoding modified AP50 polymerases comprise one or more amino acid modifications or variations (e.g., deletions, insertions, substitutions, and/or combinations thereof) compared to the sequence of the wild-type AP50 polymerase. In some embodiments, the polynucleotides encode any of the provided recombinant and/or modified AP50 polymerases described herein, such as those described in Section II.

Amino acid sequence variants of a modified and/or recombinant AP50 polymerase may be prepared by introducing appropriate modifications into the nucleotide sequence encoding the wild-type AP50 polymerase. Such modifications include, for example, deletions from and/or insertions into and/or substitutions of residues within the nucleotide sequences encoding the wild-type AP50 polymerase. The encoded modified AP50 polymerase can comprise any combination of deletion, insertion, and substitutions. In some aspects, the encoded modified AP50 polymerase exhibits desired characteristics, e.g., improved polymerase activity, features and/or properties.

In some aspects, provided herein is a polynucleotide encoding a modified AP50 polymerase comprising SEQ ID NO:6 (does not include the initial fMet residue). In some aspects, provided herein is a polynucleotide encoding an AP50 polymerase comprising SEQ ID NO:1 (does not include the initial fMet residue). In some aspects, provided herein is a polynucleotide encoding a modified AP50 polymerase comprising an amino acid deletion of at least 1, 5, 10, 25, 50, 75, or 100 amino acids, with reference to the positions of SEQ ID NO:1. In some embodiments, the encoded modified AP50 polymerase comprises at least at or about 90%, 95%, 96%, 97%, 98%, 99%, or 99.5% sequence identity to SEQ ID NO:6. In some embodiments, the encoded modified AP50 polymerase comprises at least at or about 90%, 95%, 96%, 97%, 98%, 99%, or 99.5% sequence identity to SEQ ID NO:1. In some aspects, provided herein is a polynucleotide encoding a modified AP50 polymerase further comprising one or more heterologous sequences, for example, a tag and/or a linker.

In some aspects, provided herein is a polynucleotide encoding a modified AP50 polymerase comprising SEQ ID NO:32 (includes the initial fMet residue). In some aspects, provided herein is a polynucleotide encoding an AP50 polymerase comprising SEQ ID NO:27 (includes the initial fMet residue). In some aspects, provided herein is a polynucleotide encoding a modified AP50 polymerase comprising an amino acid deletion of at least 1, 5, 10, 25, 50, 75, or 100 amino acids, with reference to the positions of SEQ ID NO:27. In some embodiments, the encoded modified AP50 polymerase comprises at least at or about 90%, 95%, 96%, 97%, 98%, 99%, or 99.5% sequence identity to SEQ ID NO:32. In some embodiments, the encoded modified AP50 polymerase comprises at least at or about 90%, 95%, 96%, 97%, 98%, 99%, or 99.5% sequence identity to SEQ ID NO:27. In some aspects, provided herein is a polynucleotide encoding a modified AP50 polymerase further comprising one or more heterologous sequences, for example, a tag and/or a linker.

In some aspects, provided are polynucleotide sequences encoding any of the provided modified AP50 polymerases, such as any of those described in Section II. In some aspects, the encoded modified AP50 polymerases exhibits or possesses one or more of the exemplary features or properties, such as any of those described in Section II.B.

In some embodiments, provided are polynucleotide sequences encoding a modified AP50 polymerase set forth in any of SEQ ID NOS:1-4 and 6. In some embodiments, provided are polynucleotide sequences encoding the modified AP50 polymerase set forth in SEQ ID NO:1. In some embodiments, provided are polynucleotide sequences encoding the modified AP50 polymerase set forth in SEQ ID NO:2. In some embodiments, provided are polynucleotide sequences encoding the modified AP50 polymerase set forth in SEQ ID NO:3. In some embodiments, provided are polynucleotide sequences encoding the modified AP50 polymerase set forth in SEQ ID NO:4. In some embodiments, provided are polynucleotide sequences encoding the modified AP50 polymerase set forth in SEQ ID NO:6.

In some embodiments, provided are polynucleotide sequences encoding a modified AP50 polymerase set forth in any of SEQ ID NOS:27-30 and 32. In some embodiments, provided are polynucleotide sequences encoding the modified AP50 polymerase set forth in SEQ ID NO:27. In some embodiments, provided are polynucleotide sequences encoding the modified AP50 polymerase set forth in SEQ ID NO:28. In some embodiments, provided are polynucleotide sequences encoding the modified AP50 polymerase set forth in SEQ ID NO:29. In some embodiments, provided are polynucleotide sequences encoding the modified AP50 polymerase set forth in SEQ ID NO:30. In some embodiments, provided are polynucleotide sequences encoding the modified AP50 polymerase set forth in SEQ ID NO:32.

In some embodiments, the polynucleotide comprises any one of SEQ ID NOS:17-21, or a sequence that has at least at or about 90%, 95%, 96%, 97%, 98%, 99%, or 99.5% sequence identity to any one of SEQ ID NOS:17-21. In some embodiments, the polynucleotide comprises SEQ ID NO:17, or a sequence that has at least at or about 90%, 95%, 96%, 97%, 98%, 99%, or 99.5% sequence identity to SEQ ID NO:17. In some embodiments, the polynucleotide comprises SEQ ID NO:17. In some embodiments, the polynucleotide comprises SEQ ID NO:18, or a sequence that has at least at or about 90%, 95%, 96%, 97%, 98%, 99%, or 99.5% sequence identity to SEQ ID NO:18. In some embodiments, the polynucleotide comprises SEQ ID NO:18. In some embodiments, the polynucleotide comprises SEQ ID NO:19, or a sequence that has at least at or about 90%, 95%, 96%, 97%, 98%, 99%, or 99.5% sequence identity to SEQ ID NO:19. In some embodiments, the polynucleotide comprises SEQ ID NO:19. In some embodiments, the polynucleotide comprises SEQ ID NO:20, or a sequence that has at least at or about 90%, 95%, 96%, 97%, 98%, 99%, or 99.5% sequence identity to SEQ ID NO:20. In some embodiments, the polynucleotide comprises SEQ ID NO:20. In some embodiments, the polynucleotide comprises SEQ ID NO:21, or a sequence that has at least at or about 90%, 95%, 96%, 97%, 98%, 99%, or 99.5% sequence identity to SEQ ID NO:21. In some embodiments, the polynucleotide comprises SEQ ID NO:21.

In some embodiments, the polynucleotide comprises any one of SEQ ID NOS:33-37, or a sequence that has at least at or about 90%, 95%, 96%, 97%, 98%, 99%, or 99.5% sequence identity to any one of SEQ ID NOS:33-37. In some embodiments, the polynucleotide comprises SEQ ID NO:33, or a sequence that has at least at or about 90%, 95%, 96%, 97%, 98%, 99%, or 99.5% sequence identity to SEQ ID NO:33. In some embodiments, the polynucleotide comprises SEQ ID NO:33. In some embodiments, the polynucleotide comprises SEQ ID NO:34, or a sequence that has at least at or about 90%, 95%, 96%, 97%, 98%, 99%, or 99.5% sequence identity to SEQ ID NO:34. In some embodiments, the polynucleotide comprises SEQ ID NO:34. In some embodiments, the polynucleotide comprises SEQ ID NO:35, or a sequence that has at least at or about 90%, 95%, 96%, 97%, 98%, 99%, or 99.5% sequence identity to SEQ ID NO:35. In some embodiments, the polynucleotide comprises SEQ ID NO:35. In some embodiments, the polynucleotide comprises SEQ ID NO:36, or a sequence that has at least at or about 90%, 95%, 96%, 97%, 98%, 99%, or 99.5% sequence identity to SEQ ID NO:36. In some embodiments, the polynucleotide comprises SEQ ID NO:36. In some embodiments, the polynucleotide comprises SEQ ID NO:37, or a sequence that has at least at or about 90%, 95%, 96%, 97%, 98%, 99%, or 99.5% sequence identity to SEQ ID NO:37. In some embodiments, the polynucleotide comprises SEQ ID NO:37.

In some embodiments, the polynucleotide sequences encoding the provided modified AP50 polymerases is codon-optimized for a host cell or a recombinant expression system to generate the modified AP50 polymerase. Typically, codon optimization involves balancing the percentages of codons selected with the published abundance of transfer RNAs appropriate for the host cell or expression system so that none is overloaded or limiting. This may be necessary in some cases because most amino acids are encoded by more than one codon, and codon usage varies from organism to organism. Differences in codon usage between transfected genes and host cells can have effects on protein expression and immunogenicity of a nucleic acid construct. In general, for codon optimization, codons are chosen to select for those codons that are in balance with the host cell usage frequency. Typically, the redundancy of the codons for amino acids is such that different codons code for one amino acid. In some embodiments, in selecting a codon for replacement, it may be desired that the resulting mutation is a silent mutation such that the codon change does not affect the amino acid sequence. Generally, the last nucleotide of the codon can remain unchanged without affecting the amino acid sequence.

B. Recombinant Nucleic Acids and Vectors

In some aspects, provided herein are recombinant nucleic acids comprising polynucleotides encoding any of the described recombinant and/or modified AP50 polymerases, such as those described in Section II, or any of the described polynucleotides, such as those described in Section III.A. In some aspects, also provided herein are vectors comprising polynucleotides encoding any of the described recombinant and/or modified AP50 polymerases, such as those described in Section II, or any of the described polynucleotides, such as those described in Section III.A. In some embodiments, the recombinant nucleic acids and vectors comprise a polynucleotides encoding any of the recombinant and/or modified AP50 polymerases described herein, for example, that comprises one or more amino acid modifications or variations, e.g., deletions, insertions, and/or substitutions compared to the sequence of the wild-type AP50 polymerase.

In some embodiments, the recombinant nucleic acid molecule comprises a polynucleotide described in Section III.A.

In some embodiments, the recombinant nucleic acid molecule further comprises a transcription regulatory sequence operatively linked with the polynucleotide. In some embodiments, the transcription regulatory sequence comprises a promoter selected from among a bacterial, viral, and mammalian promoter. In some embodiments, the promoter can be a non-viral promoter or a viral promoter, such as a cytomegalovirus (CMV) promoter, a T7 promoter, an SV40 promoter, an RSV promoter, and a promoter found in the long-terminal repeat of the murine stem cell virus. Other promoters known to a skilled artisan also are contemplated.

In some embodiments, a vector is provided comprising polynucleotides encoding any of the described recombinant and/or modified AP50 polymerases, such as those described in Section II, or any of the described polynucleotides, such as those described in Section III.A, or a recombinant nucleic acid molecule described herein, such as those encoding any of the modified AP50 polymerases described herein. In some embodiments, the vector is a plasmid, a phagemid, a viral vector, a cosmid, or a transposon. The expression vector can be any suitable recombinant expression vector, and can be used to transform or transfect any suitable host. Suitable vectors include those designed for propagation and expansion or for expression or both, such as plasmids and viruses. In some embodiments, the vector is an expression vector. Exemplary vectors can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAMneo (Clontech). In some cases, the vector is a viral vector. In some such aspects, the viral vector is a retroviral vector, such as a lentiviral vector.

C. Host Cells and Expression Systems

In some instances, provided herein are host cells or recombinant expression systems comprising any of the polynucleotides, recombinant nucleic acid molecules, or vectors provided herein, such as any that are described in Section III. In some embodiments, the polynucleotide, the recombinant nucleic acid molecule, and/or the vector is for use in transforming the host cell or recombinant expression system to generate a transformed host cell or recombinant expression system.

The polynucleotide, the recombinant nucleic acid molecule, and/or the vector can be introduced into the host cell or recombinant expression system using various methods for introduction or transfer of nucleic acids, including via viral, e.g., retroviral or lentiviral, transduction, transposons, and electroporation. In some aspects, the recombinant expression system comprises a host cell, such as any host cells described herein.

In some embodiments, the transformed host cell or recombinant expression system generates a recombinant AP50 polymerase or a modified AP50 polymerase. In some embodiments, the host cell or recombinant expression system is used to produce the recombinant AP50 polymerase or the modified AP50 polymerase. In some embodiments, the host cell or recombinant expression system is a cell system or a cell-free system. In some embodiments, the host cell or recombinant expression system comprises one or more cell systems selected from among a bacterial cell, a fungal cell, an insect cell, and a mammalian cell. In some embodiments, a cell system may be selected from a group comprising *E. coli, S. cerevisiae, D. melanogaster*, and CHO cells. For example, *E. coli* is a bacterial cell that can be transformed with the polynucleotide, recombinant nucleic acid, and/or vector described herein for effective production of a modified AP50 polymerase. In some aspects, in a bacterial host cell or expression system, such as *E. coli*, protein translation is initiated with N-formyl-methionine (fMet), which during translation initiation is brought to the ribosome in the form of fMet-tRNA$^{fMet}$. In some aspects, the formylated methionine at the N-terminus of nascent bacterial proteins is typically removed co-translationally shortly after the nascent protein has emerged from the peptide exit tunnel of the ribosome, by peptide deformylase (PDF), and in the majority of cases, is followed by methionine excision by methionine aminopeptidase (MAP). Accordingly, in some aspects, bacterially produced proteins does not include an initial Met residue.

In some embodiments, the polynucleotide sequence encoding the recombinant AP50 polymerase or the modified AP50 polymerase is codon-optimized for the host cell or recombinant expression system, for example, as described in Section III.A.

IV. METHODS OF USING AND USES OF RECOMBINANT AND/OR MODIFIED AP50 POLYMERASES AND APPLICATIONS

Also provided herein are methods that involve or employ any of the provided recombinant and/or modified AP50 polymerases, compositions or kits that include a recombinant and/or modified AP50 polymerase, or nucleic acids or vectors that encode the recombinant and/or modified AP50 polymerases, and uses of any of the foregoing, such as for nucleic acid amplification and/or sequencing. In some aspects, the provided recombinant and/or modified AP50 polymerases are used in a variety analysis or assessment methods or experiments (e.g., sequencing, genotyping, and amplification reactions), for assessing a biological sample. In some aspects, the provided recombinant and/or modified AP50 polymerases are used in amplifying nucleic acids, e.g., DNAs or RNAs, including in applications such as rolling circle amplification (RCA).

In some aspects, provided are methods for amplifying nucleic acids, such as DNA, that involve contacting a biological sample containing DNA to be amplified with any of the provided recombinant and/or modified AP50 polymerases and uses thereof, compositions or kits that include a recombinant and/or modified AP50 polymerase, or nucleic acids or vectors that encode the recombinant and/or modified AP50 polymerases.

In some aspects, provided are methods of performing a rolling circle amplification (RCA) that involves the use of any of the provided recombinant and/or modified AP50 polymerases, compositions or kits that include a recombinant and/or modified AP50 polymerase, or nucleic acids or vectors that encode the recombinant and/or modified AP50 polymerases. In some aspects, the method of performing RCA involves contacting a biological sample containing nucleic acids, e.g., DNA, to be amplified with any of the provided recombinant and/or modified AP50 polymerases, compositions or kits that include a recombinant and/or modified AP50 polymerase, or nucleic acids or vectors that encode the recombinant and/or modified AP50 polymerases. In some aspects, the methods thereby amplify the nucleic acid by RCA.

In some embodiments, the provided recombinant and/or modified AP50 polymerases are used in methods that involve the amplification of a nucleic acid probe through rolling circle amplification. In some embodiments, RCA involves the use of primary probes that recognize particular target nucleic acid sequences, and can be amplified via RCA to be detected. In some embodiments, the primary probes, such as a circularizable probe or a probe set, may contain one or more barcodes. In some embodiments, the barcodes are bound by detection probes, which do not need to be fluorescent, but that include a target-binding portion (e.g., for hybridizing to one or more primary probes) and multiple other barcodes (e.g., secondary barcodes, versus the primary barcodes on the primary probes). In some embodiments, the barcodes of the detection probes are targeted by detectably labeled detection oligonucleotides, such as fluorescently labeled oligonucleotides. In some embodiments, one or more decoding schemes are used to decode the signals, such as fluorescence, for sequence determination. Exemplary decoding schemes are described in Eng et al., *Nature* 2019; 568(7751):235-239; Chen et al., *Science;* 2015; 348(6233): aaa6090; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, the provided recombinant and/or modified AP50 polymerases are used in methods that involve using a circular or circularizable construct hybridized to the nucleic acid of interest to generate a circular nucleic acid. In some embodiments, the RCA comprises a linear RCA. In some embodiments, the RCA comprises a branched RCA. In some embodiments, the RCA comprises a dendritic RCA. In some embodiments, the RCA comprises any combination of the foregoing. In some embodiments, the circular nucleic acid is a construct formed using ligation. In some embodiments, the circular construct is formed using template primer extension followed by ligation. In some embodiments, the circular construct is formed by providing an insert between ends to be ligated. In some embodiments, the circular construct is formed using a combination of any of the foregoing. In some embodiments, the ligation is a DNA-DNA templated ligation. In some embodiments, the ligation is an RNA-RNA templated ligation. Exemplary RNA-templated ligation probes and methods are described in US 2020/0224244 which is incorporated herein by reference in its entirety. In some embodiments, the ligation is a RNA-DNA templated ligation. In some embodiments, a splint is provided as a template for ligation.

In some embodiments, the provided recombinant and/or modified AP50 polymerases are used in methods that involve using a probe (e.g., a circularizable probe such as a padlock probe) that comprises a 5' flap which may be recognized by a structure-specific cleavage enzyme, e.g. an enzyme capable of recognizing the junction between single-stranded 5' overhang and a DNA duplex, and cleaving the single-stranded overhang. It will be understood that the branched three-strand structure which is the substrate for the structure-specific cleavage enzyme may be formed by 5' end of one probe part and the 3' end of another probe part when both have hybridized to the target nucleic acid molecule, as well as by the 5' and 3' ends of a one-part probe. Enzymes suitable for such cleavage include Flap endonucleases (FENS), which are a class of enzymes having endonucleolytic activity and being capable of catalyzing the hydrolytic cleavage of the phosphodiester bond at the junction of single- and double-stranded DNA. Thus, in some embodiments, cleavage of the additional sequence 5' to the first target-specific binding site is performed by a structure-specific cleavage enzyme, e.g., a Flap endonuclease. Suitable Flap endonucleases are described in Ma et al., *JBC* 2000; 275:24693-24700 and in US 2020/0224244 and may include *P. furiosus* (Pfu), *A. fulgidus* (Afu), *M. jannaschii* (Mja) or *M. thermoautotrophicum* (Mth). In some embodiments an enzyme capable of recognizing and degrading a single-stranded oligonucleotide having a free 5' end may be used to cleave an additional sequence (e.g., 5' flap) from a structure as described above. Thus, an enzyme having 5' nuclease activity may be used to cleave a 5' additional sequence. Such 5' nuclease activity may be 5' exonuclease and/or 5' endonuclease activity. A 5' nuclease enzyme is capable of recognizing a free 5' end of a single-stranded oligonucleotide and degrading said single-stranded oligonucleotide. A 5' exonuclease degrades a single-stranded oligonucleotide having a free 5' end by degrading the oligonucleotide into constituent mononucleotides from its 5' end. A 5' endonuclease activity may cleave the 5' flap sequence internally at one or more nucleotides. Further, a 5' nuclease activity may take place by the enzyme traversing the single-stranded oligonucleotide to a region of duplex once it has recognized the free 5' end, and cleaving the single-stranded region into larger constituent nucleotides (e.g., dinucleotides or trinucleotides), or cleaving the entire 5' single-stranded region, e.g. as described in Lyamichev et al., *PNAS* 1999; 96, 6143-6148 for Taq DNA polymerase and the 5' nuclease thereof. Preferred enzymes having 5' nuclease activity include Exonuclease VIII, or a native or recombinant DNA polymerase enzyme from *Thermus aquaticus* (Taq), *Thermus thermophilus* or *Thermus flavus*, or the nuclease domain therefrom.

Following formation of the circular nucleic acid, in some instances, an amplification primer is added. In some instances, the amplification primer is added with the primary and/or secondary probes. In some instances, the amplification primer may also be complementary to the target nucleic acid and the padlock probe (e.g., a SNAIL probe). In some embodiments, a washing step is performed to remove any unbound probes, primers, etc. In some embodiments, the wash is a stringency wash. Washing steps can be performed at any point during the process to remove non-specifically bound probes, probes that have ligated, etc.

In some instances, upon addition of a DNA polymerase in the presence of appropriate dNTP precursors and other cofactors, the amplification primer is elongated by replication of multiple copies of the template. The amplification step can utilize isothermal amplification or non-isothermal amplification. In some embodiments, after the formation of the hybridization complex and any subsequent circularization (such as ligation of a circularizable probe or probe set to generate a circularized probe) the circular or circularized probe is rolling-circle amplified to generate a RCA product (RCP) containing multiple copies of the RCP.

Following amplification, the sequence of the amplicon (e.g., RCA product) or a portion thereof, is determined or otherwise analyzed, for example by using detectably labeled probes and imaging. The sequencing or analysis of the amplification products can comprise sequencing by hybridization, sequencing by ligation, and/or fluorescent in situ sequencing, and/or wherein the in situ hybridization comprises sequential fluorescent in situ hybridization. In some instances, a sequence of the RCA product is detected using, e.g., the secondary and higher order probes and detection oligonucleotides described herein.

In some instances, the provided recombinant and/or modified AP50 polymerases can be used in methods for amplifying a DNA, such as a sequencing method, a genotyping method, or an amplification method. In some embodiments, the methods involve contacting a biological sample containing DNA to be amplified with any of the provided recombinant and/or modified AP50 polymerases, any compositions or kits that include a recombinant and/or modified AP50 polymerase, or nucleic acids or vectors that encode the recombinant and/or modified AP50 polymerases. In some embodiments, the method also involve incubating the biological sample and the recombinant and/or modified AP50 polymerase, compositions or kits that include a recombinant and/or modified AP50 polymerase, or nucleic acids or vectors that encode the recombinant and/or modified AP50 polymerases.

In some embodiments, the biological sample containing DNA to be amplified with the recombinant and/or modified AP50 polymerase is an isolated or synthetic nucleic acids. In some embodiments, the biological sample is tested in vitro. In some embodiments, the biological sample is an organ or a tissue sample. In some embodiments, the biological sample is tested in situ, for example, wherein the recombinant and/or modified AP50 polymerase is added to a freshly or previously prepared tissue sample for target gene analysis within a tissue slice. In some embodiments, the DNA is amplified by a rolling circle amplification (RCA) as described in this section. In some embodiments, the DNA is amplified by in situ RCA in the biological sample.

In some instances, the provided recombinant and/or modified AP50 polymerases can be used in methods of performing a rolling circle amplification (RCA). In some embodiments, the methods involve contacting a biological sample containing DNA to be amplified with the recombinant and/or modified AP50 polymerase, any compositions or kits that include a recombinant and/or modified AP50 polymerase, or nucleic acids or vectors that encode the recombinant and/or modified AP50 polymerases. In some embodiments, the methods also involve incubating the biological sample and the recombinant and/or modified AP50 polymerase, any compositions or kits that include a recombinant and/or modified AP50 polymerase, or nucleic acids or vectors that encode the recombinant and/or modified AP50 polymerases. In some embodiments, the recombinant and/or modified AP50 polymerase used in the method of RCA can be any of those described in Section II.

In some embodiments, the method of RCA comprises incubating the biological sample and the recombinant and/or modified AP50 polymerase at a specific temperature. In some embodiments, the temperature is optimal for maximizing activity of the recombinant and/or modified AP50 polymerase. In some embodiments, the recombinant and/or modified AP50 polymerase and the biological sample are incubated at a temperature of at or about 5° C., 10° C., 15° C., 20° C., 25° C., 30° C., 35° C., 40° C., 45° C., 50° C., or higher. In some embodiments, the recombinant and/or modified AP50 polymerase and the biological sample are incubated at a temperature between 5° C. and 55° C., 10° C. and 50° C., 25° C. and 45° C., 30° C. and 40° C., or 35° C. and 42° C. In some embodiments, the recombinant and/or modified AP50 polymerase and the biological sample are incubated at an elevated temperature. In some embodiments, the recombinant and/or modified AP50 polymerase and the biological sample are incubated at or about 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., or 55° C. In some embodiments, the recombinant and/or modified AP50 polymerase and the biological sample are incubated between 30° C. and 55° C., 32° C. and 53° C., 34° C. and 51° C., 36° C. and 49° C., 38° C. and 47° C., or 40° C. and 45° C.

In some embodiments, RCA is performed during incubation of the recombinant and/or modified AP50 polymerase and the biological sample. In some embodiments, the RCA is performed for about 0.25, 0.5, 0.75, 1, 1.5, 2, 2.5, 3, 4, 5, 6, 8, 10, 12, 14, 16, 18, 20, 22, or 24 hours. In some embodiments, the RCA is performed for 0.25, 0.5, 0.75, 1, 1.5, 2, 2.5, 3, 4, 5, 6, 8, 10, 12, 14, 16, 18, 20, 22, or 24 hours. In some embodiments, the RCA is performed for at or about 15 minutes, 30 minutes, 45 minutes, 1 hour, 2 hours, 3 hours, 6 hours, 12 hours, or longer. In some embodiments, the RCA is performed for more than 24 hours. In some embodiments, the RCA is performed for between 1 hour and 8 hours, 0.25 hour and 12 hours, 4 hour and 24 hours, 2 hour and 16 hours, 3 hour and 10 hours, 4 hour and 18 hours, 5 hour and 14 hours, or 0.5 hour and 20 hours. In some embodiments, RCA is performed for no more than 12 hours. In some embodiments, RCA is performed for no more than 8 hours. In some embodiments, RCA is performed for no more than 6 hours. In some of any of the embodiments herein, the RCA can be performed for no more than about 15 minutes, 30 minutes, 45 minutes, 1 hour, 2 hours, or 3 hours. In some embodiments, the incubation time used is sufficient to generate a detectable amount of an RCA product.

In some embodiments, the method of performing RCA further comprises detecting the amplification product. In some embodiments, the amplification product is an RCA product (RCP). In some embodiments, the amplification product is detected by contacting the biological sample with a fluorescent dye or affinity molecule. In some embodiments, the biological sample is contacted with a fluorescent dye or affinity molecule before initiating the RCA reaction.

In some embodiments, the amplification product is detected by contacting the biological sample with SYBR gold or SYBR green. SYBR dyes are asymmetrical cyanine dyes used for staining double-stranded DNA, single-stranded DNA, and RNA molecules. In some embodiments, the amplification product is detected by contacting the biological sample with ATTO-532 (Rhodamine 6G). In some embodiments, the amplification product is detected in real time during the amplification.

In some embodiments, the provided methods employ a recombinant and/or modified AP50 polymerase that exhibits one or more of any of the features described herein, such as those described in Section II.B.

Provided herein is a method for analysis comprising: contacting a sample with a nucleic acid probe that hybridizes to a target nucleic acid (e.g., an RNA), wherein the nucleic acid probe is a circular probe or a circularizable probe comprising one or more barcodes; generating an amplification product by contacting the sample with a recombinant *Bacillus* phage AP50 polymerase; and detecting a sequence of the amplification product. In some embodiments, the detecting of the sequence of the amplification product comprises contacting the biological sample with one or more detectably-labeled probes that directly or indirectly bind to the one or more barcode sequences or complements thereof in the amplification product, and detecting signals associated with the one or more detectably-labeled probes. In some embodiments, the one or more detectably-labeled probes indirectly bind to the one or more barcode sequences or complements thereof via one or more intermediate probes that bind to the one or more barcode sequences or complements thereof, wherein the one or more intermediate probes are detectable using one or more detectably-labeled probes.

A. Samples

A sample, such as a biological sample, that can be assessed or analyzed using any of the recombinant and/or modified AP50 polymerases, compositions or kits that include a recombinant and/or modified AP50 polymerase, or nucleic acids or vectors that encode the recombinant and/or modified AP50 polymerases as provided herein, can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can include nucleic acids (such as DNA or RNA), proteins/polypeptides, carbohydrates, and/or lipids. The biological sample can be obtained as a tissue sample, such as a tissue section, biopsy, a core biopsy, a cell pellet, a cell block, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample comprises cells which are deposited on a surface. In some embodiments, the biological sample is a tissue sample. In some embodiments, the tissue sample is an intact tissue sample or a non-homogenized tissue sample.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix comprises a network of natural molecules and/or synthetic molecules that are chemically and/or enzymatically linked, e.g., by crosslinking. In some embodiments, a 3D matrix comprises a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

B. Analytes

The methods and compositions provided herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template using any of the AP50 polymerases described herein (e.g. a circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

1. Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labeling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

2. Labeling Agents

In some embodiments, the methods and compositions provided herein can be used for analyzing endogenous analytes (e.g., RNA, ssDNA, cell surface or intracellular proteins and/or metabolites) in a sample using one or more labeling agents. In some embodiments, an analyte labeling agent may include an agent that interacts with an analyte (e.g., an endogenous analyte in a sample). In some embodiments, the labeling agents can comprise a reporter oligonucleotide that is indicative of the analyte or portion thereof interacting with the labelling agent. For example, the reporter oligonucleotide comprises a barcode sequence that permits identification of the labeling agent. In some cases, the sample contacted by the labelling agent can be further contacted with a probe (e.g., a single-stranded probe sequence), that hybridizes to a reporter oligonucleotide of the labeling agent, in order to identify the analyte associated with the labeling agent. In some embodiments, the analyte labeling agent comprises an analyte binding moiety and a labeling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method involves one or more post-fixing (also referred to as post-fixation) steps after contacting the sample with one or more labeling agents.

In the methods and systems described herein, one or more labeling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labeling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labeling agents can include (e.g., are attached to) a reporter oligonucleotide that is indicative of the cell surface feature to which the binding group binds. For example, the reporter oligonucleotide comprises a barcode sequence that permits identification of the labeling agent. For example, a labeling agent that is specific to one type of cell feature (e.g., a first cell surface feature) may have coupled thereto a first reporter oligonucleotide, while a labeling agent that is specific to a different cell feature (e.g., a second cell surface feature) may have a different reporter oligonucleotide coupled thereto. For a description of exemplary labeling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labeling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labeling agents are the same. In some embodiments in which the plurality of analytes includes a single species of analyte, the analyte binding moieties of the plurality of analyte labeling agents are the different (e.g., members of the plurality of analyte labeling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labeling agent that is specific to a particular cell feature may have a first plurality of the labeling agent (e.g., an antibody or lipophilic moiety) coupled to a first reporter oligonucleotide and a second plurality of the labeling agent coupled to a second reporter oligonucleotide.

In some aspects, these reporter oligonucleotides comprises nucleic acid barcode sequences that permit identification of the labeling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using the in situ detection techniques described herein.

Attachment (coupling) of the reporter oligonucleotides to the labeling agents may be achieved through any of a variety of direct or indirect, covalent or non-covalent associations or attachments. For example, oligonucleotides may be covalently attached to a portion of a labeling agent (such a protein, e.g., an antibody or antibody fragment) using chemical conjugation techniques (e.g., Lightning-Link® antibody labeling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labeling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labeling agents. Commercially available kits, such as those from Thunderlink and Abcam, and techniques common in the art may be used to couple reporter oligonucleotides to labeling agents as appropriate. In another example, a labeling agent is indirectly (e.g., via hybridization) coupled to a reporter oligonucleotide comprising a barcode sequence that identifies the label agent. For instance, the labeling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labeling agent to the reporter oligonucleotide. In some embodiments, the reporter oligonucleotides are releasable from the labeling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein.

In some cases, the labeling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labeling agent (or reporter oligonucleotide) either directly or indirectly (e.g., the label can be conjugated to a molecule that can bind to the labeling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labeling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

3. Products of Endogenous Analyte and/or Labeling Agent

In some embodiments, provided herein are methods and compositions for analyzing one or more products of an endogenous analyte and/or a labeling agent in a biological sample. In some embodiments, an endogenous analyte (e.g., a viral or cellular DNA or RNA) or a product (e.g., an amplification product or an extension product, for example, by a nucleic acid polymerase), a replication product, a transcription/reverse transcription product, and/or an amplification product such as a rolling circle amplification (RCA product) thereof is analyzed. In some embodiments, a labeling agent that directly or indirectly binds to an analyte in the biological sample is analyzed. In some embodiments, a product (e.g., an amplification product such as a rolling circle amplification (RCA product) generated using any of the AP50 polymerases provided in Section II, an extension product (e.g., by a nucleic acid polymerase), a hybridization product, a ligation product, a replication product, a transcription/reverse transcription product), and/or of a labeling agent that directly or indirectly binds to an analyte in the biological sample is analyzed.

C. Detection and Analysis

In some aspects, provided herein are methods comprising in situ assays, such as an in situ assay that involves the use of any of the recombinant and/or modified AP50 polymerases provided herein. In some aspects, the in situ assays involve generation of the amplification product in situ, for example using any of the recombinant and/or modified AP50 polymerases or compositions provided herein, and detection of the amplified product in situ, for example, using microscopy or other detection or determination methods involving an optical readout. In other aspects, the nucleic acid amplification and/or detection is performed in vitro.

In some aspects, detection or determination of a sequence of a target nucleic acid or amplification product thereof is performed in situ in a cell in an intact tissue. In some aspects, the methods involve in situ generation of nucleic acid amplification product, such as an rolling circle amplification (RCA) product using recombinant and/or modified AP50 polymerases provided herein, and detecting the amplification products.

In some embodiments, the method involves imaging the sample to detect a signal associated with a detection probe (e.g., detectably labeled detection oligonucleotides or detectably-labeled probes, such as fluorescently labeled oligonucleotides) hybridized in the sample. In some embodiments, the probe (e.g., primary probe or amplification product generated using the primary probe) comprises one or more barcode sequences for detection. In some embodiments, the signal can be amplified in situ in the sample. In some embodiments, an amplified signal associated with a primary probe and the associated RCA product can be generated in the sample (e.g., using detection probes such as fluorescently labeled oligonucleotides).

In some embodiments, the methods involve imaging the biological sample to detect a particular nucleic acid or an amplification product thereof. In some embodiments, a sequence of the rolling circle amplification product, or other generated product can be analyzed in situ in the biological sample. In some of any embodiments, the imaging can comprise detecting a signal associated with a fluorescently labeled probe that directly or indirectly binds to a rolling circle amplification product of the circularized probe. In some embodiments, the sequence of the rolling circle amplification product, extension product, or other generated product can be analyzed by sequential hybridization, sequencing by hybridization, sequencing by ligation, sequencing by synthesis, sequencing by binding, or a combination thereof. In some embodiments, barcodes or complements thereof (e.g., barcode sequences or complements thereof comprised by the probes disclosed herein or products thereof) can be analyzed (e.g., detected or sequenced) using any suitable method or technique, including those described herein, such as sequencing by synthesis (SBS), sequencing by ligation (SBL), or sequencing by hybridization (SBH). In some instances, barcoding schemes and/or barcode detection schemes as described in RNA sequential probing of targets (RNA SPOTs), single-molecule fluorescent in situ hybridization (smFISH), multiplexed error-robust fluorescence in situ hybridization (MERFISH) or sequential fluorescence in situ hybridization (seqFISH+) can be used. In any of the preceding implementations, the methods provided herein can include analyzing the barcodes by sequential hybridization and detection with a plurality of labelled probes (e.g., detection probes (e.g., detection oligos) or barcode probes). In some instances, the barcode detection steps can be performed as described in hybridization-based in situ sequencing (HybISS). In some instances, probes can be detected and analyzed (e.g., detected or sequenced) as performed in fluorescent in situ sequencing (FISSEQ), or as performed in the detection steps of the spatially-resolved transcript amplicon readout mapping (STARmap) method. In some instances, signals associated with an analyte can be detected as performed in sequential fluorescent in situ hybridization (seqFISH).

In some aspects, an in situ hybridization based assay is used to localize and analyze nucleic acid sequences within a native biological sample, e.g., a portion or section of tissue. In some embodiments, the in situ assay is used to analyze the presence, absence, an amount or level of the probe (e.g., primary probe) hybridized to a nuclei acid substrate in a biological sample, while preserving spatial context.

In some embodiments, the methods involve in situ hybridization using directly or indirectly labeled molecules, e.g., complementary DNA or RNA or modified nucleic acids, as probes that bind or hybridize to an RNA substrate within a biological sample of interest. Nucleic acid probes or probe sets, in some examples, may be labelled with radioisotopes, epitopes, hapten, biotin, or fluorophores, to enable detection of the location of specific nucleic acid probes or probe sets in tissues.

In some embodiments, barcode sequences of the probes (or products thereof, such as amplification, extension, ligation, or hybridization products) are targeted by detectably labeled detection oligonucleotides, such as fluorescently labeled oligonucleotides. In some embodiments, one or more decoding schemes are used to decode the signals, such as fluorescence, for sequence determination. In some of any of the embodiments herein, barcodes (e.g., primary and/or secondary barcode sequences) can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," *Nature* 568(7751):235-239 (2019); Chen et al., "Spatially resolved, highly multiplexed RNA profiling in single cells," *Science;* 348(6233):aaa6090 (2015); Gyllborg et al., Nucleic Acids Res (2020) 48(19): e112; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some aspects, in situ assays use microscopy as a readout, e.g., nucleic acid sequencing, hybridization, or other detection or determination methods involving an optical readout. In some aspects, detection or determination of a sequence of one, two, three, four, five, or more nucleotides of a target nucleic acid is performed in situ in a cell in an intact tissue. In some aspects, the detection or determination is of a sequence associated with or indicative of a target nucleic acid. In some aspects, detection or determination of a sequence is performed such that the localization of the target nucleic acid (or product or a derivative thereof associated with the target nucleic acid) in the originating sample is detected. In some embodiments, the assay comprises detecting the presence or absence of an amplification product or a portion thereof (e.g., RCA product). In some embodiments, a provided method is quantitative and preserves the spatial information within a tissue sample without physically isolating cells or using homogenates.

In some aspects, the methods also involve imaging the amplification product (e.g., amplicon) and/or one or more portions of the polynucleotides, for example, via binding of a detectably labeled probe and detecting the detectable label. In some embodiments, the detectably labeled probe comprises a detectable label that can be measured and quantitated. A label or detectable label can be a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

A fluorophore can comprise a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. Autofluorescence can comprise background fluorescence (that can arise from a variety of sources, including aldehyde fixation, extracellular matrix components, red blood cells, lipofuscin, and the like), which is distinct from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

In some embodiments, a detectable probe containing a detectable label can be used to detect one or more probes and/or amplification products (e.g., amplicon) described herein. In some embodiments, the methods involve incubating the detectable probe containing the detectable label with the sample, washing unbound detectable probe, and detecting the label, e.g., by imaging.

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as 125I, 35S, 14C, or 3H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091, 519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264. A fluorescent label can comprise a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). Nucleotides having other fluorophores can also be synthesized (See, Henegariu et al. (2000) Nature Biotechnol. 18:345).

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. In some embodiments, an antibody comprises an antibody molecule of any class, or any sub-fragment thereof, such as a Fab.

Other suitable labels for a polynucleotide sequence comprises fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or an polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and 5,192,782. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting comprises determining a signal, e.g., a fluorescent signal. In some aspects, the detection (comprising imaging) is carried out using any one of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The fluorescence microscope can be any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequences can be analyzed in situ, e.g., by incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (e.g., nucleotide sequence) of the incorporated nucleotides or labeled primer extension products can be determined, and consequently, the nucleotide sequence of the corresponding template nucleic acid. Aspects of in situ analysis are described, for example, in Mitra et al., (2003) Anal. Biochem. 320, 55-65, and Lee et al., (2014) Science, 343(6177), 1360-1363; US 2016/0024555; US 2019/0194709; U.S. Pat. Nos. 10,138,509; 10,494,662; 10,179,932.

In some cases, sequencing can be performed after the analytes are released from the biological sample. In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232.

In some embodiments, the method involve detecting the one or more barcode sequences of the probe or a product thereof by contacting the biological sample that contains amplification products, with one or more detectably-labeled probes that directly or indirectly hybridize to the one or more barcode sequences, detecting signals associated with the one or more detectably-labeled probes, and dehybridizing the one or more detectably-labeled probes. In some embodiments, the contacting, detecting, and dehybridizing steps are repeated with the one or more detectably-labeled probes and/or one or more other detectably-labeled probes that directly or indirectly hybridize to the one or more barcode sequences. In some embodiments, the detectably labeled probes comprise a detectable label (e.g., are conjugated to a detectable label). In some embodiments, the detectably labeled probes are labeled with a sequence capable of hybridizing to a detection probe, wherein the detection probe comprises a detectable label (e.g., is conjugated to a detectable label). Methods of detecting and/or analyzing a sequence by sequential hybridization of probes have been described, for example, in U.S. Pat. Pub. 20210340618, the content of which is herein incorporated by reference in its entirety.

In some of any of the embodiments herein, the detecting of a particular nucleic acid or an amplification product thereof can comprise contacting the biological sample with one or more intermediate probes that directly or indirectly bind to the rolling circle amplification product, wherein the one or more intermediate probes are detectable using one or more detectably-labeled probes. In some of any of the embodiments herein, the detecting step can further comprise removing (e.g., dehybridizing) the one or more intermediate probes and/or the one or more detectably-labeled probes from the rolling circle amplification product. In some of any of the embodiments herein, the contacting and removing (e.g., dehybridizing) steps can be repeated with the one or more intermediate probes, the one or more detectably-labeled probes, one or more other intermediate probes, and/or one or more other detectably-labeled probes.

In some embodiments, the one or more intermediate probes comprise one or more overhang regions (e.g., a 5' and/or 3' end of the probe that does not hybridize to the rolling circle amplification product). A probe comprising a single overhang region may be referred to as an "L-shaped probe," and a probe comprising two overhangs may be referred to as a "U-shaped probe." In some cases, the overhang region comprises a binding region for binding one or more detectably-labeled probes. In some embodiments, the detecting comprises contacting the biological sample with a pool of intermediate probes corresponding to different barcode sequences or portions thereof, and a pool of detectably-labeled probes corresponding to different detectable labels. In some embodiments, the biological sample is sequentially contacted with different pools of intermediate probes. In some instances, a common or universal pool of detectably-labeled probes is used in a plurality of sequential hybridization steps (e.g., with different pools of intermediate probes).

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597.

In some embodiments, nucleic acid hybridization can be used for sequence detection. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

V. KITS

Also provided herein are kits, for example comprising a recombinant and/or modified AP50 polymerase and one or more additional components, and reagents for performing the methods provided herein, for example reagents required for one or more steps for amplification, detection, sequencing, and/or sample preparation as described herein. In some embodiments, the kit comprises isolated and purified recombinant and/or modified AP50 polymerases as described in Section II. In some embodiments, the kit comprises a recombinant and/or modified AP50 polymerase, for example, any described herein in Section II, and/or a polynucleotide, recombinant nucleic acid molecule, or vector, for example, as described in Section III. In some embodiments, the recombinant nucleic acid comprises deoxyribonucleotide. In some embodiments, the recombinant nucleic acid comprises one or more ribonucleotide residues. In some embodiments, the kit further comprises a detection probe (e.g., a plurality of detectably labelled probes) for detection of a nucleic acid as described in Section IV, e.g., DNA or RNA.

In some embodiments, the kit further comprises one or more components, such as a dNTP, a di-cation, and a reaction buffer. In some embodiments, the kit further comprises one or more primer. In some embodiments, the one or more primer included in the kit may include one or more circular or circularizable probes (e.g., padlock probes). In some embodiments, the circularizable probe is a circularizable probe set. In some embodiments, the kit further comprises instructions for use, for example, instructions for amplifying a nucleic acid, e.g., DNA. In some embodiments, the kit further comprises a probe for detection of the amplified nucleic acid, e.g., DNA. In some embodiments, the probe is a circular or circularizable probe or probe set (e.g., padlock probe) for detection of the amplified nucleic acid, e.g., DNA. In some embodiments, the kit is for nucleic acid amplification. In some embodiments, the nucleic acid is amplified by rolling circle amplification (RCA) using the recombinant and/or modified AP50 polymerase. In some embodiments, the nucleic acid is amplified in situ in the biological sample using the recombinant polymerase.

In some aspects, a kit comprising the provided polynucleotide, for example, those described in Section III.A, the provided recombinant nucleic acid molecule or vector, for example, those described in Section III.B, and a provided recombinant expression system, for example, those described in Section III.C. In some embodiments, the kit further comprises instructions for use. In some embodiments, the recombinant expression system is a cell system or a cell-free system. In some embodiments, the recombinant expression system comprises one or more cell systems selected from among a bacterial cell, a fungal cell, an insect cell, and a mammalian cell. In some embodiments, the kit is for improving the processivity, sensitivity, specificity, solubility, polymerization rate, thermostability, and uniformity of a recombinant polymerase activity compared to a reference polymerase. In some embodiments, the reference polymerase is a wild-type AP50 polymerase set forth in SEQ ID NO:1. In some embodiments, the reference polymerase is a wild-type Phi29 polymerase set forth in SEQ ID NO:5.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, recombinant and/or modified nucleotides, reagents for additional assays.

In some aspects, the provided embodiments can be applied in an in situ method of analyzing nucleic acid sequences, such as an in situ transcriptomic analysis or in situ sequencing, for example from intact tissues or samples in which the spatial information has been preserved. In some aspects, the embodiments can be applied in an imaging or detection method for multiplexed nucleic acid analysis. In some aspects, the provided embodiments can be used to identify or detect regions of interest in target nucleic acids.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

VI. TERMINOLOGY

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined In some ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

"Amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

In some aspects, conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa.

Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g., U.S. Pat. No. 8,562,989; pages 13-15 "Biochemistry" $2^{nd}$ ED. Lubert Stryer ed (Stanford University); Henikoff et al., PNAS 1992 Vol 89 10915-10919; Lei et al., J Biol Chem 1995 May 19; 270(20):11882-6).

An amino acid substitution may include replacement of one amino acid in a polypeptide with another amino acid. Amino acid substitutions may be introduced to generate a modified AP50 polymerase as described herein.

Amino acids generally can be grouped according to the following common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

In some contexts, conservative substitutions can involve the exchange of a member of one of these classes for another member of the same class. In some contexts, non-conservative amino acid substitutions can involve exchanging a member of one of these classes for another class. In some contexts, particular substitutions can be considered "conservative" or "non-conservative" depending on the stringency and context and environment of the particular residue in primary, secondary and/or tertiary structure of the protein.

The term "peptide" as used herein refers to a plurality of amino acids joined together, such as in a linear or circular chain. The term oligopeptide is typically used to describe peptides having between 2 and about 50 or more amino acids. Peptides larger than about 50 are often referred to as polypeptides or proteins.

The terms "polypeptide" and "protein" are used interchangeably to refer to a polymer of amino acid residues, and are not limited to a minimum length. Polypeptides, including the provided antibodies and antibody chains and other peptides, e.g., linkers, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An "isolated" protein, polypeptide or nucleic acid refers to a protein, polypeptide or nucleic acid molecule that has been separated from a component of its natural environment. An isolated protein or polypeptide can refer to a purified protein or polypeptide. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In some aspects, a "recombinant expression system" comprises a host cell.

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from among adenine (A), thymine (T), cytosine (C), or guanine (G), and a ribonucleic acid can have one or more bases selected from among uracil (U), adenine (A), cytosine (C), or guanine (G). Useful non-native bases that can be included in a nucleic acid or nucleotide are known in the art.

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

The term "polymerase" includes not only naturally-occurring enzymes but also all modified derivatives thereof, including also derivatives of naturally-occurring polymerase enzymes. For instance, in some embodiments, the polymerase can have been modified to remove 5'-3' exonuclease activity. Sequence-modified derivatives or mutants of polymerase enzymes that can be used include, but are not limited to, mutants that retain at least some of the functional, e.g. polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some aspects, the AP50 polymerase is referred to as a modified AP50 polymerase. The term "modified AP50 polymerase" includes any AP50 polymerase variant that is distinguishable from the wild-type AP50 polymerase set forth in sequence SEQ ID NO:1. For example, any amino acid deletion, insertion, and/or substitution that alters the amino acid sequence of the AP50 polymerase is included. The modified AP50 polymerase may also be referred to as a variant AP50 polymerase, a mutant AP50 polymerase, and/or a derivative AP50 polymerase.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments, the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

The terms "detectable label," "optical label," and "label" are used interchangeably herein to refer to a directly or indirectly detectable moiety that is associated with (e.g., conjugated to) a molecule to be detected, e.g., a probe for in situ assay or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a probe associated with a feature. For example, detectably labeled features can include a fluorescent, a colorimetric, or a chemiluminescent label attached to a bead (see, for example, Raj eswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, a probe, or composition to be detected. For example, detectable labels can be incorporated during nucleic acid polymerization or amplification (e.g., Cy5®-labeled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine 0-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DiIC18 (5)), DIDS, Di1 (DiIC18(3)), DiO (DiOC18(3)), DiR (DiIC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorophyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and—methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

VII. EXAMPLES

The following examples are included for illustrative purposes only and are not intended to limit the scope of the present disclosure.

Example 1: In Vitro Rolling Circle Amplification (RCA) Assay Comparing *Bacillus* Phage AP50 Polymerase to Phi29 Polymerase This example describes the generation and use of an exemplary *Bacillus* phage AP50 polymerase (APol) in rolling circle amplification (RCA), demonstrating improved in vitro activities compared to a wild-type Phi29 polymerase.

An exemplary modified AP50 polymerase, a truncated *Bacillus* phage AP50 polymerase (APolTr; set forth in SEQ ID NO:6, containing a truncation of 94 contiguous amino acids from the C-terminus, with reference to SEQ ID NO:1) fused to a linker and a poly Histidine tag, was recombinantly produced, and tested in an in vitro RCA assay.

Briefly, 50 nM of a circularizable probe was mixed with 100 nM of an RNA template, and 50 nM of an RCA primer and incubated at 37° C. for 1 hour for probe hybridization to the template. 1 μM of a ligase was then added and incubated at 37° C. for 1 hour for ligation of the circularizable probe. The ligated product, an RCA polymerase (truncated AP50 polymerase (APolTr) at various concentrations (30, 100, 300, and 1000 nM) or wild-type Phi29 polymerase (150 nM)) and dNTPs were incubated at different temperatures to generate RCA products (RCPs) at 30° C., and SYBR Gold labeling of the RCPs was monitored in real-time based on fluorescence changes (at excitation wavelength of 495 nm and emission wavelength of 537 nm) using a plate reader.

As shown in FIG. 1, results from the in vitro RCA assay at 30° C. showed that the exemplary AP50 polymerase (APolTr) generated more RCPs, as indicated by the elevated fluorescence intensity of SYBR Gold labelled RCPs, compared to wild-type Phi29. The exemplary AP50 polymerase generated more RCPs even at lower polymerase concentrations (e.g., 30 nM) than wild-type Phi29. The results indicate the exemplary AP50 polymerase exhibited improved properties, including improved polymerization rate and increased RCP generation at 30° C. compared to a wild-type Phi29 polymerase, which may be associated with improved thermostability, processivity, and/or polymerization rate of the AP50 polymerase. The results support the utility and benefit of exemplary AP50 polymerases in methods of nucleic acid amplification, such as RCA.

Example 2: In Vitro Rolling Circle Amplification (RCA) Assay Using *Bacillus* Phage AP50 Polymerase at Different Temperatures and Concentrations This example describes the generation and use of an exemplary *Bacillus* phage AP50 polymerase in rolling circle amplification (RCA) at different temperatures and concentrations, demonstrating robust in vitro RCA activities.

An exemplary modified AP50 polymerase, the truncated APol (APolTr) as described in Example 1, was recombinantly produced, and tested in an in vitro RCA assay, generally as described in Example 1 above, at 30° C., 37° C., 42° C., or 50° C., and at concentrations of the APolTr polymerase at 3, 10, 30, 100, 300, 1000, 3000, and 10000 nM.

As shown in FIGS. 2A-2D, results from the in vitro RCA assay at 30° C. (FIG. 2A), 37° C. (FIG. 2B), 42° C. (FIG. 2C), and 50° C. (FIG. 2D) showed that the exemplary modified AP50 polymerase had robust RCA activity and generated substantial RCPs at all temperatures, including at 50° C. (FIG. 2D), as indicated by the fluorescence intensity of SYBR Gold labelled RCPs. An improved kinetics of polymerization at 50° C. was also observed, compared to the kinetics at lower temperatures. AP50 polymerase demonstrated improved RCA activity at 42° C. (FIG. 2C) compared to the activity at 37° C. (FIG. 2B), suggesting improved thermostability. In contrast, other RCA polymerases such as wild-type Phi29 polymerases show reduced activity and thermostability at certain elevated temperatures such as 42° C. The results indicate the exemplary AP50 polymerase exhibited improved properties, including improved polymerization rate and increased RCP generation at an elevated temperature (e.g., 42° C. and 50° C.) which may be associated with improved thermostability, processivity, and/or polymerization rate of the exemplary AP50 polymerase. The results support the utility and benefit of exemplary AP50 polymerase in methods of nucleic acid amplification, such as RCA.

Example 3: Assessing Sensitivity of *Bacillus* Phage AP50 Polymerase and Phi29 Polymerase in an In Situ Rolling Circle Amplification (RCA)

This example describes the generation and use of an exemplary *Bacillus* phage AP50 polymerase in rolling circle amplification (RCA), demonstrating comparable in vitro RCA sensitivity compared to a wild-type Phi29 polymerase.

An exemplary modified AP50 polymerase, the truncated APol (APolTr) as described in Example 1, was recombinantly produced, and tested in an in situ RCA assay. Briefly, a tissue sample was prepared for in situ RCA for gene expression analysis using the APolTr or wild-type Phi29 polymerase. Circularizable probes were added to each tissue sample and allowed to hybridize. Following probe hybridization, the tissue samples were washed to remove unbound probes. Circularizable probe ligation was performed by adding a ligase and a ligase buffer to the samples. For RCA, samples were incubated at 30° C. or 42° C. in a reaction mix containing a polymerase buffer, dNTPs, and either the APolTr at various concentrations (250, 500, and 1000 nM) or 5U of wild-type Phi29 polymerase. RCPs were detected by hybridizing labeled probes to the RCPs in situ and imaging the samples with a fluorescent microscope. The median transcripts per cell were assessed.

Figure 3:
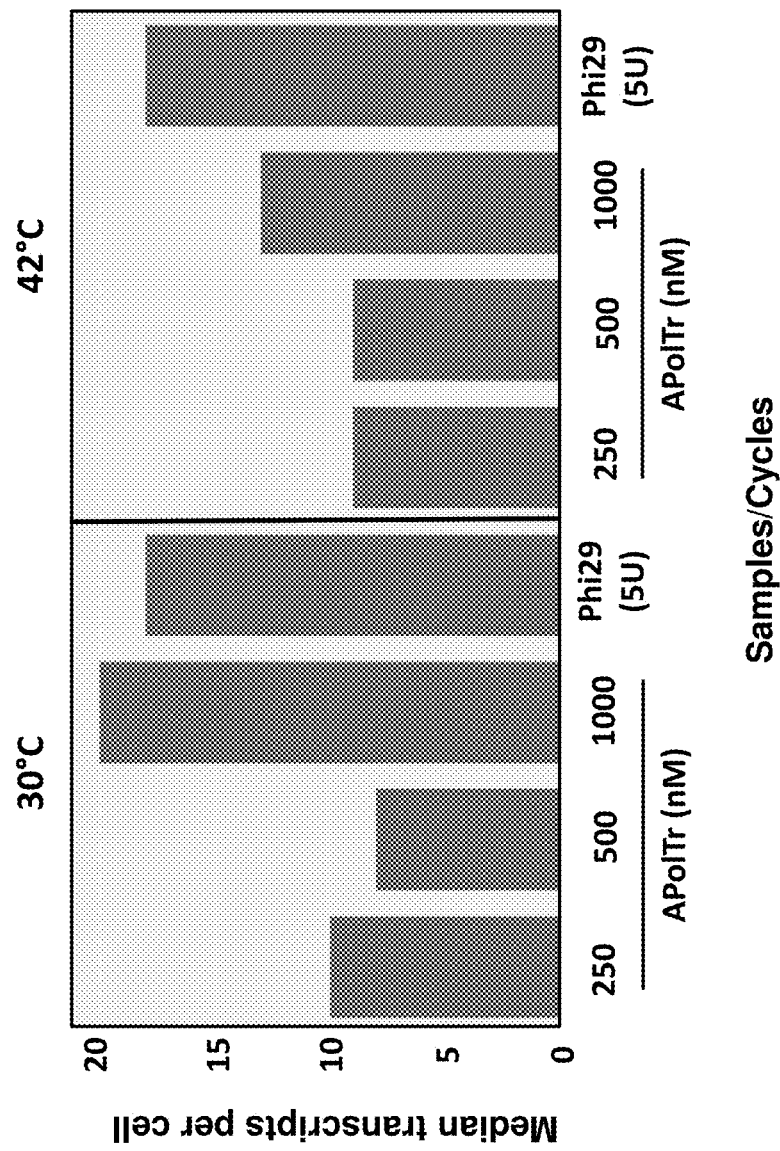
FIG. 3 depicts results from an in vitro rolling circle amplification (RCA) assay using a Cassini workflow comparing activities of a wild-type Phi29 polymerase and an exemplary modified *Bacillus* phage AP50 polymerase (APolTr).

As shown in FIG. 3, results from the in situ RCA assay at 30° C. and 42° C. showed that the exemplary AP50 polymerase generated a comparable medium number of transcripts per cell more compared to wild-type Phi29 polymerase at 5U. At 1000 nM concentration, the exemplary AP50 polymerase generated more transcripts per cell at 30° C. than wild-type Phi29 polymerase.

The results indicate the exemplary AP50 polymerase exhibited comparable sensitivity for amplification in an in situ RCA compared to a high concentration of wild-type Phi29 polymerase, supporting the utility and benefit of exemplary AP50 polymerases in methods of in situ analysis involving nucleic acid amplification, such as in situ RCA.

The present disclosure is not intended to be limited in scope to the particular disclosed embodiments, which are provided, for example, to illustrate various aspects of the present disclosure. Various modifications to the compositions and methods described will become apparent from the description and teachings herein. Such variations may be practiced without departing from the true scope and spirit of the disclosure and are intended to fall within the scope of the present disclosure.

| SEQ ID NO | SEQUENCE | DESCRIPTION |
|---|---|---|
| 1 | GSNKQKKERQKPAKLLTLDTETRGLTGNVFRVGLFDGTNYYKSNTFDEILDLFEQYKDYECHVY VHNLDFDLAKIATTLFKRDRVRFAKSIFINGNVVTLHSDSMILHDSLRLLPGSLEKLCKDFGLT DNAKKDLSEVIKEQGYAVYKKDGVTFDKKKSLGNYFENVPADDPTLNEYLEFDCRSLYEILTIV MDIANIGLETLVMCPTTASLAMRVYKEQYREQYDKVATHFYMGEWGQFLEEHVRQSYYGGRTEV FTPHLPHGYHYDVNSLYPYVMKIAKFPVGYPNLLKDGQAATKWKHWKRRAIGGGVMWCRVDVPE DMYIPVLPKRDPSGKLLFPVGKLEGVWTLPELLEAEKNGCTIEAIYQMVYWEHMEPIFKEFVEH FEDLKKNSKGAKRTFAKLIQNSLYGKFGMNRVRVSLGDMEDRYDLHEKQIPYKEFKHDCNGLTL EFIQYISESKASYIQPHIATYVTAYARILLFRGLKEQASKGVLGYCDTDSIAGTAKMPDEMIHD EDYGKWALEGELEEGIFLQPKFYAERYTNGKEVIKAKGIPREKMEELSFENYKEWLEIMKEGQQ ERIDIFEGYESRKKFSTTLKASEDFDTLREMKKSINLLLEQKRDIDYKGNVTRPHKRYDYGDKK DKIDYEDYKSREDKLNNMYDDVDDLKEQVDEIGYIKCMKQGDMYFEEYKHLTKSVKSKYFRRTG TPIDVWANESGWDVNELLEELRLMGVC | APol (aa) without initial Met |
| 2 | GSNKQKKERQKPAKLLTLDTETRGLTGNVFRVGLFDGTNYYKSNTFDEILDLFEQYKDYECHVY VHNLDFDLAKIATTLFKRDRVRFAKSIFINGNVVTLHSDSMILHDSLRLLPGSLEKLCKDFGLT DNAKKDLSEVIKEQGYAVYKKDGVTFDKKKSLGNYFENVPADDPTLNEYLEFDCRSLYEILTIV MDIANIGLETLVMCPTTASLAMRVYKEQYREQYDKVATHFYMGEWGQFLEEHVRQSYYGGRTEV FTPHLPHGYHYDVNSLYPYVMKIAKFPVGYPNLLKDGQAATKWKHWKRRAIGGGVMWCRVDVPE DMYIPVLPKRDPSGKLLFPVGKLEGVWTLPELLEAEKNGCTIEAIYQMVYWEHMEPIFKEFVEH FEDLKKNSKGAKRTFAKLIQNSLYGKFGMNRVRVSLGDMEDRYDLHEKQIPYKEFKHDCNGLTL EFIQYISESKASYIQPHIATYVTAYARILLFRGLKEQASKGVLGYCDTDSIAGTAKMPDEMIHD EDYGKWALEGELEEGIFLQPKFYAERYTNGKEVIKAKGIPREKMEELSFENYKEWLEIMKEGQQ ERIDIFEGYESRKKESTTLKASEDEDTLREMKKSINLLLEQKRDIDYKGNVTRPHKRYDYGDKK DKIDYEDYKSREDKLNNMYDDVDDLKEQVDEIGYIKCMKQGDMYFEEYKHLTKSVKSKYFRRTG TPIDVWANESGWDVNELLEELRLMGVCGGSHHHHHH | APol-His (aa) without initial Met |
| 3 | GSNKQKKERQKPAKLLTLDTETRGLTGNVFRVGLFDGTNYYKSNTFDEILDLFEQYKDYECHVY VHNLDFDLAKIATTLFKRDRVRFAKSIFINGNVVTLHSDSMILHDSLRLLPGSLEKLCKDFGLT DNAKKDLSEVIKEQGYAVYKKDGVTFDKKKSLGNYFENVPADDPTLNEYLEFDCRSLYEILTIV MDIANIGLETLVMCPTTASLAMRVYKEQYREQYDKVATHFYMGEWGQFLEEHVRQSYYGGRTEV FTPHLPHGYHYDVNSLYPYVMKIAKFPVGYPNLLKDGQAATKWKHWKRRAIGGGVMWCRVDVPE DMYIPVLPKRDPSGKLLFPVGKLEGVWTLPELLEAEKNGCTIEAIYQMVYWEHMEPIFKEFVEH FEDLKKNSKGAKRTFAKLIQNSLYGKFGMNRVRVSLGDMEDRYDLHEKQIPYKEFKHDCNGLTL EFIQYISESKASYIQPHIATYVTAYARILLFRGLKEQASKGVLGYCDTDSIAGTAKMPDEMIHD EDYGKWALEGELEEGIFLQPKFYAERYTNGKEVIKAKGIPREKMEELSFENYKEWLEIMKEGQQ ERIDIFEGYESRKKESTTLKASEDFDTLREMKKSINLLLEQKRDIDYKGNVTRPHKRYDYGGGS HHHHHH | APolTr-His (aa) without initial Met |
| 4 | GSNKQKKERQKPAKLLTLDTETRGLTGNVFRVGLFDGTNYYKSNTFDEILDLFEQYKDYECHVY VHNLDFDLAKIATTLFKRDRVRFAKSIFINGNVVTLHSDSMILHDSLRLLPGSLEKLCKDFGLT DNAKKDLSEVIKEQGYAVYKKDGVTFDKKKSLGNYFENVPADDPTLNEYLEFDCRSLYEILTIV MDIANIGLETLVMCPTTASLAMRVYKEQYREQYDKVATHFYMGEWGQFLEEHVRQSYYGGRTEV FTPHLPHGYHYDVNSLYPYVMKIAKFPVGYPNLLKDGQAATKWKHWKRRAIGGGVMWCRVDVPE DMYIPVLPKRDPSGKLLFPVGKLEGVWTLPELLEAEKNGCTIEAIYQMVYWEHMEPIFKEFVEH FEDLKKNSKGAKRTFAKLIQNSLYGKFGMNRVRVSLGDMEDRYDLHEKQIPYKEFKHDCNGLTL EFIQYISESKASYIQPHIATYVTAYARILLFRGLKEQASKGVLGYCDTDSIAGTAKMPDEMIHD EDYGKWALEGELEEGIFLQPKFYAERYTNGKEVIKAKGIPREKMEELSFENYKEWLEIMKEGQQ ERIDIFEGYESRKKFSTTLKASEDFDTLREMKKSINLLLEQKRDIDYKGNVTRPHKRYDYGGGS HHHHHHSEEDEEKEEDG | APolTr-His-SET (aa) without initial Met |
| 5 | KHMPRKMYSCDFETTTKVEDCRVWAYGYMNIEDHSEYKIGNSLDEFMAWVLKVQADLYFHNLKF DGAFIINWLERNGFKWSADGLPNTYNTIISRMGQWYMIDICLGYKGKRKIHTVIYDSLKKLPFP VKKIAKDFKLTVLKGDIDYHKERPVGYKITPEEYAYIKNDIQIIAEALLIQFKOGLDRMTAGSD SLKGFKDIITTKKFKKVFPTLSLGLDKEVRYAYRGGFTWLNDRFKEKEIGEGMVFDVNSLYPAQ MYSRLLPYGEPIVFEGKYVWDEDYPLHIQHIRCEFELKEGYIPTIQIKRSRFYKGNEYLKSSGG EIADLWLSNVDLELMKEHYDLYNVEYISGLKFKATTGLFKDFIDKWTYIKTTSEGAIKQLAKLM LNSLYGKFASNPDVTGKVPYLKENGALGFRLGEEETKDPVYTPMGVFITAWARYTTITAAQACY DRIIYCDTDSIHLTGTEIPDVIKDIVDPKKLGYWAHESTFKRAKYLRQKTYIQDIYMKEVDGKL VEGSPDDYTDIKFSVKCAGMTDKIKKEVTFENFKVGFSRKMKPKPVQVPGGVVLVDDTFTIK | Phi29 WT (aa) without initial Met |
| 6 | GSNKQKKERQKPAKLLTLDTETRGLTGNVFRVGLFDGTNYYKSNTFDEILDLFEQYKDYECHVY VHNLDFDLAKIATTLFKRDRVRFAKSIFINGNVVTLHSDSMILHDSLRLLPGSLEKLCKDFGLT DNAKKDLSEVIKEQGYAVYKKDGVTFDKKKSLGNYFENVPADDPTLNEYLEFDCRSLYEILTIV MDIANIGLETLVMCPTTASLAMRVYKEQYREQYDKVATHFYMGEWGQFLEEHVRQSYYGGRTEV FTPHLPHGYHYDVNSLYPYVMKIAKFPVGYPNLLKDGQAATKWKHWKRRAIGGGVMWCRVDVPE DMYIPVLPKRDPSGKLLFPVGKLEGVWTLPELLEAEKNGCTIEAIYQMVYWEHMEPIFKEFVEH FEDLKKNSKGAKRTFAKLIQNSLYGKFGMNRVRVSLGDMEDRYDLHEKQIPYKEFKHDCNGLTL EFIQYISESKASYIQPHIATYVTAYARILLFRGLKEQASKGVLGYCDTDSIAGTAKMPDEMIHD EDYGKWALEGELEEGIFLQPKFYAERYTNGKEVIKAKGIPREKMEELSFENYKEWLEIMKEGQQ ERIDIFEGYESRKKFSTTLKASEDFDTLREMKKSINLLLEQKRDIDYKGNVTRPHKRYDYG | APolTr (aa) without initial Met |
| 7 | HHHHHH | 6x His tag (aa) |

-continued

| SEQ ID NO | SEQUENCE | DESCRIPTION |
|---|---|---|
| 8 | SEEDEEKEEDG | Solubility enhancement tag (SET) (aa) |
| 9 | GGSHHHHHHSEEDEEKEEDG | GSSlinker-6x His-SET (aa) |
| 10 | GGS | GGSlinker (aa) |
| 11 | GGSGG | GGSGG linker (aa) |
| 12 | GGGGG | GGGGG linker (aa) |
| 13 | GGAGG | GGAGG linker (aa) |
| 14 | GGGGSSS | GGGGSSS linker (aa) |
| 15 | GGGGAAA | GGGGAAA linker (aa) |
| 16 | GGGGS | (GGGGS)n linker (aa), n is 1 to 10 |
| 17 | GGCTCCAATAAGCAAAAGAAAGAGCGCCAAAAGCCGGCCAAGCTTCTCACCTTGGACACTGAGA CGCGCGGCCTCACCGGTAATGTGTTCCGCGTTGGCCTGTTTGACGGGACGAATTATTACAAGTC GAATACATTCGACGAGATCCTTGACCTGTTCGAGCAATATAAAGATTACGAATGTCATGTATAC GTACACAATTTAGACTTCGACTTGGCGAAAATCGCCACCACTTTGTTCAAGCGCGACCGTGTGC GCTTTGCGAAGAGCATCTTCATTAACGGTAACGTAGTGACTTTGCATTCGGACTCGATGATCTT ACATGATAGCTTACGCTTACTGCCGGGGTCTCTGGAAAAGCTCTGTAAAGATTTTGGCCTGACC GACAACGCCAAGAAAGATCTTTCCGAAGTCATCAAAGAGCAGGGTTACGCAGTATACAAGAAAG ACGGTGTCACATTTGACAAGAAGAAATCCCTTGGCAATTATTTTGAGAACGTGCCTGCCGACGA CCCTACGCTCAATGAGTACTTGGAGTTCGATTGTCGCAGCCTGTACGAGATTTTGACGATTGTG ATGGACATCGCAAATATTGGCCTGGAAACCTTAGTAATGTGCCCGACCACAGCGAGCTTAGCCA TGCGTGTCTATAAAGAGCAATACCGCGAGCAATATGATAAGGTGGCCACTCACTTTTATATGGG CGAGTGGGGTCAATTCCTCGAAGAGCACGTTCGCCAATCGTACTACGGTGGTCGCACTGAGGTA TTTACCCCTCATTTACCACATGGTTACCATTACGATGTTAACTCGTTGTACCCGTATGTCATGA AAATTGCAAAGTTCCCGGTAGGGTACCCAAATTTATTGAAAGACGGCCAGGCAGCTACCAAGTG GAAGCATTGGAAGCGTCGTGCGATCGGGGGCGGTGTTATGTGGTGTCGTGTGGACGTTCCTGAA GACATGTACATCCCAGTGCTCCGAAGCGTGACCCGAGCGGGAAGTTATTGTTCCCGGTTGGTA AGCTCGAGGGAGTGTGGACCCTGCCTGAGCTCCTGGAAGCGGAAAAGAATGGCTGTACGATCGA GGCGATTTACCAGATGGTATACTGGGAGCATATGGAGCGATCTTTAAAGAATTCGTTGAGCAC TTTGAAGACCTCAAGAAGAACAGTAAGGGAGCGAAGCGCACCTTTGCAAAGCTTATCCAGAATA GCTTGTACGGGAAGTTCGGCATGAACCGCGTTCGTGTGTCGTTGGGTGACATGGAAGACCGTTA CGACTTGCATGAGAAGCAGATTCCATATAAAGAATTCAAACATGATTGTAATGGCTTGACGCTT GAGTTCATCCAATATATCTCGGAAAGCAAAGCGAGCTATATTCAACCGCACATTGCTACATACG TAACAGCCTATGCTCGTATCCTGTTGTTTCGTGGTCTGAAAGAACAGGCTAGCAAGGGCGTACT GGGCTATTGCGATACTGACTCTATTGCCGGTACCGCCAAAATGCCGGACGAAATGATCCATGAC GAAGATTACGGCAAGTGGGCCTTGGAAGGTGAGCTGGAAGAAGGTATCTTTCTCCAGCCGAAGT TTTACGCGGAACGTTACACGAACGGCAAAGAAGTAATTAAGGCCAAGGGGATTCCACGCGAGAA GATGAAGAGTTAAGTTTCGAGAACTATAAAGAGTGGCTCGAGATTATGAAAGAAGGCCAACAA GAGCGCATCGACATCTTTGAAGGTTACGAGAGTCGCAAGAAGTTTAGCACCACACTCAAGGCCA GTGAAGATTTCGACACGTTGCGTGAGATGAAGAAGTCTATCAATTTACTGCTCGAGCAGAAGCG CGACATCGACTACAAGGGCAACGTGACACGTCCACATAAGCGCTATGACTACGGTGATAAGAAA GACAAGATCGATTATGAAGACTATAAGAGCCGTGAAGACAAGTTAAACAACATGTACGACGATG TAGACGACTTAAAAGAGCAAGTTGACGAGATCGGCTACATCAAGTGCATGAAGCAAGGCGATAT GTATTTTGAAGAGTACAAACATCTTACGAAGTCTGTGAAAAGTAAGTATTTCCGCCGCACTGGC ACCCCAATCGACGTATGGGCGAACGAATCCGGTTGGGACGTAAACGAGTTATTAGAAGAGCTTC GTCTGATGGGCGTGTGC | APol (nt) |
| 18 | GGCTCCAATAAGCAAAAGAAAGAGCGCCAAAAGCCGGCCAAGCTTCTCACCTTGGACACTGAGA CGCGCGGCCTCACCGGTAATGTGTTCCGCGTTGGCCTGTTTGACGGGACGAATTATTACAAGTC GAATACATTCGACGAGATCCTTGACCTGTTCGAGCAATATAAAGATTACGAATGTCATGTATAC GTACACAATTTAGACTTCGACTTGGCGAAAATCGCCACCACTTTGTTCAAGCGCGACCGTGTGC GCTTTGCGAAGAGCATCTTCATTAACGGTAACGTAGTGACTTTGCATTCGGACTCGATGATCTT ACATGATAGCTTACGCTTACTGCCGGGGTCTCTGGAAAAGCTCTGTAAAGATTTTGGCCTGACC | APol-His (nt) |

| SEQ ID NO | SEQUENCE | DESCRIPTION |
|---|---|---|
| | GACAACGCCAAGAAAGATCTTTCCGAAGTCATCAAAGAGCAGGGTTACGCAGTATACAAGAAAG<br>ACGGTGTCACATTTGACAAGAAGAAATCCCTTGGCAATTATTTTGAGAACGTGCCTGCCGACGA<br>CCCTACGCTCAATGAGTACTTGGAGTTCGATTGTCGCAGCCTGTACGAGATTTTGACGATTGTG<br>ATGGACATCGCAAATATTGGCCTGGAAACCTTAGTAATGTGCCCGACCACAGCGAGCTTAGCCA<br>TGCGTGTCTATAAAGAGCAATACCGCGAGCAATATGATAAGGTGGCCACTCACTTTTATATGGG<br>CGAGTGGGTCAATTCCTCGAAGAGCACGTTCGCCAATCGTACTACGGTGGTCGCACTGAGGTA<br>TTTACCCCTCATTTACCACATGGTTACCATTACGATGTTAACTCGTTGTACCCGTATGTCATGA<br>AAATTGCAAGTTCCCGGTAGGGTACCCAAATTTATTGAAAGACGGCCAGGCAGCTACCAAGTG<br>GAAGCATTGGAAGCGTCGTGCGATCGGGGCGGTGTTATGTGGTGTCGTGTGGACGTTCCTGAA<br>GACATGTACATCCCAGTGCTCCCGAAGCGTGACCCGAGCGGGAAGTTATTGTTCCCGGTTGGTA<br>AGCTCGAGGGAGTGTGGACCCTGCCTGAGCTCCTGGAAGCGGAAAAGAATGGCTGTACGATCGA<br>GGCGATTTACCAGATGGTATACTGGGAGCATATGGAGCCGATCTTTAAAGAATTCGTTGAGCAC<br>TTTGAAGACCTCAAGAAGAACAGTAAGGGAGCGAAGCGCACCTTTGCAAAGCTTATCCAGAATA<br>GCTTGTACGGGAAGTTCGGCATGAACCGCGTTCGTGTGTCGTTGGGTGACATGGAAGACCGTTA<br>CGACTTGCATGAGAAGCAGATTCCATATAAAGAATTCAAACATGATTGTAATGGCTTGACGCTT<br>GAGTTCATCCAATATATCTCGGAAAGCAAAGCGAGCTATATTCAACCGCACATTGCTACATACG<br>TAACAGCCTATGCTCGTATCCTGTTGTTTCGTGGTCTGAAAGAACAGGCTAGCAAGGGCGTACT<br>GGGCTATTGCGATACTGACTCTATTGCCGGTACCGCCAAAATGCCGGACGAAATGATCCATGAC<br>GAAGATTACGGCAAGTGGGCCTTGGAAGGTGAGCTGGAAGAAGGTATCTTTCTCCAGCCGAAGT<br>TTTACGCGGAACGTTACACGAACGGCAAAGAAGTAATTAAGGCCAAGGGGATTCCACGCGAGAA<br>GATGGAAGAGTTAAGTTTCGAGAACTATAAAGAGTGGCTCGAGATTATGAAAGAAGGCCAACAA<br>GAGCGCATCGACATCTTTGAAGGTTACGAGAGTCGCAAGAAGTTTAGCACCACACTCAAGGCCA<br>GTGAAGATTTCGACACGTTGCGTGAGATGAAGAAGTCTATCAATTTACTGCTCGAGCAGAAGCG<br>CGACATCGACTACAAGGGCAACGTGACACGTCCACATAAGCGCTATGACTACGGTGATAAGAAA<br>GACAAGATCGATTATGAAGACTATAAGAGCCGTGAAGACAAGTTAAACAACATGTACGACGATG<br>TAGACGACTTAAAAGAGCAAGTTGACGAGATCGGCTACATCAAGTGCATGAAGCAAGGCGATAT<br>GTATTTTGAAGAGTACAAACATCTTACGAAGTCTGTGAAAAGTAAGTATTTCCGCCGCACTGGC<br>ACCCCAATCGACGTATGGGCGAACGAATCCGGTTGGGACGTAAACGAGTTATTAGAAGAGCTTC<br>GTCTGATGGGCGTGTGCGGTGGCTCACATCACCACCATCATCAT | |
| 19 | GGCTCCAATAAGCAAAAGAAAGAGCGCCAAAAGCCGGCCAAGCTTCTCACCTTGGACACTGAGA<br>CGCGCGGCCTCACCGGTAATGTGTTCCGCGTTGGCCTGTTTGACGGGACGAATTATTACAAGTC<br>GAATACATTCGACGAGATCCTTGACCTGTTCGAGCAATATAAAGATTACGAATGTCATGTATAC<br>GTACACAATTTAGACTTCGACTTGGCGAAAATCGCCACCACTTTGTTCAAGCGCGACCGTGTGC<br>GCTTTGCGAAGAGCATCTTCATTAACGGTAACGTAGTGACTTTGCATTCGGACTCGATGATCTT<br>ACATGATAGCTTACGCTTACTGCCGGGGTCTCTGGAAAAGCTCTGTAAAGATTTTGGCCTGACC<br>GACAACGCCAAGAAAGATCTTTCCGAAGTCATCAAAGAGCAGGGTTACGCAGTATACAAGAAAG<br>ACGGTGTCACATTTGACAAGAAGAAATCCCTTGGCAATTATTTTGAGAACGTGCCTGCCGACGA<br>CCCTACGCTCAATGAGTACTTGGAGTTCGATTGTCGCAGCCTGTACGAGATTTTGACGATTGTG<br>ATGGACATCGCAAATATTGGCCTGGAAACCTTAGTAATGTGCCCGACCACAGCGAGCTTAGCCA<br>TGCGTGTCTATAAAGAGCAATACCGCGAGCAATATGATAAGGTGGCCACTCACTTTTATATGGG<br>CGAGTGGGTCAATTCCTCGAAGAGCACGTTCGCCAATCGTACTACGGTGGTCGCACTGAGGTA<br>TTTACCCCTCATTTACCACATGGTTACCATTACGATGTTAACTCGTTGTACCCGTATGTCATGA<br>AAATTGCAAGTTCCCGGTAGGGTACCCAAATTTATTGAAAGACGGCCAGGCAGCTACCAAGTG<br>GAAGCATTGGAAGCGTCGTGCGATCGGGGCGGTGTTATGTGGTGTCGTGTGGACGTTCCTGAA<br>GACATGTACATCCCAGTGCTCCCGAAGCGTGACCCGAGCGGGAAGTTATTGTTCCCGGTTGGTA<br>AGCTCGAGGGAGTGTGGACCCTGCCTGAGCTCCTGGAAGCGGAAAAGAATGGCTGTACGATCGA<br>GGCGATTTACCAGATGGTATACTGGGAGCATATGGAGCCGATCTTTAAAGAATTCGTTGAGCAC<br>TTTGAAGACCTCAAGAAGAACAGTAAGGGAGCGAAGCGCACCTTTGCAAAGCTTATCCAGAATA<br>GCTTGTACGGGAAGTTCGGCATGAACCGCGTTCGTGTGTCGTTGGGTGACATGGAAGACCGTTA<br>CGACTTGCATGAGAAGCAGATTCCATATAAAGAATTCAAACATGATTGTAATGGCTTGACGCTT<br>GAGTTCATCCAATATATCTCGGAAAGCAAAGCGAGCTATATTCAACCGCACATTGCTACATACG<br>TAACAGCCTATGCTCGTATCCTGTTGTTTCGTGGTCTGAAAGAACAGGCTAGCAAGGGCGTACT<br>GGGCTATTGCGATACTGACTCTATTGCCGGTACCGCCAAAATGCCGGACGAAATGATCCATGAC<br>GAAGATTACGGCAAGTGGGCCTTGGAAGGTGAGCTGGAAGAAGGTATCTTTCTCCAGCCGAAGT<br>TTTACGCGGAACGTTACACGAACGGCAAAGAAGTAATTAAGGCCAAGGGGATTCCACGCGAGAA<br>GATGGAAGAGTTAAGTTTCGAGAACTATAAAGAGTGGCTCGAGATTATGAAAGAAGGCCAACAA<br>GAGCGCATCGACATCTTTGAAGGTTACGAGAGTCGCAAGAAGTTTAGCACCACACTCAAGGCCA<br>GTGAAGATTTCGACACGTTGCGTGAGATGAAGAAGTCTATCAATTTACTGCTCGAGCAGAAGCG<br>CGACATCGACTACAAGGGCAACGTGACACGTCCACATAAGCGCTATGACTACGGTGGTGGCTCA<br>CATCACCACCATCATCAT | APolTr-His (nt) |
| 20 | GGCTCCAATAAGCAAAAGAAAGAGCGCCAAAAGCCGGCCAAGCTTCTCACCTTGGACACTGAGA<br>CGCGCGGCCTCACCGGTAATGTGTTCCGCGTTGGCCTGTTTGACGGGACGAATTATTACAAGTC<br>GAATACATTCGACGAGATCCTTGACCTGTTCGAGCAATATAAAGATTACGAATGTCATGTATAC<br>GTACACAATTTAGACTTCGACTTGGCGAAAATCGCCACCACTTTGTTCAAGCGCGACCGTGTGC<br>GCTTTGCGAAGAGCATCTTCATTAACGGTAACGTAGTGACTTTGCATTCGGACTCGATGATCTT<br>ACATGATAGCTTACGCTTACTGCCGGGGTCTCTGGAAAAGCTCTGTAAAGATTTTGGCCTGACC<br>GACAACGCCAAGAAAGATCTTTCCGAAGTCATCAAAGAGCAGGGTTACGCAGTATACAAGAAAG<br>ACGGTGTCACATTTGACAAGAAGAAATCCCTTGGCAATTATTTTGAGAACGTGCCTGCCGACGA<br>CCCTACGCTCAATGAGTACTTGGAGTTCGATTGTCGCAGCCTGTACGAGATTTTGACGATTGTG<br>ATGGACATCGCAAATATTGGCCTGGAAACCTTAGTAATGTGCCCGACCACAGCGAGCTTAGCCA<br>TGCGTGTCTATAAAGAGCAATACCGCGAGCAATATGATAAGGTGGCCACTCACTTTTATATGGG<br>CGAGTGGGTCAATTCCTCGAAGAGCACGTTCGCCAATCGTACTACGGTGGTCGCACTGAGGTA | APolTr-His-SET (nt) |

| SEQ ID NO | SEQUENCE | DESCRIPTION |
|---|---|---|
| | TTTACCCCTCATTTACCACATGGTTACCATTACGATGTTAACTCGTTGTACCCGTATGTCATGA<br>AAATTGCAAAGTTCCCGGTAGGGTACCCAAATTTATTGAAAGACGGCCAGGCAGCTACCAAGTG<br>GAAGCATTGGAAGCGTCGTGCGATCGGGGGCGGTGTTATGTGGTGTCGTGTGGACGTTCCTGAA<br>GACATGTACATCCCAGTGCTCCCGAAGCGTGACCCGAGCGGGAAGTTATTGTTCCCGGTTGGTA<br>AGCTCGAGGGAGTGTGGACCCTGCCTGAGCTCCTGGAAGCGGAAAAGAATGGCTGTACGATCGA<br>GGCGATTTACCAGATGGTATACTGGGAGCATATGGAGCCGATCTTTAAAGAATTCGTTGAGCAC<br>TTTGAAGACCTCAAGAAGAACAGTAAGGGAGCGAAGCGCACCTTTGCAAAGCTTATCCAGAATA<br>GCTTGTACGGGAAGTTCGGCATGAACCGCGTTCGTGTGTCGTTGGGTGACATGGAAGACCGTTA<br>CGACTTGCATGAGAAGCAGATTCCATATAAAGAATTCAAACATGATTGTAATGGCTTGACGCTT<br>GAGTTCATCCAATATATCTCGGAAAGCAAAGCGAGCTATATTCAACCGCACATTGCTACATACG<br>TAACAGCCTATGCTCGTATCCTGTTGTTTCGTGGTCTGAAAGAACAGGCTAGCAAGGGCGTACT<br>GGGCTATTGCGATACTGACTCTATTGCCGGTACCGCCAAAATGCCGGACGAAATGATCCATGAC<br>GAAGATTACGGCAAGTGGGCCTTGGAAGGTGAGCTGGAAGAAGGTATCTTTCTCCAGCCGAAGT<br>TTTACGCGGAACGTTACACGAACGGCAAAGAAGTAATTAAGGCCAAGGGGATTCCACGCGAGAA<br>GATGGAAGAGTTAAGTTTCGAGAACTATAAAGAGTGGCTCGAGATTATGAAAGAAGGCCAACAA<br>GAGCGCATCGACATCTTTGAAGGTTACGAGAGTCGCAAGAAGTTTAGCACCACACTCAAGGCCA<br>GTGAAGATTTCGACACGTTGCGTGAGATGAAGAAGTCTATCAATTTACTGCTCGAGCAGAAGCG<br>CGACATCGACTACAAGGGCAACGTGACACGTCCACATAAGCGCTATGACTACGGTGGTGGCTCA<br>CATCACCACCATCATCATTCAGAAGAGGACGAAGAGAAAGAAGAGGACGGGT | |
| 21 | GGCTCCAATAAGCAAAAGAAAGAGCGCCAAAAGCCGGCCAAGCTTCTCACCTTGGACACTGAGA<br>CGCGCGGCCTCACCGGTAATGTGTTCCGCGTTGGCCTGTTTGACGGGACGAATTATTACAAGTC<br>GAATACATTCGACGAGATCCTTGACCTGTTCGAGCAATATAAAGATTACGAATGTCATGTATAC<br>GTACACAATTTAGACTTCGACTTGGCGAAAATCGCCACCACTTTGTTCAAGCGCGACCGTGTGC<br>GCTTTGCGAAGAGCATCTTCATTAACGGTAACGTAGTGACTTGCATTCGGACTCGATGATCTT<br>ACATGATAGCTTACGCTTACTGCCGGGGTCTCTGAAAAGCTCTGTAAAGATTTTGGCCTGACC<br>GACAACGCCAAGAAAGATCTTTCCGAAGTCATCAAAGAGCAGGGTTACGCAGTATACAAGAAAG<br>ACGGTGTCACATTTGACAAGAAGAAATCCCTTGGCAATTATTTTGAGAACGTGCCTGCCGACGA<br>CCCTACGCTCAATGAGTACTTGGAGTTCGATTGTCGCAGCCGTACGAGATTTTGACGATTGTG<br>ATGGACATCGCAAATATTGGCCTGGAAACCTTAGTAATGTGCCCGACCACAGCGAGCTTAGCCA<br>TGCGTGTCTATAAAGAGCAATACCGCGAGCAATATGATAAGGTGGCCACTCACTTTTATATGGG<br>CGAGTGGGTCAATTCCTCGAAGAGCACGTTCGCCAATCGTACTACGGTGGTCGCACTGAGGTA<br>TTTACCCCTCATTTACCACATGGTTACCATTACGATGTTAACTCGTTGTACCCGTATGTCATGA<br>AAATTGCAAAGTTCCCGGTAGGGTACCCAAATTTATTGAAAGACGGCCAGGCAGCTACCAAGTG<br>GAAGCATTGGAAGCGTCGTGCGATCGGGGGCGGTGTTATGTGGTGTCGTGTGGACGTTCCTGAA<br>GACATGTACATCCCAGTGCTCCCGAAGCGTGACCCGAGCGGGAAGTTATTGTTCCCGGTTGGTA<br>AGCTCGAGGGAGTGTGGACCCTGCCTGAGCTCCTGGAAGCGGAAAAGAATGGCTGTACGATCGA<br>GGCGATTTACCAGATGGTATACTGGGAGCATATGGAGCCGATCTTTAAAGAATTCGTTGAGCAC<br>TTTGAAGACCTCAAGAAGAACAGTAAGGGAGCGAAGCGCACCTTTGCAAAGCTTATCCAGAATA<br>GCTTGTACGGGAAGTTCGGCATGAACCGCGTTCGTGTGTCGTTGGGTGACATGGAAGACCGTTA<br>CGACTTGCATGAGAAGCAGATTCCATATAAAGAATTCAAACATGATTGTAATGGCTTGACGCTT<br>GAGTTCATCCAATATATCTCGGAAAGCAAAGCGAGCTATATTCAACCGCACATTGCTACATACG<br>TAACAGCCTATGCTCGTATCCTGTTGTTTCGTGGTCTGAAAGAACAGGCTAGCAAGGGCGTACT<br>GGGCTATTGCGATACTGACTCTATTGCCGGTACCGCCAAAATGCCGGACGAAATGATCCATGAC<br>GAAGATTACGGCAAGTGGGCCTTGGAAGGTGAGCTGGAAGAAGGTATCTTTCTCCAGCCGAAGT<br>TTTACGCGGAACGTTACACGAACGGCAAAGAAGTAATTAAGGCCAAGGGGATTCCACGCGAGAA<br>GATGGAAGAGTTAAGTTTCGAGAACTATAAAGAGTGGCTCGAGATTATGAAAGAAGGCCAACAA<br>GAGCGCATCGACATCTTTGAAGGTTACGAGAGTCGCAAGAAGTTTAGCACCACACTCAAGGCCA<br>GTGAAGATTTCGACACGTTGCGTGAGATGAAGAAGTCTATCAATTTACTGCTCGAGCAGAAGCG<br>CGACATCGACTACAAGGGCAACGTGACACGTCCACATAAGCGCTATGACTACGGT | APolTr (nt) |
| 22 | AAGCACATGCCACGTAAAATGTATAGCTGTGATTTTGAGACTACGACGAAAGTTGAAGATTGCC<br>GTGTGTGGGCGTATGGTTACATGAATATTGAAGATCACTCCGAGTATAAGATTGGCAATAGCCT<br>GGATGAATTCATGGCGTGGGTGCTGAAGGTTCAGGCCGATTTGTACTTTCATAATCTGAAATTT<br>GATGGCGCTTTTATCATTAACTGGCTGGAGCGTAATGGTTTCAAGTGGAGCGCAGATGGCCTGC<br>CGAATACGTACAACACCATTATCAGCCGTATGGGCCAGTGGTACATGATCGACATCTGCCTGGG<br>CTATAAGGGTAAGCGTAAGATCCACACCGTGATTTATGACTCCCTGAAAAAGCTGCCGTTTCCG<br>GTGAAGAAAATTGCCAAAGACTTCAAGCTGACGGTTCTGAAGGGCGACATCGATTATCACAAGG<br>AACGTCCGGTTGGTTACAAGATCACCCCGGAAGAATACGCGTACATCAAAAACGACATTCAAAT<br>CATCGCAGAGGCCTTGCTGATTCAGTTCAAGCAAGGTCTGGACCGCATGACTGCCGGTAGCGAT<br>TCCCTGAAGGGTTTCAAAGACATTATCACCACCAAAAAGTTCAAAAAAGTGTTCCCGACGCTGA<br>GCCTGGGTCTGGATAAAGAGGTCCGTTACGCTTATCGTGGCGGCTTCACCTGGTTGAACGATCG<br>TTTCAAAGAAAAAGAAATTGGTGAGGGCATGGTTTTTGATGTTAACTCACTGTACCCGGCACAA<br>ATGTATAGCCGCCTGCTGCCGTATGGCGAGCCGATCGTGTTCGAGGGTAAATACGTGTGGGACG<br>AAGATTACCCGCTGCATATTCAACATATCCGCTGCGAGTTCGAGCTGAAGGAAGGCTACATCCC<br>GACCATTCAGATTAAGCGTAGCCGTTTTTACAAAGGTAATGAATACTTGAAGTCCTCGGGCGGT<br>GAGATTGCGGATCTGTGGTTAAGCAACGTCGACCTTGAGCTGATGAAAGAGCACTATGACCTCT<br>ATAACGTTGAGTACATTAGCGGTCTGAAATTCAAAGCCACGACGGGTCTGTTTAAAGACTTCAT<br>TGACAAGTGGACCTATATCAAGACGACGAGCGAGGGCGCGATCAAACAGCTGGCGAAGCTGATG<br>CTGAATTCTCTGTACGGTAAGTTTGCTAGCAATCCAGATGTCACCGGCAAAGTGCCGTATCTGA<br>AAGAAAACGGTGCGTTGGGTTTTCGCCTGGGTGAAGAGGAAACCAAAGATCCGGTGTACACCCC<br>GATGGGCGTTTTCATTACCGCGTGGGCTCGTTACACCACGATTACCGCAGCGCAGGCATGTTAT<br>GACCGTATCATTTACTGTGATACGGATAGCATTCACTTGACCGGTACCGAGATCCCAGATGTCA<br>TCAAAGATATTGTCGACCCGAAGAAACTGGGTTACTGGGCCCACGAAAGCACTTTCAAACGCGC | Phi29 WT (nt) |

| SEQ ID NO | SEQUENCE | DESCRIPTION |
|---|---|---|
| | AAAGTATCTGCGTCAGAAAACGTACATCCAAGACATTTACATGAAAGAGGTTGACGGCAAATTG<br>GTCGAGGGTTCGCCGGACGACTACACCGACATCAAGTTCAGCGTGAAGTGCGCGGGTATGACCG<br>ACAAAATCAAAAAAGAAGTCACCTTTGAGAACTTTAAGGTTGGTTTTAGCCGCAAGATGAAGCC<br>TAAACCGGTTCAGGTCCCGGGTGGCGTTGTGCTGGTCGACGACACCTTTACTATCAAG | |
| 23 | CATCACCACCATCATCAT | 6x His tag (nt) |
| 24 | TCAGAAGAGGACGAAGAGAAAGAAGAGGACGGGT | SET tag (nt) |
| 25 | GGTGGCTCA | GGSlinker (nt) |
| 26 | SDSEVNQEAKPEVKPEVKPETHINLKVSDGSSEIFFKIKKTTPLRRLMEAFAKROGKEMDSLRF<br>LYDGIRIQADQTPEDLDMEDNDIIEAHREQIGGS | SUMO tag (aa) |
| 27 | MGSNKQKKERQKPAKLLTLDTETRGLTGNVFRVGLFDGTNYYKSNTFDEILDLFEQYKDYECHV<br>YVHNLDFDLAKIATTLFKRDRVRFAKSIFINGNVVTLHSDSMILHDSLRLLPGSLEKLCKDFGL<br>TDNAKKDLSEVIKEQGYAVYKKDGVTFDKKKSLGNYFENVPADDPTLNEYLEFDCRSLYEILTI<br>VMDIANIGLETLVMCPTTASLAMRVYKEQYREQYDKVATHFYMGEWGQFLEEHVROSYYGGRTE<br>VFTPHLPHGYHYDVNSLYPYVMKIAKFPVGYPNLLKDGQAATKWKHWKRRAIGGGVMWCRVDVP<br>EDMYIPVLPKRDPSGKLLFPVGKLEGVWTLPELLEAEKNGCTIEAIYQMVYWEHMEPIFKEFVE<br>HFEDLKKNSKGAKRTFAKLIQNSLYGKFGMNRVRVSLGDMEDRYDLHEKQIPYKEFKHDCNGLT<br>LEFIQYISESKASYIQPHIATYVTAYARILLFRGLKEQAVLGYCDTDSIAGTAKMPDEMIH<br>DEDYGKWALEGELEEGIFLQPKFYAERYTNGKEVIKAKGIPREKMEELSFENYKEWLEIMKEGQ<br>QERIDIFEGYESRKKFSTTLKASEDFDTLREMKKSINLLLEQKRDIDYKGNVTRPHKRYDYGDK<br>KDKIDYEDYKSREDKLNNMYDDVDDLKEQVDEIGYIKCMKOGDMYFEEYKHLTKSVKSKYFRRT<br>GTPIDVWANESGWDVNELLEELRLMGVC | APo1 (aa) |
| 28 | MGSNKQKKERQKPAKLLTLDTETRGLTGNVFRVGLFDGTNYYKSNTFDEILDLFEQYKDYECHV<br>YVHNLDFDLAKIATTLFKRDRVRFAKSIFINGNVVTLHSDSMILHDSLRLLPGSLEKLCKDFGL<br>TDNAKKDLSEVIKEQGYAVYKKDGVTFDKKKSLGNYFENVPADDPTLNEYLEFDCRSLYEILTI<br>VMDIANIGLETLVMCPTTASLAMRVYKEQYREQYDKVATHFYMGEWGQFLEEHVRQSYYGGRTE<br>VFTPHLPHGYHYDVNSLYPYVMKIAKFPVGYPNLLKDGQAATKWKHWKRRAIGGGVMWCRVDVP<br>EDMYIPVLPKRDPSGKLLFPVGKLEGVWTLPELLEAEKNGCTIEAIYQMVYWEHMEPIFKEFVE<br>HFEDLKKNSKGAKRTFAKLIQNSLYGKFGMNRVRVSLGDMEDRYDLHEKQIPYKEFKHDCNGLT<br>LEFIQYISESKASYIQPHIATYVTAYARILLFRGLKEQASKGVLGYCDTDSIAGTAKMPDEMIH<br>DEDYGKWALEGELEEGIFLQPKFYAERYTNGKEVIKAKGIPREKMEELSFENYKEWLEIMKEGQ<br>QERIDIFEGYESRKKFSTTLKASEDFDTLREMKKSINLLLEQKRDIDYKGNVTRPHKRYDYGDK<br>KDKIDYEDYKSREDKLNNMYDDVDDLKEQVDEIGYIKCMKQGDMYFEEYKHLTKSVKSKYFRRT<br>GTPIDVWANESGWDVNELLEELRLMGVCGGSHHHHHH | APo1-His (aa) |
| 29 | MGSNKQKKERQKPAKLLTLDTETRGLTGNVFRVGLFDGTNYYKSNTFDEILDLFEQYKDYECHV<br>YVHNLDFDLAKIATTLFKRDRVRFAKSIFINGNVVTLHSDSMILHDSLRLLPGSLEKLCKDFGL<br>TDNAKKDLSEVIKEQGYAVYKKDGVTFDKKKSLGNYFENVPADDPTLNEYLEFDCRSLYEILTI<br>VMDIANIGLETLVMCPTTASLAMRVYKEQYREQYDKVATHFYMGEWGQFLEEHVROSYYGGRTE<br>VFTPHLPHGYHYDVNSLYPYVMKIAKFPVGYPNLLKDGQAATKWKHWKRRAIGGGVMWCRVDVP<br>EDMYIPVLPKRDPSGKLLFPVGKLEGVWTLPELLEAEKNGCTIEAIYQMVYWEHMEPIFKEFVE<br>HFEDLKKNSKGAKRTFAKLIQNSLYGKFGMNRVRVSLGDMEDRYDLHEKQIPYKEFKHDCNGLT<br>LEFIQYISESKASYIQPHIATYVTAYARILLFRGLKEQASKGVLGYCDTDSIAGTAKMPDEMIH<br>DEDYGKWALEGELEEGIFLQPKFYAERYTNGKEVIKAKGIPREKMEELSFENYKEWLEIMKEGQ<br>QERIDIFEGYESRKKFSTTLKASEDFDTLREMKKSINLLLEQKRDIDYKGNVTRPHKRYDYGGG<br>SHHHHHH | APo1Tr-His (aa) |
| 30 | MGSNKQKKERQKPAKLLTLDTETRGLTGNVFRVGLFDGTNYYKSNTFDEILDLFEQYKDYECHV<br>YVHNLDFDLAKIATTLFKRDRVRFAKSIFINGNVVTLHSDSMILHDSLRLLPGSLEKLCKDFGL<br>TDNAKKDLSEVIKEQGYAVYKKDGVTFDKKKSLGNYFENVPADDPTLNEYLEFDCRSLYEILTI<br>VMDIANIGLETLVMCPTTASLAMRVYKEQYREQYDKVATHFYMGEWGQFLEEHVRQSYYGGRTE<br>VFTPHLPHGYHYDVNSLYPYVMKIAKFPVGYPNLLKDGQAATKWKHWKRRAIGGGVMWCRVDVP<br>EDMYIPVLPKRDPSGKLLFPVGKLEGVWTLPELLEAEKNGCTIEAIYQMVYWEHMEPIFKEFVE<br>HFEDLKKNSKGAKRTFAKLIQNSLYGKFGMNRVRVSLGDMEDRYDLHEKQIPYKEFKHDCNGLT<br>LEFIQYISESKASYIQPHIATYVTAYARILLFRGLKEQASKGVLGYCDTDSIAGTAKMPDEMIH<br>DEDYGKWALEGELEEGIFLQPKFYAERYTNGKEVIKAKGIPREKMEELSFENYKEWLEIMKEGQ<br>QERIDIFEGYESRKKFSTTLKASEDFDTLREMKKSINLLLEQKRDIDYKGNVTRPHKRYDYGGG<br>SHHHHHHSEEDEEKEEDG | APo1Tr-His-SET (aa) |
| 31 | MKHMPRKMYSCDFETTTKVEDCRVWAYGYMNIEDHSEYKIGNSLDEFMAWVLKVQADLYFHNLK<br>FDGAFIINWLERNGFKWSADGLPNTYNTIISRMGQWYMIDICLGYKGKRKIHTVIYDSLKKLPF<br>PVKKIAKDFKLTVLKGDIDYHKERPVGYKITPEEYAYIKNDIQIIAEALLIQFKOGLDRMTAGS<br>DSLKGFKDIITTKKFKKVFPTLSLGLDKEVRYAYRGGFTWLNDRFKEKEIGEGMVFDVNSLYPA<br>QMYSRLLPYGEPIVFEGKYVWDEDYPLHIQHIRCEFELKEGYIPTIQIKRSRFYKGNEYLKSSG<br>GEIADLWLSNVDLELMKEHYDLYNVEYISGLKFKATTGLFKDFIDKWTYIKTTSEGAIKOLAKL<br>MLNSLYGKFASNPDVTGKVPYLKENGALGFRLGEEETKDPVYTPMGVFITAWARYTTITAAQAC | Phi29 WT (aa) |

| SEQ ID NO | SEQUENCE | DESCRIPTION |
|---|---|---|
| | YDRIIYCDTDSIHLTGTEIPDVIKDIVDPKKLGYWAHESTFKRAKYLROKTYIQDIYMKEVDGK<br>LVEGSPDDYTDIKFSVKCAGMTDKIKKEVTFENFKVGFSRKMKPKPVQVPGGVVLVDDTFTIK | |
| 32 | MGSNKQKKERQKPAKLLTLDTETRGLTGNVFRVGLFDGTNYYKSNTFDEILDLFEQYKDYECHV<br>YVHNLDFDLAKIATTLFKRDRVRFAKSIFINGNVVTLHSDSMILHDSLRLLPGSLEKLCKDFGL<br>TDNAKKDLSEVIKEQGYAVYKKDGVTFDKKKSLGNYFENVPADDPTLNEYLEFDCRSLYEILTI<br>VMDIANIGLETLVMCPTTASLAMRVYKEQYREQYDKVATHFYMGEWGQFLEEHVRQSYYGGRTE<br>VFTPHLPHGYHYDVNSLYPYVMKIAKFPVGYPNLLKDGQAATKWKHWKRRAIGGGVMWCRVDVP<br>EDMYIPVLPKRDPSGKLLFPVGKLEGVWTLPELLEAEKNGCTIEAIYQMVYWEHMEPIFKEFVE<br>HFEDLKKNSKGAKRTFAKLIQNSLYGKFGMNRVRVSLGDMEDRYDLHEKQIPYKEFKHDCNGLT<br>LEFIQYISESKASYIQPHIATYVTAYARILLFRGLKEQASKGVLGYCDTDSIAGTAKMPDEMIH<br>DEDYGKWALEGELEEGIFLQPKFYAERYTNGKEVIKAKGIPREKMEELSFENYKEWLEIMKEGQ<br>QERIDIFEGYESRKKESTTLKASEDFDTLREMKKSINLLLEQKRDIDYKGNVTRPHKRYDYG | APolTr (aa) |
| 33 | ATGGGCTCCAATAAGCAAAAGAAAGAGCGCCAAAAGCCGGCCAAGCTTCTCACCTTGGACACTG<br>AGACGCGCGGCCTCACCGGTAATGTGTTCCGCGTTGGCCTGTTTGACGGGACGAATTATTACAA<br>GTCGAATACATTCGACGAGATCCTTGACCTGTTCGAGCAATATAAAGATTACGAATGTCATGTA<br>TACGTACACAATTTAGACTTCGACTTGGCGAAAATCGCCACCACTTTGTTCAAGCGCGACCGTG<br>TGCGCTTTGCGAAGAGCATCTTCATTAACGGTAACGTAGTGACTTTGCATTCGGACTCGATGAT<br>CTTACATGATAGCTTACGCTTACTGCCGGGGTCTCTGGAAAAGCTCTGTAAAGATTTTGGCCTG<br>ACCGACAACGCCAAGAAAGATCTTTCCGAAGTCATCAAAGAGCAGGGTTACGCAGTATACAAGA<br>AAGACGGTGTCACATTTGACAAGAAGAAATCCCTTGGCAATTATTTTGAGAACGTGCCTGCCGA<br>CGACCCTACGCTCAATGAGTACTTGGAGTTCGATTGTCGCAGCCTGTACGAGATTTTGACGATT<br>GTGATGGACATCGCAAATATTGGCCTGGAAACCTTAGTAATGTGCCCGACCACAGCGAGCTTAG<br>CCATGCGTGTCTATAAAGAGCAATACCGCGAGCAATATGATAAGGTGGCCACTCACTTTTATAT<br>GGGCGAGTGGGGTCAATTCCTCGAAGAGCACGTTCGCCAATCGTACTACGGTGGTCGCACTGAG<br>GTATTTACCCCTCATTTACCACATGGTTACCATTACGATGTTAACTCGTTGTACCCGTATGTCA<br>TGAAAATTGCAAAGTTCCCGGTAGGGTACCCAAATTTATTGAAAGACGGCCAGGCAGCTACCAA<br>GTGGAAGCATTGGAAGCGTCGTGCGATCGGGGCGGTGTTATGGTGTCGTGTGGACGTTCCT<br>GAAGACATGTACATCCCAGTGCTCCCGAAGCGTGACCCGAGCGGGAAGTTATTGTTCCCGGTTG<br>GTAAGCTCGAGGGAGTGTGGACCCTGCCTGAGCTCCTGGAAGCGGAAAAGAATGGCTGTACGAT<br>CGAGGCGATTTACCAGATGGTATACTGGGAGCATATGGAGCCGATCTTTAAAGAATTCGTTGAG<br>CACTTTGAAGACCTCAAGAAGAACAGTAAGGGAGCGAAGCGCACCTTTGCAAAGCTTATCCAGA<br>ATAGCTTGTACGGGAAGTTCGGCATGAACCGCGTTCGTGTGTCGTTGGGTGACATGGAAGACCG<br>TTACGACTTGCATGAGAAGCAGATTCCATATAAAGAATTCAAACATGATTGTAATGGCTTGACG<br>CTTGAGTTCATCCAATATATCTCGGAAAGCAAAGCGAGCTATATTCAACCGCACATTGCTACAT<br>ACGTAACAGCCTATGCTCGTATCCTGTTGTTTCGTGGTCTGAAAGAACAGGCTAGCAAGGGCGT<br>ACTGGGCTATTGCGATACTGACTCTATTGCCGGTACCGCCAAAATGCCGGACGAAATGATCCAT<br>GACGAAGATTACGGCAAGTGGGCCTTGGAAGGTGAGCTGGAAGAAGGTATCTTTCTCCAGCCGA<br>AGTTTTACGCGGAACGTTACACGAACGGCAAAGAAGTAATTAAGGCCAAGGGGATTCCACGCGA<br>GAAGATGGAAGAGTTAAGTTTCGAGAACTATAAAGAGTGGCTCGAGATTATGAAGAAGGCCAA<br>CAAGAGCGCATCGACATCTTTGAAGGTTACGAGAGTCGCAAGAAGTTTAGCACCACACTCAAGG<br>CCAGTGAAGATTTCGACACGTTGCGTGAGATGAAGAAGTCTATCAATTTACTGCTCGAGCAGAA<br>GCGCGACATCGACTACAAGGGCAACGTGACACGTCCACATAAGCGCTATGACTACGGTGATAAG<br>AAAGACAAGATCGATTATGAAGACTATAAGAGCCGTGAAGACAAGTTAAACAACATGTACGACG<br>ATGTAGACGACTTAAAAGAGCAAGTTGACGAGATCGGCTACATCAAGTGCATGAAGCAAGGCGA<br>TATGTATTTTGAAGAGTACAAACATCTTACGAAGTCTGTGAAAAGTAAGTATTTCCGCCGCACT<br>GGCACCCCAATCGACGTATGGGCGAACGAATCCGGTTGGGACGTAAACGAGTTATTAGAAGAGC<br>TTCGTCTGATGGGCGTGTGC | APol (nt) |
| 34 | ATGGGCTCCAATAAGCAAAAGAAAGAGCGCCAAAAGCCGGCCAAGCTTCTCACCTTGGACACTG<br>AGACGCGCGGCCTCACCGGTAATGTGTTCCGCGTTGGCCTGTTTGACGGGACGAATTATTACAA<br>GTCGAATACATTCGACGAGATCCTTGACCTGTTCGAGCAATATAAAGATTACGAATGTCATGTA<br>TACGTACACAATTTAGACTTCGACTTGGCGAAAATCGCCACCACTTTGTTCAAGCGCGACCGTG<br>TGCGCTTTGCGAAGAGCATCTTCATTAACGGTAACGTAGTGACTTTGCATTCGGACTCGATGAT<br>CTTACATGATAGCTTACGCTTACTGCCGGGGTCTCTGGAAAAGCTCTGTAAAGATTTTGGCCTG<br>ACCGACAACGCCAAGAAAGATCTTTCCGAAGTCATCAAAGAGCAGGGTTACGCAGTATACAAGA<br>AAGACGGTGTCACATTTGACAAGAAGAAATCCCTTGGCAATTATTTTGAGAACGTGCCTGCCGA<br>CGACCCTACGCTCAATGAGTACTTGGAGTTCGATTGTCGCAGCCTGTACGAGATTTTGACGATT<br>GTGATGGACATCGCAAATATTGGCCTGGAAACCTTAGTAATGTGCCCGACCACAGCGAGCTTAG<br>CCATGCGTGTCTATAAAGAGCAATACCGCGAGCAATATGATAAGGTGGCCACTCACTTTTATAT<br>GGGCGAGTGGGGTCAATTCCTCGAAGAGCACGTTCGCCAATCGTACTACGGTGGTCGCACTGAG<br>GTATTTACCCCTCATTTACCACATGGTTACCATTACGATGTTAACTCGTTGTACCCGTATGTCA<br>TGAAAATTGCAAAGTTCCCGGTAGGGTACCCAAATTTATTGAAAGACGGCCAGGCAGCTACCAA<br>GTGGAAGCATTGGAAGCGTCGTGCGATCGGGGCGGTGTTATGGTGTCGTGTGGACGTTCCT<br>GAAGACATGTACATCCCAGTGCTCCCGAAGCGTGACCCGAGCGGGAAGTTATTGTTCCCGGTTG<br>GTAAGCTCGAGGGAGTGTGGACCCTGCCTGAGCTCCTGGAAGCGGAAAAGAATGGCTGTACGAT<br>CGAGGCGATTTACCAGATGGTATACTGGGAGCATATGGAGCCGATCTTTAAAGAATTCGTTGAG<br>CACTTTGAAGACCTCAAGAAGAACAGTAAGGGAGCGAAGCGCACCTTTGCAAAGCTTATCCAGA<br>ATAGCTTGTACGGGAAGTTCGGCATGAACCGCGTTCGTGTGTCGTTGGGTGACATGGAAGACCG<br>TTACGACTTGCATGAGAAGCAGATTCCATATAAAGAATTCAAACATGATTGTAATGGCTTGACG<br>CTTGAGTTCATCCAATATATCTCGGAAAGCAAAGCGAGCTATATTCAACCGCACATTGCTACAT<br>ACGTAACAGCCTATGCTCGTATCCTGTTGTTTCGTGGTCTGAAAGAACAGGCTAGCAAGGGCGT<br>ACTGGGCTATTGCGATACTGACTCTATTGCCGGTACCGCCAAAATGCCGGACGAAATGATCCAT | APol-His (nt) |

| SEQ ID NO | SEQUENCE | DESCRIPTION |
|---|---|---|
| | GACGAAGATTACGGCAAGTGGGCCTTGGAAGGTGAGCTGGAAGAAGGTATCTTTCTCCAGCCGA<br>AGTTTTACGCGGAACGTTACACGAACGGCAAAGAAGTAATTAAGGCCAAGGGGATTCCACGCGA<br>GAAGATGGAAGAGTTAAGTTTCGAGAACTATAAAGAGTGGCTCGAGATTATGAAGAAGGCCAA<br>CAAGAGCGCATCGACATCTTTGAAGGTTACGAGAGTCGCAAGAAGTTTAGCACCACACTCAAGG<br>CCAGTGAAGATTTCGACACGTTGCGTGAGATGAAGAAGTCTATCAATTTACTGCTCGAGCAGAA<br>GCGCGACATCGACTACAAGGGCAACGTGACACGTCCACATAAGCGCTATGACTACGGTGATAAG<br>AAAGACAAGATCGATTATGAAGACTATAAGAGCCGTGAAGACAAGTTAAACAACATGTACGACG<br>ATGTAGACGACTTAAAAGAGCAAGTTGACGAGATCGGCTACATCAAGTGCATGAAGCAAGGCGA<br>TATGTATTTTGAAGAGTACAAACATCTTACGAAGTCTGTGAAAAGTAAGTATTTCCGCCGCACT<br>GGCACCCCAATCGACGTATGGGCGAACGAATCCGGTTGGGACGTAAACGAGTTATTAGAAGAGC<br>TTCGTCTGATGGGCGTGTGCGGTGGCTCACATCACCACCATCATCAT | |
| 35 | ATGGGCTCCAATAAGCAAAAGAAAGAGCGCCAAAAGCCGGCCAAGCTTCTCACCTTGGACACTG<br>AGACGCGCGGCCTCACCGGTAATGTGTTCCGCGTTGGCCTGTTTGACGGGACGAATTATTACAA<br>GTCGAATACATTCGACGAGATCCTTGACCTGTTCGAGCAATATAAAGATTACGAATGTCATGTA<br>TACGTACACAATTTAGACTTCGACTTGGCGAAAATCGCCACCACTTTGTTCAAGCGCGACCGTG<br>TGCGCTTTGCGAAGAGCATCTTCATTAACGGTAACGTAGTGACTTTGCATTCGGACTCGATGAT<br>CTTACATGATAGCTTACGCTTACTGCCGGGGTCTCTGGAAAAGCTCTGTAAAGATTTTGGCCTG<br>ACCGACAACGCCAAGAAAGATCTTTCCGAAGTCATCAAAGAGCAGGGTTACGCAGTATACAAGA<br>AAGACGGTGTCACATTTGACAAGAAGAAATCCCTTGGCAATTATTTTGAGAACGTGCCTGCCGA<br>CGACCCTACGCTCAATGAGTACTTGGAGTTCGATTGTCGCAGCCTGTACGAGATTTTGACGATT<br>GTGATGGACATCGCAAATATTGGCCTGGAAACCTTAGTAATGTGCCCGACCACAGCGAGCTTAG<br>CCATGCGTGTCTATAAAGAGCAATACCGCGAGCAATATGATAAGGTGGCCACTCACTTTTATAT<br>GGGCGAGTGGGGTCAATTCCTCGAAGAGCACGTTCGCCAATCGTACTACGGTGGTCGCACTGAG<br>GTATTTACCCCTCATTTACCACATGGTTACCATTACGATGTTAACTCGTTGTACCCGTATGTCA<br>TGAAAATTGCAAAGTTCCCGGTAGGGTACCCAAATTTATTGAAAGACGGCCAGGCAGCTACCAA<br>GTGGAAGCATTGGAAGCGTCGTGCGATCGGGGCGGTGTTATGTGGTGTCGTGTGGACGTTCCT<br>GAAGACATGTACATCCCAGTGCTCCCGAAGCGTGACCCGAGCGGGAAGTTATTGTTCCCGGTTG<br>GTAAGCTCGAGGGAGTGTGGACCCTGCCTGAGCTCCTGGAAGCGGAAAAGAATGGCTGTACGAT<br>CGAGGCGATTTACCAGATGGTATACTGGGAGCATATGGAGCCGATCTTTAAAGAATTCGTTGAG<br>CACTTTGAAGACCTCAAGAAGAACAGTAAGGGAGCGAAGCGCACCTTTGCAAAGCTTATCCAGA<br>ATAGCTTGTACGGGAAGTTCGGCATGAACCGCGTTCGTGTGTCGTTGGGTGACATGGAAGACCG<br>TTACGACTTGCATGAGAAGCAGATTCCATATAAAGAATTCAAACATGATTGTAATGGCTTGACG<br>CTTGAGTTCATCCAATATATCTCGGAAAGCAAAGCGAGCTATATTCAACCGCACATTGCTACAT<br>ACGTAACAGCCTATGCTCGTATCCTGTTGTTTCGTGGTCTGAAAGAACAGGCTAGCAAGGGCGT<br>ACTGGGCTATTGCGATACTGACTCTATTGCCGGTACCGCCAAAATGCCGGACGAAATGATCCAT<br>GACGAAGATTACGGCAAGTGGGCCTTGGAAGGTGAGCTGGAAGAAGGTATCTTTCTCCAGCCGA<br>AGTTTTACGCGGAACGTTACACGAACGGCAAAGAAGTAATTAAGGCCAAGGGGATTCCACGCGA<br>GAAGATGGAAGAGTTAAGTTTCGAGAACTATAAAGAGTGGCTCGAGATTATGAAGAAGGCCAA<br>CAAGAGCGCATCGACATCTTTGAAGGTTACGAGAGTCGCAAGAAGTTTAGCACCACACTCAAGG<br>CCAGTGAAGATTTCGACACGTTGCGTGAGATGAAGAAGTCTATCAATTTACTGCTCGAGCAGAA<br>GCGCGACATCGACTACAAGGGCAACGTGACACGTCCACATAAGCGCTATGACTACGGTGGTGGC<br>TCACATCACCACCATCATCAT | APolTr-His (nt) |
| 36 | ATGGGCTCCAATAAGCAAAAGAAAGAGCGCCAAAAGCCGGCCAAGCTTCTCACCTTGGACACTG<br>AGACGCGCGGCCTCACCGGTAATGTGTTCCGCGTTGGCCTGTTTGACGGGACGAATTATTACAA<br>GTCGAATACATTCGACGAGATCCTTGACCTGTTCGAGCAATATAAAGATTACGAATGTCATGTA<br>TACGTACACAATTTAGACTTCGACTTGGCGAAAATCGCCACCACTTTGTTCAAGCGCGACCGTG<br>TGCGCTTTGCGAAGAGCATCTTCATTAACGGTAACGTAGTGACTTTGCATTCGGACTCGATGAT<br>CTTACATGATAGCTTACGCTTACTGCCGGGGTCTCTGGAAAAGCTCTGTAAAGATTTTGGCCTG<br>ACCGACAACGCCAAGAAAGATCTTTCCGAAGTCATCAAAGAGCAGGGTTACGCAGTATACAAGA<br>AAGACGGTGTCACATTTGACAAGAAGAAATCCCTTGGCAATTATTTTGAGAACGTGCCTGCCGA<br>CGACCCTACGCTCAATGAGTACTTGGAGTTCGATTGTCGCAGCCTGTACGAGATTTTGACGATT<br>GTGATGGACATCGCAAATATTGGCCTGGAAACCTTAGTAATGTGCCCGACCACAGCGAGCTTAG<br>CCATGCGTGTCTATAAAGAGCAATACCGCGAGCAATATGATAAGGTGGCCACTCACTTTTATAT<br>GGGCGAGTGGGGTCAATTCCTCGAAGAGCACGTTCGCCAATCGTACTACGGTGGTCGCACTGAG<br>GTATTTACCCCTCATTTACCACATGGTTACCATTACGATGTTAACTCGTTGTACCCGTATGTCA<br>TGAAAATTGCAAAGTTCCCGGTAGGGTACCCAAATTTATTGAAAGACGGCCAGGCAGCTACCAA<br>GTGGAAGCATTGGAAGCGTCGTGCGATCGGGGCGGTGTTATGTGGTGTCGTGTGGACGTTCCT<br>GAAGACATGTACATCCCAGTGCTCCCGAAGCGTGACCCGAGCGGGAAGTTATTGTTCCCGGTTG<br>GTAAGCTCGAGGGAGTGTGGACCCTGCCTGAGCTCCTGGAAGCGGAAAAGAATGGCTGTACGAT<br>CGAGGCGATTTACCAGATGGTATACTGGGAGCATATGGAGCCGATCTTTAAAGAATTCGTTGAG<br>CACTTTGAAGACCTCAAGAAGAACAGTAAGGGAGCGAAGCGCACCTTTGCAAAGCTTATCCAGA<br>ATAGCTTGTACGGGAAGTTCGGCATGAACCGCGTTCGTGTGTCGTTGGGTGACATGGAAGACCG<br>TTACGACTTGCATGAGAAGCAGATTCCATATAAAGAATTCAAACATGATTGTAATGGCTTGACG<br>CTTGAGTTCATCCAATATATCTCGGAAAGCAAAGCGAGCTATATTCAACCGCACATTGCTACAT<br>ACGTAACAGCCTATGCTCGTATCCTGTTGTTTCGTGGTCTGAAAGAACAGGCTAGCAAGGGCGT<br>ACTGGGCTATTGCGATACTGACTCTATTGCCGGTACCGCCAAAATGCCGGACGAAATGATCCAT<br>GACGAAGATTACGGCAAGTGGGCCTTGGAAGGTGAGCTGGAAGAAGGTATCTTTCTCCAGCCGA | APolTr-His-SET (nt) |

| SEQ ID NO | SEQUENCE | DESCRIPTION |
|---|---|---|
| | AGTTTTACGCGGAACGTTACACGAACGGCAAAGAAGTAATTAAGGCCAAGGGGATTCCACGCGA<br>GAAGATGGAAGAGTTAAGTTTCGAGAACTATAAAGAGTGGCTCGAGATTATGAAAGAAGGCCAA<br>CAAGAGCGCATCGACATCTTTGAAGGTTACGAGAGTCGCAAGAAGTTTAGCACCACACTCAAGG<br>CCAGTGAAGATTTCGACACGTTGCGTGAGATGAAGAAGTCTATCAATTTACTGCTCGAGCAGAA<br>GCGCGACATCGACTACAAGGGCAACGTGACACGTCCACATAAGCGCTATGACTACGGTGGTGGC<br>TCACATCACCACCATCATCATTCAGAAGAGGACGAAGAGAAAGAAGAGGACGGGT | |
| 37 | ATGGGCTCCAATAAGCAAAAGAAAGAGCGCCAAAAGCCGGCCAAGCTTCTCACCTTGGACACTG<br>AGACGCGCGGCCTCACCGGTAATGTGTTCCGCGTTGGCCTGTTTGACGGGACGAATTATTACAA<br>GTCGAATACATTCGACGAGATCCTTGACCTGTTCGAGCAATATAAAGATTACGAATGTCATGTA<br>TACGTACACAATTTAGACTTCGACTTGGCGAAAATCGCCACCACTTTGTTCAAGCGCGACCGTG<br>TGCGCTTTGCGAAGAGCATCTTCATTAACGGTAACGTAGTGACTTTGCATTCGGACTCGATGAT<br>CTTACATGATAGCTTACGCTTACTGCCGGGGTCTCTGGAAAAGCTCTGTAAAGATTTTGGCCTG<br>ACCGACAACGCCAAGAAAGATCTTTCCGAAGTCATCAAAGAGCAGGGTTACGCAGTATACAAGA<br>AAGACGGTGTCACATTTGACAAGAAGAAATCCCTTGGCAATTATTTTGAGAACGTGCCTGCCGA<br>CGACCCTACGCTCAATGAGTACTTGGAGTTCGATTGTCGCAGCCTGTACGAGATTTTGACGATT<br>GTGATGGACATCGCAAATATTGGCCTGGAAACCTTAGTAATGTGCCCGACCACAGCGAGCTTAG<br>CCATGCGTGTCTATAAAGAGCAATACCGCGAGCAATATGATAAGGTGGCCACTCACTTTTATAT<br>GGGCGAGTGGGGTCAATTCCTCGAAGAGCACGTTCGCCAATCGTACTACGGTGGTCGCACTGAG<br>GTATTTACCCCTCATTTACCACATGGTTACCATTACGATGTTAACTCGTTGTACCCGTATGTCA<br>TGAAAATTGCAAAGTTCCCGGTAGGGTACCCAAATTTATTGAAAGACGGCCAGGCAGCTACCAA<br>GTGGAAGCATTGGAAGCGTCGTGCGATCGGGGCGGTGTTATGTGGTGTCGTGTGGACGTTCCT<br>GAAGACATGTACATCCCAGTGCTCCCGAAGCGTGACCCGAGCGGGAAGTTATTGTTCCCGGTTG<br>GTAAGCTCGAGGGAGTGTGGACCCTGCCTGAGCTCCTGGAAGCGGAAAAGAATGGCTGTACGAT<br>CGAGGCGATTTACCAGATGGTATACTGGGAGCATATGGAGCCGATCTTTAAAGAATTCGTTGAG<br>CACTTTGAAGACCTCAAGAAGAACAGTAAGGGAGCGAAGCGCACCTTTGCAAAGCTTATCCAGA<br>ATAGCTTGTACGGGAAGTTCGGCATGAACCGCGTTCGTGTGTCGTTGGGTGACATGGAAGACCG<br>TTACGACTTGCATGAGAAGCAGATTCCATATAAAGAATTCAAACATGATTGTAATGGCTTGACG<br>CTTGAGTTCATCCAATATATCTCGGAAAGCAAAGCGAGCTATATTCAACCGCACATTGCTACAT<br>ACGTAACAGCCTATGCTCGTATCCTGTTGTTTCGTGGTCTGAAAGAACAGGCTAGCAAGGGCGT<br>ACTGGGCTATTGCGATACTGACTCTATTGCCGGTACCGCCAAAATGCCGGACGAAATGATCCAT<br>GACGAAGATTACGGCAAGTGGGCCTTGGAAGGTGAGCTGGAAGAAGGTATCTTTCTCCAGCCGA<br>AGTTTTACGCGGAACGTTACACGAACGGCAAAGAAGTAATTAAGGCCAAGGGGATTCCACGCGA<br>GAAGATGGAAGAGTTAAGTTTCGAGAACTATAAAGAGTGGCTCGAGATTATGAAAGAAGGCCAA<br>CAAGAGCGCATCGACATCTTTGAAGGTTACGAGAGTCGCAAGAAGTTTAGCACCACACTCAAGG<br>CCAGTGAAGATTTCGACACGTTGCGTGAGATGAAGAAGTCTATCAATTTACTGCTCGAGCAGAA<br>GCGCGACATCGACTACAAGGGCAACGTGACACGTCCACATAAGCGCTATGACTACGGT | APolTr (nt) |
| 38 | ATGAAGCACATGCCACGTAAAATGTATAGCTGTGATTTTGAGACTACGACGAAAGTTGAAGATT<br>GCCGTGTGTGGGCGTATGGTTACATGAATATTGAAGATCACTCCGAGTATAAGATTGGCAATAG<br>CCTGGATGAATTCATGGCGTGGGTGCTGAAGGTTCAGGCCGATTTGTACTTTCATAATCTGAAA<br>TTTGATGGCGCTTTTATCATTAACTGGCTGGAGCGTAATGGTTTCAAGTGGAGCGCAGATGGCC<br>TGCCGAATACGTACAACACCATTATCAGCCGTATGGGCCAGTGGTACATGATCGACATCTGCCT<br>GGGCTATAAGGGTAAGCGTAAGATCCACACCGTGATTTATGACTCCCTGAAAAAGCTGCCGTTT<br>CCGGTGAAGAAAATTGCCAAAGACTTCAAGCTGACGGTTCTGAAGGGCGACATCGATTATCACA<br>AGGAACGTCCGGTTGGTTACAAGATCACCCCGGAAGAATACGCGTACATCAAAAACGACATTCA<br>AATCATCGCAGAGGCCTTGCTGATTCAGTTCAAGCAAGGTCTGGACCGCATGACTGCCGGTAGC<br>GATTCCCTGAAGGGTTTCAAAGACATTATCACCACCAAAAAGTTCAAAAAAGTCTCAAAAAGTGTTCCCGACGC<br>TGAGCCTGGGTCTGGATAAAGAGGTCCGTTACGCTTATCGTGGCGGCTTCACCTGGTTGAACGA<br>TCGTTTCAAAGAAAAGAAATTGGTGAGGGCATGGTTTTTGATGTTAACTCACTGTACCCGGCA<br>CAAATGTATAGCCGCCTGCTGCCGTATGGCGAGCCGATCGTGTTCGAGGGTAAATACGTGTGGG<br>ACGAAGATTACCCGCTGCATATTCAACATATCCGCTGCGAGTTCGAGCTGAAGGAAGGCTACAT<br>CCCGACCATTCAGATTAAGCGTAGCCGTTTTTACAAAGGTAATGAATACTTGAAGTCCTCGGGC<br>GGTGAGATTGCGGATCTGTGGTTAAGCAACGTCGACCTTGAGCTGATGAAAGAGCACTATGACC<br>TCTATAACGTTGAGTACATTAGCGGTCTGAAATTCAAAGCCACGACGGTCTGTTTAAAGACTT<br>CATTGACAAGTGGACCTATATCAAGACGACGAGCGAGGGCGCGATCAAACAGCTGGCGAAGCTG<br>ATGCTGAATTCTCTGTACGGTAAGTTTGCTAGCAATCCAGATGTCACCGGCAAAGTGCCGTATC<br>TGAAAGAAAACGGTGCGTTGGGTTTTCGCCTGGGTGAAGAGGAAACCAAAGATCCGGTTGTACAC<br>CCCGATGGGCGTTTTCATTACCGCGTGGGCTCGTTACACCACGATTACCGCAGCGCAGGCATGT<br>TATGACCGTATCATTTACTGTGATACGGATAGCATTCACTTGACCGGTACCGAGATCCCAGATG<br>TCATCAAAGATATTGTCGACCCGAAGAAACTGGGTTACTGGGCCCACGAAAGCACTTTCAAACG<br>CGCAAAGTATCTGCGTCAGAAAACGTACATCCAAGCACATTTACATGAAAGAGGTTGACGGCAAA<br>TTGGTCGAGGGTTCGCCGGACGACTACACCGACATCAAGTTCAGCGTGAAGTGCGCGGGTATGA<br>CCGACAAAATCAAAAAGAAGTCACCTTTGAGAACTTTAAGGTTGGTTTTAGCCGCAAGATGAA<br>GCCTAAACCGGTTCAGGTCCCGGGTGGCGTTGTGCTGGTCGACGACACCTTTACTATCAAG | Phi29 WT (nt) |

The invention claimed is:

1. A method for nucleic acid amplification, the method comprising contacting a biological sample comprising a nucleic acid to be amplified with a recombinant *Bacillus* phage AP50 polymerase, wherein the nucleic acid is amplified by rolling circle amplification (RCA) using the recombinant polymerase.

2. The method of claim 1, wherein the recombinant polymerase comprises:
   a sequence set forth in SEQ ID NO:6,
   a contiguous portion of SEQ ID NO:6 of at least 200 amino acids in length, or
   a sequence that has at least 95% sequence identity to any of the foregoing.

3. The method of claim 1, wherein the recombinant polymerase comprises:
   a sequence set forth in SEQ ID NO: 1,
   a contiguous portion of SEQ ID NO:1 of at least 637 amino acids in length, or
   a sequence that has at least 95% sequence identity to any of the foregoing.

4. The method of claim 1, wherein the recombinant polymerase comprises one or more amino acid substitutions, deletions or additions at one or more positions, corresponding to the positions of the sequence set forth in SEQ ID NO:1.

5. The method of claim 1, wherein the recombinant polymerase comprises a heterologous sequence, and wherein the heterologous sequence comprises one or more tags.

6. The method of claim 5, wherein the tag is a poly histidine (HIS) tag.

7. The method of claim 1, wherein the recombinant polymerase comprises the sequence set forth in SEQ ID NO:6, a linker, and a poly histidine (HIS) tag.

8. The method of claim 1, wherein the recombinant polymerase comprises the sequence set forth in any one of SEQ ID NOS:2-4 or a sequence that has at least 95% sequence identity to the sequence set forth in any one of SEQ ID NOS:2-4.

9. The method of claim 1, wherein the recombinant polymerase is 638 amino acids or less in length.

10. The method of claim 1, wherein the nucleic acid comprises deoxyribonucleotide residues, the nucleic acid comprises one or more ribonucleotide residues, and/or the nucleic acid is a circular probe or a circularizable probe that is circularized by ligating the circularizable probe to generate a circularized probe.

11. The method of claim 1, wherein the nucleic acid is amplified in situ in the biological sample using the recombinant polymerase, wherein the biological sample is a cell sample or a tissue sample.

12. The method of claim 1, further comprising incubating the recombinant polymerase and the biological sample with a primer that hybridizes to the nucleic acid.

13. The method of claim 1, wherein the recombinant polymerase has strand displacement activity.

14. The method of claim 1, wherein the recombinant polymerase exhibits one or more features selected from among improved processivity, improved polymerization rate, and improved thermostability, compared to a reference polymerase, wherein the reference polymerase is a Phi29 polymerase.

15. The method of claim 1, wherein the RCA is performed at a temperature of between 30° C. and 55° C.

16. The method of claim 1, further comprising detecting or analyzing an amplification product generated by the RCA using the recombinant polymerase.

17. The method of claim 16, wherein the amplification product is detected or analyzed by sequential hybridization, sequencing by hybridization, sequencing by ligation, sequencing by synthesis, sequencing by binding, or a combination thereof.

18. The method of claim 16, wherein the amplification product comprises one or more barcode sequences.

19. The method of claim 18, wherein the one or more barcode sequences correspond to a target nucleic acid or an endogenous analyte and/or the one or more barcode sequences are detected by:
   (i) contacting the biological sample with one or more detectably-labeled probes that directly or indirectly bind to the one or more barcode sequences,
   detecting signals associated with the one or more detectably-labeled probes, and
   removing the one or more detectably-labeled probes, or
   (ii) contacting the biological sample with one or more intermediate probes that directly or indirectly bind to the one or more barcode sequences, wherein the one or more intermediate probes are detectable using one or more detectably-labeled probes, detecting signals associated with the one or more detectably-labeled probes, and removing the one or more intermediate probes and/or the one or more detectably-labeled probes.

20. The method of claim 1, wherein the recombinant polymerase generates a higher signal intensity in an RCA compared to a reference polymerase, wherein the reference polymerase is a Phi29 polymerase.

* * * * *